US012780906B2

(12) United States Patent
Fries et al.

(10) Patent No.: US 12,780,906 B2
(45) Date of Patent: Nov. 3, 2026

(54) ANTIBODIES AND METHODS OF USE

(71) Applicants: The United States Government as represented by the Department of Veterans Affairs, Washington, DC (US); The Research Foundation for the State University of New York, Albany, NY (US)

(72) Inventors: Bettina C. Fries, Stony Brook, NY (US); Kasturi Banerjee, Kansas City, MO (US); Michael P. Motley, Stony Brook, NY (US)

(73) Assignees: The United States Government as Represented by the Department of Veterans Affairs, Washington, DC (US); The Research Foundation for the State of New York, Albany, NY (US)

( * ) Notice: Subject to any disclaimer, the term of this patent is extended or adjusted under 35 U.S.C. 154(b) by 178 days.

(21) Appl. No.: 18/858,776

(22) PCT Filed: Apr. 20, 2023

(86) PCT No.: PCT/US2023/066009
§ 371 (c)(1),
(2) Date: Oct. 22, 2024

(87) PCT Pub. No.: WO2023/205731
PCT Pub. Date: Oct. 26, 2023

(65) Prior Publication Data

US 2025/0277016 A1 Sep. 4, 2025

Related U.S. Application Data

(60) Provisional application No. 63/333,611, filed on Apr. 22, 2022.

(51) Int. Cl.
*C07K 16/1228* (2026.01)
*A61K 39/00* (2006.01)

(52) U.S. Cl.
CPC ...... *C07K 16/1228* (2013.01); *A61K 2039/54* (2013.01); *A61K 2039/543* (2013.01); *C07K 2317/33* (2013.01); *C07K 2317/73* (2013.01); *C07K 2317/92* (2013.01)

(58) Field of Classification Search
None
See application file for complete search history.

(56) References Cited

FOREIGN PATENT DOCUMENTS

WO WO-2020/160156 A2 8/2020
WO WO-2020-193718 A1 10/2020

OTHER PUBLICATIONS

Diago-Navarro et I, Novel, Broadly Reactive Anticapsular Antibodies against Carbapenem-Resistant Klebsiella pneumoniae Protect from Infection, mBio, vol. 9, No. 2, published Apr. 3, 2018 (IDS filed May 5, 2025, NPL reference C).*
Brisse S, et al. wzi Gene sequencing, a rapid method for determination of capsular type for Klebsiella strains. Journal of clinical microbiology. 2013;51(12):4073-8.
Diago-Navarro E, et al. Carbapenem-resistant Klebsiella pneumoniae exhibit variability in capsular polysaccharide and capsule associated virulence traits. The Journal of infectious diseases. 2014;210(5):803-13.
Diago-Navarro E, et al. Novel, Broadly Reactive Anticapsular Antibodies against Carbapenem-Resistant Klebsiella pneumoniae Protect from Infection. mBio. 2018;9(2).
Gingerich AD, and Mousa JJ. Diverse Mechanisms of Protective Anti-Pneumococcal Antibodies. Frontiers in cellular and infection microbiology. 2022;12: 824788.
Heiss, C., et al. The Structure of Cryptococcus Neoformans Galactoxylomannan contains beta-D-glucuronic acid. (2009) Carbohydr. Res. 344: 915-920.
Kobayashi SD, et al. Antibody-Mediated Killing of Carbapenem-Resistant ST258 Klebsiella pneumoniae by Human Neutrophils. mBio. 2018;9(2): e00297.
Lang AB, et al. Human monoclonal antibodies specific for capsular polysaccharides of Klebsiella recognize clusters of multiple serotypes. Journal of immunology. 1991;146(9):3160-4.
Marsh JW, et al. Evolution of Outbreak-Causing Carbapenem-Resistant Klebsiella pneumoniae ST258 at a Tertiary Care Hospital over 8 Years. mBio. 2019;10(5): e01945.
Opoku-Temeng C, et al. Klebsiella pneumoniae capsule polysaccharide as a target for therapeutics and vaccines. Computational and structural biotechnology journal. 2019;17: 1360-6.
Parray HA, et al. Inhalation monoclonal antibody therapy: a new way to treat and manage respiratory infections. Applied microbiology and biotechnology. 2021;105(16-17):6315-32.
Raj GM, et al. Monoclonal Antibodies Against Infectious Microbes: So Long and Too Little!. Infectious disorders drug targets. 2021;21(1):4-27.
Rajewsky, K., The advent and rise of monoclonal antibodies. Nature. 2019;575(7781):47-9.
Seeberger PH, et al. A Semi-Synthetic Glycoconjugate Vaccine Candidate for Carbapenem-Resistant Klebsiella pneumonia. Angewandte Chemie. 2017;56(45):13973-8.
Van Duin D, et al. Molecular and clinical epidemiology of carbapenem-resistant Enterobacterales in the USA (CRACKLE-2): a prospective cohort study. The Lancet Infectious diseases. 2020; 20(6): 731-741.
Woodford N, et al. Multiresistant Gram-negative bacteria: the role of high-risk clones in the dissemination of antibiotic resistance. FEMS Microbiology Reviews. 2011;35(5):736-55.

(Continued)

*Primary Examiner* — Bao-Thuy L Nguyen
*Assistant Examiner* — Bonirath Chhay
(74) *Attorney, Agent, or Firm* — Ballard Spahr LLP

(57) ABSTRACT

Disclosed herein are anti-*Klebsiella pneumonia* sequence type 258 wzi50, wzi154, or wzi29 capsular polysaccharide antibodies useful in inhibiting, treating or preventing *Klebsiella pneumonia* ST258 infections in a subject.

19 Claims, 23 Drawing Sheets

Specification includes a Sequence Listing.

(56) References Cited

OTHER PUBLICATIONS

Wu MF, et al. Humoral immunity against capsule polysaccharide protects the host from magA+ Klebsiella pneumoniae-induced lethal disease by evading Toll-like receptor 4 signaling. Infection and immunity. 2009;77(2):615-21.

International Search Report and Written Opinion were mailed on Oct. 11, 2023 by the International Searching Authority for International Application No. PCT/US2023/066009, filed on Apr. 20, 2023 and published as WO/2023/205731 on Oct. 26, 2023 (Applicant—The United States Government as Represented by the Department of Veterans Affairs) (6 Pages).

International Preliminary Report on Patentability was mailed on Oct. 8, 2023 by the International Searching Authority for International Application No. PCT/US2023/066009, filed on Apr. 20, 2023 and published as WO/2023/205731 on Oct. 26, 2023 (Applicant—The United States Government as Represented by the Department of Veterans Affairs) (7 Pages).

* cited by examiner

| Kp strain | Agglutination | %survival ±SD in WBC assay |
|---|---|---|
| *wzi* 29 | | |
| *Kp3* | ++++ | 4.81%±8.6% |
| *Kp10* | ++++ | |
| *Kp22* | Negative | NS |
| *Kp29* | + | 77%±8% |
| *Kp36*** | ++ | 4.5%±0.5% |
| *Kp37* | ++++ | |
| *Kp44* | ++++ | |
| *Kp54* | +++ | 40.5%±5% |
| *ESBL12* | ++ | 5.8%±0.8% |
| *ESBL30* | ++ | 17.8%±1.6% |
| *ESBL31* | ++ | NS |
| wzi 50 | | |
| *Kp14* | +++ | 57%±0.6% |
| *Kp15* | ++++ | 19%±1.7% |
| *Kp18* | ++++ | |
| *Kp19* | ++++ | |
| *Kp38*** | ++++ | 41%±0.8% |
| *Kp41* | ++++ | |
| *Kp42* | ++++ | |
| *Kp43* | ++++ | |

| Kp strain | Agglutination | %survival ±SD in WBC assay |
|---|---|---|
| *wzi* 154 | | |
| *Kp1* | ++++ | 8.28%±0.1% |
| *Kp2* | ++++ | |
| *Kp5* | ++++ | |
| *Kp6* | ++++ | |
| *Kp11* | ++++ | |
| *Kp13* | ++ | 25.11%±1% |
| *Kp24* | ++++ | |
| *Kp25* | ++++ | |
| *Kp26* | ++ | 77%±15% |
| *Kp28* | ++ | |
| Kp30 | Negative | NS |
| *Kp34*** | ++ | 38.6%±7.2% |
| *ESBL6* | +++ | 54.1%±1.5% |
| *ESBL15* | ++++ | |
| *ESBL20* | ++++ | |
| *ESBL22* | ++++ | |
| *ESBL28* | ++++ | 52%±5.6% |
| *ESBL39* | ++++ | |
| *ESBL43* | ++++ | 17.4%±12.5% |

FIG. 17A

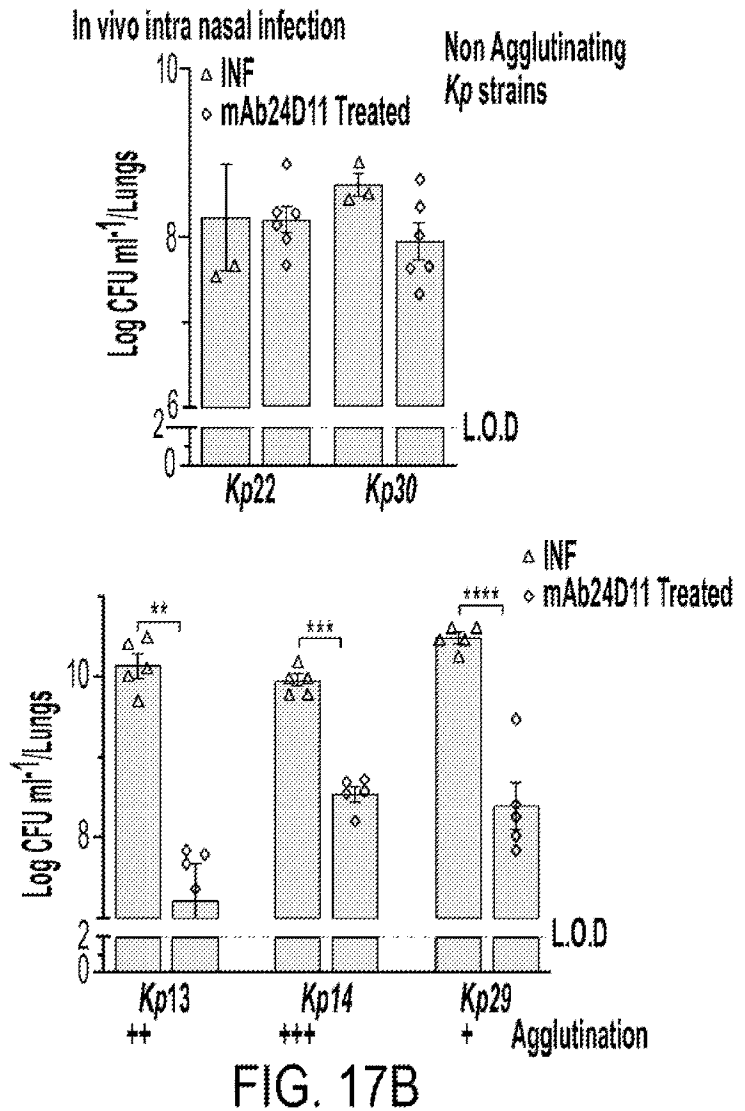

FIG. 17B

SEQUENCE LISTING

```
Sequence total quantity: 20
SEQ ID NO: 1            moltype = AA  length = 16
FEATURE                 Location/Qualifiers
source                  1..16
                        mol_type = protein
                        organism = synthetic construct
SEQUENCE: 1
KSSQSLLYSN GKTYLN                                                   16

SEQ ID NO: 2            moltype = AA  length = 7
FEATURE                 Location/Qualifiers
source                  1..7
                        mol_type = protein
                        organism = synthetic construct
SEQUENCE: 2
LVSKLDS                                                             7

SEQ ID NO: 3            moltype = AA  length = 9
FEATURE                 Location/Qualifiers
source                  1..9
                        mol_type = protein
                        organism = synthetic construct
SEQUENCE: 3
VQGTHFPQT                                                           9

SEQ ID NO: 4            moltype = AA  length = 112
FEATURE                 Location/Qualifiers
source                  1..112
                        mol_type = protein
                        organism = synthetic construct
SEQUENCE: 4
DVVMTQTPLT LSVTIGQPAS ISCKSSQSLL YSNGKTYLNW LLQRPGQSPK RLIYLVSKLD  60
SGVPDRFTGS GSGTDFTLKI SRVEAEDLGV YYCVQGTHFP QTFGGGTKLE IK          112

SEQ ID NO: 5            moltype = AA  length = 5
FEATURE                 Location/Qualifiers
source                  1..5
                        mol_type = protein
                        organism = synthetic construct
SEQUENCE: 5
NYVIH                                                               5

SEQ ID NO: 6            moltype = AA  length = 17
FEATURE                 Location/Qualifiers
source                  1..17
                        mol_type = protein
                        organism = synthetic construct
SEQUENCE: 6
YINPYSDGTK YNEKFKD                                                  17

SEQ ID NO: 7            moltype = AA  length = 14
```

```
FEATURE               Location/Qualifiers
source                1..14
                      mol_type = protein
                      organism = synthetic construct
SEQUENCE: 7
GGPYYDYGGY TMDY                                                  14

SEQ ID NO: 8          moltype = AA  length = 123
FEATURE               Location/Qualifiers
source                1..123
                      mol_type = protein
                      organism = synthetic construct
SEQUENCE: 8
EVQLQQSGPE LVKPGASVKM SCKASGYTFT NYVIHWVKQK PGQGLEWIGY INPYSDGTKY  60
NEKFKDKATL TSDKSSSTAY MELISLTSED SAVYYCARGG PYYDYGGYTM DYWGQGTSVT  120
VSS                                                              123

SEQ ID NO: 9          moltype = AA  length = 238
FEATURE               Location/Qualifiers
source                1..238
                      mol_type = protein
                      organism = synthetic construct
SEQUENCE: 9
MSPAQFLFLL VLWIQETNGD VVMTQTPLTL SVTIGQPASI SCKSSQSLLY SNGKTYLNWL  60
LQRPGQSPKR LIYLVSKLDS GVPDRFTGSG SGTDFTLKIS RVEAEDLGVY YCVQGTHFPQ  120
TFGGGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 10         moltype = AA  length = 219
FEATURE               Location/Qualifiers
source                1..219
                      mol_type = protein
                      organism = synthetic construct
SEQUENCE: 10
DVVMTQTPLT LSVTIGQPAS ISCKSSQSLL YSNGKTYLNW LLQRPGQSPK RLIYLVSKLD  60
SGVPDRFTGS GSGTDFTLKI SRVEAEDLGV YYCVQGTHFP QTFGGGTKLE IKRADAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                        219

SEQ ID NO: 11         moltype = AA  length = 478
FEATURE               Location/Qualifiers
source                1..478
                      mol_type = protein
                      organism = synthetic construct
SEQUENCE: 11
MEWSWIFLFL LSGTAGVHSE VQLQQSGPEL VKPGASVKMS CKASGYTFTN YVIHWVKQKP  60
GQGLEWIGYI NPYSDGTKYN EKFKDKATLT SDKSSSTAYM ELISLTSEDS AVYYCARGGP  120
YYDYGGYTMD YWGQGTSVTV SSAKTTPPSV YPLAPGCGDT TGSSVTLGCL VKGYFPESVT  180
VTWNSGSLSS SVHTFPALLQ SGLYTMSSSV TVPSSTWPSQ TVTCSVAHPA SSTTVDKKLE  240
PSGPISTINP CPPCKECHKC PAPNLEGGPS VFIFPPNIKD VLMISLTPKV TCVVVDVSED  300
DPDVQISWFV NNVEVHTAQT QTHREDYNST IRVVSTLPIQ HQDWMSGKEF KCKVNNKDLP  360
SPIERTISKI KGLVRAPQVY ILPPPAEQLS RKDVSLTCLV VGFNPGDISV EWTSNGHTEE  420
NYKDTAPVLD SDGSYFIYSK LNMKTSKWEK TDSFSCNVRH EGLKNYYLKK TISRSPGK    478

SEQ ID NO: 12         moltype = AA  length = 459
FEATURE               Location/Qualifiers
source                1..459
                      mol_type = protein
                      organism = synthetic construct
SEQUENCE: 12
EVQLQQSGPE LVKPGASVKM SCKASGYTFT NYVIHWVKQK PGQGLEWIGY INPYSDGTKY  60
NEKFKDKATL TSDKSSSTAY MELISLTSED SAVYYCARGG PYYDYGGYTM DYWGQGTSVT  120
VSSAKTTPPS VYPLAPGCGD TTGSSVTLGC LVKGYFPESV TVTWNSGSLS SSVHTFPALL  180
QSGLYTMSSS VTVPSSTWPS QTVTCSVAHP ASSTTVDKKL EPSGPISTIN PCPPCKECHK  240
CPAPNLEGGP SVFIFPPNIK DVLMISLTPK VTCVVVDVSE DDPDVQISWF VNNVEVHTAQ  300
TQTHREDYNS TIRVVSTLPI QHQDWMSGKE FKCKVNNKDL PSPIERTISK IKGLVRAPQV  360
YILPPPAEQL SRKDVSLTCL VVGFNPGDIS VEWTSNGHTE ENYKDTAPVL DSDGSYFIYS  420
KLNMKTSKWE KTDSFSCNVR HEGLKNYYLK KTISRSPGK                        459

SEQ ID NO: 13         moltype = DNA  length = 48
FEATURE               Location/Qualifiers
source                1..48
                      mol_type = other DNA
                      organism = synthetic construct
SEQUENCE: 13
aagtcaagtc agagcctctt atatagtaat ggaaaaacct atttgaat             48

SEQ ID NO: 14         moltype = DNA  length = 21
FEATURE               Location/Qualifiers
```

```
source                  1..21
                        mol_type = other DNA
                        organism = synthetic construct
SEQUENCE: 14
ctggtgtcta aactggactc t                                            21

SEQ ID NO: 15           moltype = DNA  length = 27
FEATURE                 Location/Qualifiers
source                  1..27
                        mol_type = other DNA
                        organism = synthetic construct
SEQUENCE: 15
gtgcaaggta cacattttcc tcagacg                                      27

SEQ ID NO: 16           moltype = DNA  length = 717
FEATURE                 Location/Qualifiers
source                  1..717
                        mol_type = other DNA
                        organism = synthetic construct
SEQUENCE: 16
atgagtcctg cccagttcct gtttctgtta gtgctctgga ttcaggaaac caacggtgat  60
gttgtgatga cccagactcc actcactttg tcggttacca ttggacaacc agcctctatc  120
tcttgcaagt caagtcagag cctcttatat agtaatggaa aaacctattt gaattggtta  180
ttacagaggc caggccagtc tccaaagcgc ctaatctatc tggtgtctaa actggactct  240
ggagtccctg acaggttcac tggcagtgga tcaggaacag attttacact gaaaatcagc  300
agagtggagg ctgaggattt gggagtttat tactgcgtgc aaggtacaca ttttcctcag  360
acgttcggtg gaggcaccaa gctggaaatc aaacgggctg atgctgcacc aactgtatcc  420
atcttcccac catccagtga gcagttaaca tctggaggtg cctcagtcgt gtgcttcttg  480
aacaacttct accccaaaga catcaatgtc aagtggaaga ttgatggcag tgaacgacaa  540
aatggcgtcc tgaacagttg gactgatcag gacagcaaag acagcaccta cagcatgagc  600
agcaccctca cgttgaccaa ggacgagtat gaacgacata acagctatac ctgtgaggcc  660
actcacaaga catcaacttc acccattgtc aagagcttca acaggaatga gtgttag     717

SEQ ID NO: 17           moltype = DNA  length = 15
FEATURE                 Location/Qualifiers
source                  1..15
                        mol_type = other DNA
                        organism = synthetic construct
SEQUENCE: 17
aactatgtta tacac                                                   15

SEQ ID NO: 18           moltype = DNA  length = 51
FEATURE                 Location/Qualifiers
source                  1..51
                        mol_type = other DNA
                        organism = synthetic construct
SEQUENCE: 18
tatattaatc cttacagtga tggtactaag tacaatgaga agttcaaaga c           51

SEQ ID NO: 19           moltype = DNA  length = 42
FEATURE                 Location/Qualifiers
source                  1..42
                        mol_type = other DNA
                        organism = synthetic construct
SEQUENCE: 19
ggggggccct actatgatta cggagggtat actatggact ac                     42

SEQ ID NO: 20           moltype = DNA  length = 1437
FEATURE                 Location/Qualifiers
source                  1..1437
                        mol_type = other DNA
                        organism = synthetic construct
SEQUENCE: 20
atggaatgga gttggatatt tctctttctc ctgtcaggaa ctgcaggtgt ccactctgag  60
gtccagctgc agcagtctgg acctgagctg gtaaagcctg ggcttcagt gaagatgtcc   120
tgcaaggctt ctggatacac attcactaac tatgttatac actgggtgaa gcagaagcct  180
gggcagggcc ttgagtggat tggatatatt aatccttaca gtgatggtac taagtacaat  240
gagaagttca aagacaaggc cacactgact tcagacaaat cctccagcac agcctacatg  300
gagctcatca gcctgacctc tgaggactct gcggtctatt actgtgcaag aggggggccc  360
tactatgatt acggagggta tactatggac tactggggtc aaggaacctc agtcaccgtc  420
tcctcagcca aaacaacacc cccatcagtc tatccactgg cccctgggtg tggagataca  480
actggttcct ccgtgactct gggatgcctg gtcaagggct acttccctga gtcagtgact  540
gtgacttgga actctggatc cctgtccagc agtgtgcaca ccttcccagc tctcctgcag  600
tctggactct acactatgag cagctcagtg actgtcccct ccagcacctg gccaagtcag  660
accgtcacct gcagcgttgc tcacccagcc agcagcacca cggtggacaa aaaacttgag  720
cccagcgggc ccatttcaac aatcaacccc tgtcctccat gcaaggagtg tcacaaatgc  780
ccagctccta acctcgaggg tggaccatcc gtcttcatct tccctccaaa tatcaaggat  840
gtactcatga tctccctgac acccaaggtc acgtgtgtgg tggtggatgt gagcgaggat  900
gacccagacg tccagatcag ctggtttgtg aacaacgtgg aagtacacac agctcagaca  960
```

-continued

```
caaacccata gagaggatta caacagtact atccgggtgg tcagcaccct ccccatccag 1020
caccaggact ggatgagtgg caaggagttc aaatgcaagg tcaacaacaa agacctccca 1080
tcacccatcg agagaaccat ctcaaaaatt aaagggctag tcagagctcc acaagtatac 1140
atcttgccgc caccagcaga gcagttgtcc aggaaagatg tcagtctcac ttgcctggtc 1200
gtgggcttca accctggaga catcagtgtg gagtggacca gcaatgggca tacagaggag 1260
aactacaagg acaccgcacc agtcctggac tctgacggtt cttacttcat atatagcaag 1320
ctcaatatga aaacaagcaa gtgggagaaa acagattcct tctcatgcaa cgtgagacac 1380
gagggtctga aaaattacta cctgaagaag accatctccc ggtctccggg taaatga 1437
```

ANTIBODIES AND METHODS OF USE

CROSS REFERENCE TO RELATED APPLICATIONS

This application claims the benefit of priority under 35 U.S.C. § 371 of International Application No. PCT/US2023/066009, filed on Apr. 20, 2023, which claims the benefit of the filing date of U.S. Provisional Application No. 63/333,611, filed on Apr. 22, 2022. The content of this these earlier filed applications is hereby incorporated by reference herein in its entirety.

STATEMENT REGARDING FEDERALLY FUNDED RESEARCH

This invention was made with government support under grant number 5101 5BX003741 awarded by the United States Department of Veterans Affairs and grant number AI140611 awarded by the National Institutes of Health. The government has certain rights in the invention.

INCORPORATION OF THE SEQUENCE LISTING

The present application contains a sequence listing that is submitted concurrent with the filing of this application, containing the file name "37759_0446P1_SL" which is 24,576 bytes in size, created on Mar. 30, 2023, and is herein incorporated by reference in its entirety pursuant to 37 C.F.R. § 1.52(e)(5).

BACKGROUND

Therapeutic monoclonal antibodies (mAbs) have emerged as a major therapeutic modality to treat cancer and immune disorders (Rajewsky, K., *Nature.* 2019; 575(7781):47-9), and efforts to use mAbs against infectious disease are emerging (Raj G M, et al. *Infectious disorders drug targets.* 2021; 21(1):4-27; and Parray H A, et al. *Applied microbiology and biotechnology.* 2021; 105(16-17):6315-32). These efforts are important given the urgency to develop treatments to combat multi-drug resistant pathogens, such as high-mortality Carbapenem-resistant *Klebsiella pneumoniae* (CR-Kp) infections, as instances of antibiotic resistance continues to rise (Woodford N, et al. *FAMS microbiology reviews.* 2011; 35(5):736-55; and van Duin D, Arias C A, et al. *The Lancet Infectious diseases.* 2020). CR-Kp virulence is mediated by capsular polysaccharide (CPS), which has been a useful immunogenic target for other organisms (Gingerich A D, and Mousa J J. *Frontiers in cellular and infection microbiology.* 2022; 12(824788)). However, antigenic diversity limits monoclonal antibody uses as a broader therapy. Numerous Kp CPS serotypes exist, which are characterized by PCR-sequencing of the capsular adhesion gene WZI (Brisse S, Passet V, et al. *Journal of clinical microbiology.* 2013; 51(12):4073-8). In the United States, nearly 60% of CR-Kp strains infecting humans are sequence type ST258 and their correlated clonal lineages (clonal group 258 [CG258]), and among these wzi29, wzi154 and 12.5% have been identified (Diago-Navarro E, et al. *The Journal of infectious diseases.* 2014; 210(5):803-13; Marsh J W, et al. mBio. 2019; 10(5); and van Duin D, Arias C A, et al. *The Lancet* Infectious diseases. 2020).

Previous studies have developed mAbs and immunotherapies that target capsular polysaccharides including the wzi154 CPS of ST258 (Diago-Navarro E, et al. mBio. 2018; 9(2); Kobayashi S D, Porter A R, Freedman B, Pandey R, Chen L, Kreiswirth B N, and DeLeo F R.

Antibody-Mediated Killing of Carbapenem-Resistant ST258 *Klebsiella pneumoniae* by Human Neutrophils. *mRio.* 2018; 9(2); Lang A B, et al. *Journal of immunology.* 1991; 146(9):3160-4; Wu M F, et al. *Infection and immunity.* 2009; 77(2):615-21; Opoku-Temeng C, et al. *Computational and structural biotechnology journal.* 2019; 17(1360-6); Seeberger P H, et al. *Angewandte Chemie.* 2017; 56(45): 13973-8). However, less success has been observed in providing adequate coverage against wzi29 and wzi50 CPS strains. As means to accurately serotype in the clinical setting are few, maximizing coverage of the predominant serotypes remains an important challenge for developing a passive immunotherapy.

SUMMARY

Disclosed herein are isolated antibodies comprising a light chain variable region and a heavy chain variable region, wherein the light chain variable region comprises a complementarity determining region light chain 1 (CDRL1) amino acid sequence of SEQ ID NO: 1; a complementarity determining region light chain 2 (CDRL2) amino acid sequence of SEQ ID NO: 2; and a complementarity determining region light chain 3 (CDRL3) amino acid sequence of SEQ ID NO: 3; and wherein the heavy chain variable region comprises a complementarity determining region heavy chain 1 (CDRH1) amino acid sequence of SEQ ID NO: 5; a complementarity determining region heavy chain 2 (CDRH2) amino acid sequence of SEQ ID NO: 6; and a complementarity determining region heavy chain 3 (CDRH3) amino acid sequence of SEQ ID NO: 7.

Disclosed herein are isolated antibodies comprising a light chain variable region amino acid sequence of SEQ ID NO: 4 and a heavy chain variable region amino acid sequence of SEQ ID NO: 8.

Disclosed herein are isolated antibodies comprising a light chain variable region and a heavy chain variable region, wherein the light chain variable region comprises a complementarity determining region light chain 1 (CDRL1) amino acid sequence of SEQ ID NO: 1; a determining region light chain 2 (CDRL2) amino acid sequence of SEQ ID NO: 2; and a determining region light chain 3 (CDRL3) amino acid sequence of SEQ ID NO: 3; and wherein the heavy chain variable region comprises a complementarity determining region heavy chain 1 (CDRH1) amino acid sequence of SEQ ID NO: 5; a complementarity determining region heavy chain 2 (CDRH2) amino acid sequence of SEQ ID NO: 6; and a complementarity determining region heavy chain 3 (CDRH3) amino acid sequence of SEQ ID NO: 7, wherein one or more of the CDRL1, CDRL2, CDRL3, CDRH1, CDRH2, or CDRH3 comprise 1, 2, 3, 4, or 5 conservative amino acid substitutions.

Disclosed herein are isolated antibodies comprising a light chain variable region amino acid sequence of SEQ ID NO: 4 and a heavy chain variable region amino acid sequence of SEQ ID NO: 8, wherein the isolated antibody comprises 1, 2, 3, 4, or 5 conservative amino acid substitutions in the light or heavy chain variable region amino acid sequences.

Disclosed herein are isolated antibodies comprising a light chain variable region and a heavy chain variable region, wherein the light chain variable region comprises: a) a variant complementarity determining region light chain 1 (CDRL1) comprising positions 24-39 of SEQ ID NO: 4, wherein the variant CDRL 1 comprises one or two amino acid substitutions; b) a variant complementarity determining region light chain 2(CDRL2) comprising positions 55-61 of SEQ ID NO: 4, wherein the variant CDRL2 comprises one or two amino acid substitutions; and b) a variant complementarity determining region light chain 3(CDRL3) comprising positions 94-102 of SEQ ID NO: 4, wherein the variant CDRL3 comprises one or two amino acid substitutions; wherein the heavy chain variable region comprises: d) a variant complementarity determining region heavy chain 1 (CDRH1) comprising positions 31-35 of SEQ ID NO: 8, wherein the variant CDRH1 comprises one or two amino acid substitutions; e) a variant complementarity determining region heavy chain 2 (CDRH2) comprising positions 50-66 of SEQ ID NO: 8, wherein the variant CDRH2 comprises one or two amino acid substitutions; and f) a variant complementarity determining region heavy chain 3 (CDRH3) comprising positions 99-112 of SEQ ID NO: 8, wherein the variant CDRH3 comprises one or two amino acid substitutions.

BRIEF DESCRIPTION OF THE DRAWINGS

FIG. 1 also shows the serum IgG Titers of wzi50 CPS-vaccinated mice. Serum IgG Titers of wzi50 CPS-vaccinated mice: Serum form mice was collected 8 weeks post the start of biweekly vaccination course with either BaPA-conjugated wzi50 CPS, unconjugated wzi50 CPS, or PBS in Complete/Incomplete Fruend's Adjuvant. Mice sera was tested by ELISA against the conjugated CPS, unconjugated CPS, and whole bacteria (wzi29, wzS50, and wzi154). Titers are calculated as the lowest serum dilution where O.D. of vaccinated mice serum ≥2.5 times the O.D. of naïve mouse serum. Each symbol represents one mouse, and the dotted line indicates the titer of 1/10000 above which candidates for splenic fusion were selected.

FIG. 4A shows the inhibition to the binding of monoclonal antibody 24D11 at 40 μg/ml to both CPSs that was tested against the increasing concentration of 171112 (0-80 μg/ml). FIG. 4B shows the inhibition to the binding of monoclonal antibody 17H12 at 40 μg/ml to both CPSs was tested against the increasing concentration of monoclonal antibody 24D11 (0-80 μg/ml). FIGS. 4A-B show an anti-mouse IgG2b secondary used for mAb 24D11, and an anti-mouse IgG3 secondary used for mAb 17H12. Points plotted are the average of duplicate values from 2 separate replicates of the competitive ELISA experiments and are plotted both as raw $OD_{405}$ values (FIGS. 4A-B left) and as percentage binding affinity where $IC_5u$ based on the Nonlinear regression fit curve designates Inhibitory Concentration at which 50% of the binding affinity of either monoclonal antibody 24D11 or monoclonal antibody 17H12 at 40 μg/ml to purified CPSs was lost (FIGS. 4A-B right).

FIG. 9B shows that the bacterial burden in the lungs of C57BL/6 mice depleted of neutrophils (Ly6G) or administered a control antibody and subsequently infected with 100 μl of $1\times10^8$ CFU/ml inoculum of SBU116, with or without post-surgical treatment with 24D11 (10 mg/kg). Immunophenotyping of immune cells engaged in CR-Kp clearance from lungs of control of neutropenic mice using Flow Cytometry and analyzed by BD FACSDiva™ and Flowing Software, with gating scheme demonstrated in FIG. 11. Immune cells are depicted in the graph as follows: Neutrophils-black triangle, M1 Macrophages-Greyish blue squares, M2 Macrophages-Maroon inverted-triangle, Inflammatory Monocytes-Purple diamond, Resident Monocytes—Mustard circles (FIG. 9C). Measurement of cytokines IL-17 (FIG. 9D) and TNF-α (FIG. 9E) was performed using BioLegend® ELISA Max™ Deluxe set (Cat #436204 & 430904). For the studies, overall differences in CFU, percentage population, or cytokine levels between treatment groups and between neutrophil status were assessed for significance by two-way ANOVA. Individual comparisons made within wild-type with or without 24D11 treatment (* symbols above) or comparisons made within neutropenic groups of mice with or without monoclonal antibody 24D11 treatment (#symbols above) were tested using Tukey's post hoc test with p-values displayed in the graph. In the immune cells graphed p-values in black* depicts comparison within wildtype with or without monoclonal antibody 24D11 treatment, p- and p-values in #depicts comparison within the treatment groups of mice of the same neutrophil status. Data is shown as Mean±SEM and p-values are replaced with ns if >0.1, * if <0.05,  if <0.01, * if <0.001, and **** if <0.0001.

FIG. 11A shows phagocytosis of wzi154 MMC34 by J774.A1 murine macrophage-like cells after incubation with 40 μg/ml of either monoclonal antibody 24D11, monoclonal antibody 17H12 or combination of both antibodies with and without normal human serum. Bars depict means and SDs of three independent experiments, with wells performed in triplicate. Differences between PBS and other treatment groups (*) with or without serum, differences between monoclonal antibody 24D11 and combination group with or without serum (+) and differences between monoclonal antibody17H12 and combination group with or without serum (#) were assessed for significance by repeated-measures two-way ANOVA with results of Tukey's post hoc test for multiple comparisons displayed in the graph. p-values are replaced with ns if ≥0.05, * if <0.05,  if <0.01, and * if <0.001. FIG. 11B shows that bacterial burden in lungs, livers, and spleens of mice infected with $1\times10^8$ CFU/ml inoculum of MMC34 intraperitoneally treated with 40 μg/ml of either monoclonal antibody 24D11, monoclonal antibody 17H12, or in combination 4 hours post-surgery. Differences in CFU within treatment groups were assessed for significance by two-way ANOVA. Individual comparisons made within treatment groups were tested using Tukey's post hoc test with p-values displayed in the graph. p-values in red depicts comparison between wildtype and antibody treated mice, p-values in purple depicts comparison between monoclonal antibody 17H12 treated mice and monoclonal antibody 24D11 or combination treated mice. Each dot represents one mouse. Data is shown as Mean±SD and p-values are replaced with ns if >0.1, * if <0.05,  if <0.01, * if <0.001, and **** if <0.0001.

FIG. 14A shows clonal distribution of CR-Kp pathogens within the United States as determined by data from the CRACKLE II study ((Molecular and clinical epidemiology of carbapenem-resistant Enterobacterales in the USA (CRACKLE-2). CG258 and CG307 are dominant clones. FIG. 14B shows the diversity of wzi types in (n=96) within CR-Kp ST258 strains from NY in 2013. The wzi154, wzi29, and wzi50 are dominant wzi-types of CPS.

FIG. 15A shows that patients infected with CR-Kp exhibit cross-reactive polyclonal humoral responses (antibodies) to wzi50 CPS whereas purified wzi29 CPS does not bind antibodies. FIG. 15B shows that even patients infected with wzi29-expressing CR-Kp secrete antibodies that bind to wzi50 CPS.

FIG. 16A shows intra tracheal infection with PBS as control. FIG. 16B shows intra nasal infection with irrelevant isotype specific antibody as control.

FIGS. 17A-B show binding data for CR-Kp strains. FIG. 17A is a table showing variable degree of agglutination of ST258 Kp strains and extended-spectrum β-lactamase Kp (ESBL-Kp) strains. Agglutination was assessed by microscopy. No agglutination was seen in Kp22, and Kp30 and in the presence of irrelevant IgG2b control antibody. WBC assay demonstrated decreased survival in monoclonal antibody 24D11-treated ST258 Kp strains when compared to isotype control antibody-treated Kp. Kp22 and Kp30 exhibited no survival difference. ESBL-Kp strains, ESBL6 and ESBL28, expressing wzi154 CPS showed >50% decrease in survival in the WBC assay. FIG. 17B shows that in intranasal infection with Kp22, Kp30 showed no protective efficacy of 24D11. For Kp13, Kp14, Kp29, which exhibit variable agglutination. Protective efficacy of 24D11 was confirmed.

DETAILED DESCRIPTION

Figure 1:
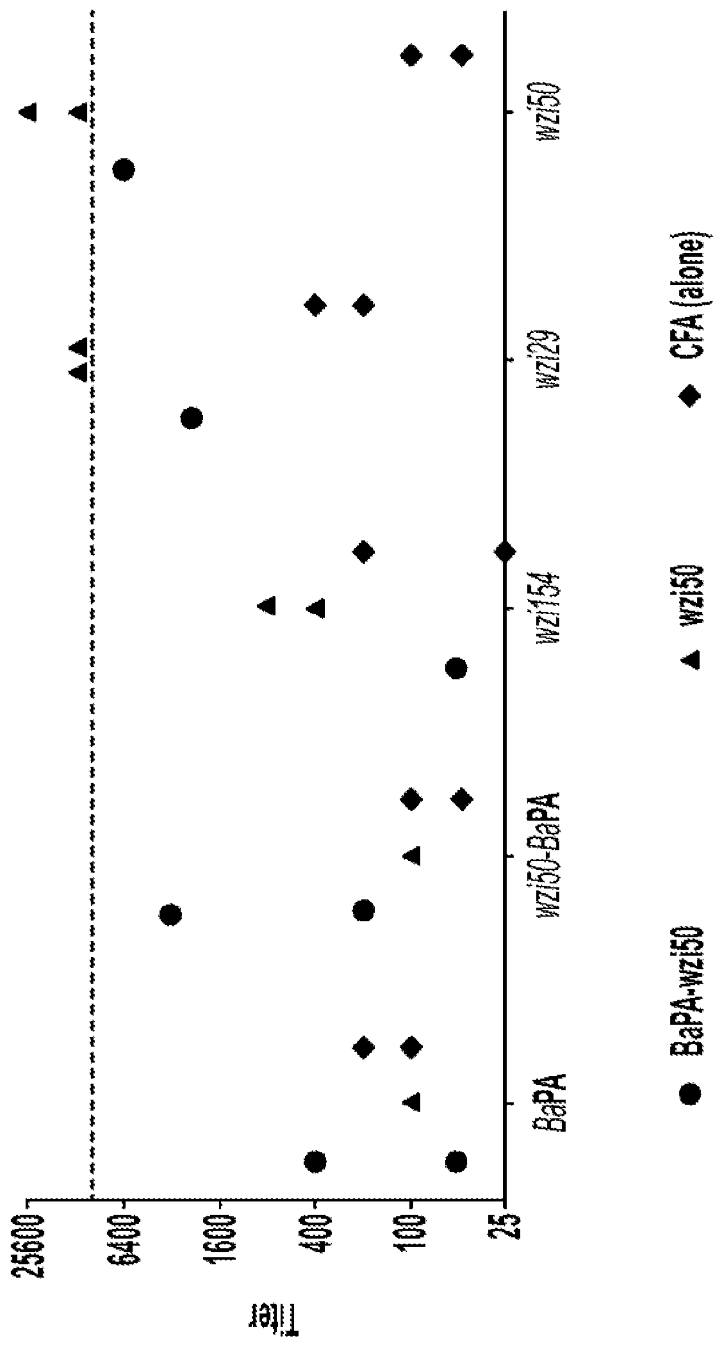
FIG. 1 shows the agglutination properties of monoclonal antibodies against wzi50.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list. Further, the term "or" means "and/or" unless explicitly indicated to refer to alternatives only or the alternatives are mutually exclusive, although the disclosure supports a definition that refers to only alternatives and "and/or."

As used herein, the term "another" means at least a second or more.

As used herein, the term "about" is used to indicate that a value includes the inherent variation of error for the device, the method being employed to determine the value, or the variation that exists among the study subjects.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject is a mammal. In some aspects, a subject is a human. The term does not denote a particular age or sex. Thus, adult, child, adolescent and newborn subjects, as well as fetuses, whether male or female, are intended to be covered. As used herein, the term "subject" refers to either a human or a non-human animal, such as primates, mammals, and vertebrates having *Klebsiella pneumonia* ST258 infection or diagnosed with a *Klebsiella pneumonia* ST258 infection or exposed to *Klebsiella pneumonia* ST258. In some aspects, the subject in need will or is predicted to benefit from anti-*Klebsiella pneumoniae* sequence type 258 wzi50, wzi154 or wzi29 capsular polysaccharide antibody treatment.

As used herein, the term "patient" refers to a subject afflicted with a disease or disorder. The term "patient" includes human and veterinary subjects. In some aspects of the disclosed methods, the "patient" has been diagnosed with a need for treatment for a *Klebsiella pneumonia* ST258 infection or to prevent a *Klebsiella pneumonia* ST258 infection, such as, for example, prior to the administering step.

As used herein, the term "treat," "treatment," or "treating" refers to administration or application of a therapeutic agent to a subject in need thereof, or performance of a procedure or modality on a subject, for the purpose of obtaining at least one positive therapeutic effect or benefit, such as treating a disease or health-related condition. For example, a treatment can include administration of a pharmaceutically effective amount of an antibody, or a composition or formulation thereof that specifically binds to *Klebsiella pneumoniae* sequence type 258 wzi50, wzi154 or wzi29 capsular polysaccharide for the purpose of treating or preventing *Klebsiella pneumonia* ST258 infection. The terms "treatment regimen," "dosing regimen," or "dosing protocol," are used interchangeably and refer to the timing and dose of a therapeutic agent, such as an anti-*Klebsiella pneumoniae* sequence type 258 wzi50, wzi154 or wzi29 capsular polysaccharide antibody as described herein.

As used herein, the term "therapeutic benefit" or "therapeutically effective" refers the promotion or enhancement of the well-being of a subject in need (e.g., a subject with an *Klebsiella pneumonia* ST258 or diagnosed with *Klebsiella pneumonia* ST258 infection or a subject exposed to *Klebsiella pneumonia* ST258) with respect to the medical treatment, therapy, dosage administration, of a condition, particularly as a result of the use of the anti-*Klebsiella pneumoniae* sequence type 258 wzi50, wzi154 or wzi29 capsular polysaccharide antibodies and the performance of the described methods. This includes, but is not limited to, a reduction in the frequency or severity of the signs or symptoms of a disease or infection. In some aspects, treatment or prevention of an infection may involve, for instance, inducing an immune response, inducing complement-mediated or complement-independent opsonophagocytosis, reducing lung burden or dissemination of *Klebsiella pneumonia* ST258, reducing in lung, liver or spleen bacterial load of a *Klebsiella pneumonia* ST258 infection, or increasing opsonophagocytic uptake. Treatment or prevention of *Klebsiella pneumonia* ST258 may also refer to achieving a sustained response in a subject.

As used herein, the term "administer" or "administration" refers to the act of physically delivering, e.g., via injection or an oral route, a substance as it exists outside the body into a patient, such as by oral, subcutaneous, mucosal, intradermal, intravenous, intramuscular delivery and/or any other method of physical delivery described herein or known in the art. When a disease, disorder or condition, or a symptom thereof, is being treated therapeutically, administration of the substance typically occurs after the onset of the disease, disorder or condition or symptoms thereof. Prophylactic treatment involves the administration of the substance at a time prior to the onset of the disease, disorder or condition or symptoms thereof.

As used herein, the term "effective amount" refers to the quantity or amount of a therapeutic (e.g., an antibody or pharmaceutical composition provided herein) which is sufficient to reduce, diminish, alleviate, and/or ameliorate the severity and/or duration of a *Klebsiella pneumonia* ST258 infection, *Klebsiella pneumonia* infection or a symptom related thereto. This term also encompasses an amount necessary for the reduction or amelioration of the advancement or progression of a *Klebsiella pneumonia* ST258 infection or other *Klebsiella pneumonia* infection; the reduction or amelioration of the recurrence, development of a *Klebsiella pneumonia* ST258 infection or other *Klebsiella pneumonia* infection or onset of a *Klebsiella pneumonia* ST258 infection or other *Klebsiella pneumonia* infection; and/or the improvement or enhancement of the prophylactic or therapeutic effect(s) of another immunological or antibiotic therapy. In some aspects, the effective amount of an antibody provided herein is from about or equal to 0.1 mg/kg (mg of antibody per kg weight of the subject) to about or equal to 100 mg/kg. In some aspects, an effective amount of an antibody provided therein is about or equal to 0.1 mg/kg, about or equal to 0.5 mg/kg, about or equal to 1 mg/kg, about or equal to 3 mg/kg, about or equal to 5 mg/kg, about or equal to 10 mg/kg, about or equal to 15 mg/kg, about or equal to 20 mg/kg, about or equal to 25 mg/kg, about or equal to 30 mg/kg, about or equal to 35 mg/kg, about or equal to 40 mg/kg, about or equal to 45 mg/kg, about or equal to 50 mg/kg, about or equal to 60 mg/kg, about or equal to 70 mg/kg, 80 mg/kg, 90 mg/kg, or 100 mg/kg. These amounts are meant to include amounts and ranges therein. In some aspects, "effective amount" also refers to the amount of an antibody provided herein to achieve a specified result (e.g., preventing, blocking, or inhibiting a *Klebsiella pneumonia* ST258 infection or other *Klebsiella pneumonia* infections).

The term "in combination" in the context of the administration of other therapies (e.g., other agents, antibiotics) includes the use of more than one therapy (e.g., drug therapy and/or antibiotic therapy). Administration "in combination with" one or more further therapeutic agents includes simultaneous (e.g., concurrent) and consecutive administration in any order. The use of the term "in combination" does not restrict the order in which therapies are administered to a subject By way of nonlimiting example, a first therapy (e.g., agent, such as an anti-*Klebsiella pneumoniae* sequence type 258 wzi50, wzi154 or wzi29 capsular polysaccharide antibody) may be administered before (e.g., 1 minute, 15 minutes, 30 minutes, 45 minutes, 1 hour, 2 hours, 3 hours. 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, 10 weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks or longer) the administration of a second therapy (e.g., agent) to a subject having or diagnosed with *Klebsiella pneumonia* ST258 infection or exposed to *Klebsiella pneumonia* ST258 or other *Klebsiella pneumonia* infection.

In some aspects, the second therapy or agent that can be used in combination with drugs used to treat *Klebsiella pneumonia* ST258 infections or other *Klebsiella pneumonia* infections include but are not limited to oral quinolones, imipenem, aztreonam, intravenous aminoglycosides, third generation cephalosporins, piperacillin/tazobactam colistin, tigecycline, gentamicin, ceftazdime-avibactam, and carbapenem.

In some aspects, the combination of therapies (e.g., use of agents, including therapeutic agents) may be more effective than the additive effects of any two or more single therapy (e.g., have a synergistic effect). For example, a synergistic effect of a combination of therapeutic agents frequently permits the use of lower dosages of one or more of the agents and/or less frequent administration of the agents to a cancer patient. The ability to utilize lower dosages of therapeutics and cancer therapies and/or to administer the therapies less frequently reduces the potential for toxicity associated with the administration of the therapies to a subject without reducing the effectiveness of the therapies. In addition, a synergistic effect may result in improved efficacy of therapies in the treatment or prevention of a *Klebsiella pneumonia* ST258 infection or other *Klebsiella pneumonia* infections. Also, a synergistic effect demonstrated by a combination of therapies (e.g., therapeutic agents) may avoid or reduce adverse or unwanted side effects associated with the use of any single therapy.

As used herein, the term "comprising" can include the aspects "consisting of" and "consisting essentially of." "Comprising" can also mean "including but not limited to."

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in some aspects, the increase or promotion can be a 10, 20, 30, 40, 50, 60, 70, 80, 90, 100%, or more, or any amount of promotion in between compared to native or control levels. In some aspects, the increase or promotion is 10-20, 20-30, 30-40, 40-50, 50-60, 60-70, 70-80, 80-90, or 90-100% as compared to native or control levels. In some aspects, the increase or promotion is 0-25, 25-50, 50-75, or 75-100%, or more, such as 200, 300, 500, or 1000% more as compared to native or control levels. In some aspects, the increase or promotion can be greater than 100 percent as compared to native or control levels, such as 100, 150, 200, 250, 300, 350, 400, 450, 500% or more as compared to the native or control levels.

As used herein, the term "determining" can refer to measuring or ascertaining a quantity or an amount or a change in activity. For example, determining the amount of a disclosed polypeptide, protein, gene or antibody in a sample as used herein can refer to the steps that the skilled person would take to measure or ascertain some quantifiable value of the polypeptide protein, gene or antibody in the sample. The art is familiar with the ways to measure an amount of the disclosed polypeptide, proteins, genes or antibodies in a sample.

As used herein, the terms "disease" or "disorder" or "condition" are used interchangeably referring to any alternation in state of the body or of some of the organs, interrupting or disturbing the performance of the functions and/or causing symptoms such as discomfort, dysfunction, distress, or even death to the person afflicted or those in contact with a person. A disease or disorder or condition can also related to a distemper, ailing, ailment, disorder, sickness, illness, complaint, affection. In some aspects, the disease or disorder or condition can be a *Klebsiella pneumonia* ST258 infection or other *Klebsiella pneumonia* infection. In some aspects, the *Klebsiella pneumonia* ST258 or other *Klebsiella pneumonia* strains can express wzi50, wzi154 or wzi29 capsular polysaccharide.

As used herein, the term "24D11" or "monoclonal antibody 24D11" refers to a polypeptide (the terms "polypeptide" and "protein" are used interchangeably herein) or an anti-*Klebsiella pneumoniae* sequence type 258 expressing wzi50, wzi154 or wzi29 capsular polysaccharides or other *Klebsiella pneumonia* strain expressing wzi50, wzi154 or wzi29 capsular polysaccharides, unless otherwise indicated, and, in certain aspects. In some aspects, the term "24D11" or "monoclonal antibody 24D11" refers to a polypeptide having a heavy chain sequence set forth in SEQ ID NOs: 8, 11 and 12, and a light chain sequence set forth in SEQ ID NOs: 4, 9, and 10. In some aspects, the monoclonal antibody 24D11 polypeptide sequence can include or not include the signal sequence.

Abbreviations for the amino acid residues that comprise polypeptides and peptides described herein, and conservative substitutions for these amino acid residues are shown in Table 1 below. A polypeptide that contains one or more conservative amino acid substitutions or a conservatively modified variant of a polypeptide described herein refers to a polypeptide in which the original or naturally occurring amino acids are substituted with other amino acids having similar characteristics, for example, similar charge, hydrophobicity/hydrophilicity, side-chain size, backbone conformation, structure and rigidity, etc. Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity.

TABLE 1

Amino Acid Residues and Examples of Conservative Amino Acid Substitutions

| Original residue Three letter code and Single letter code | Conservative substitution(s) |
|---|---|
| Alanine (Ala) (A) | Gly; Ser |
| Arginine (Arg) (R) | Lys; His |
| Asparagine (Asn) (N) | Gln; His |
| Aspartic Acid (Asp) (D) | Glu; Asn |
| Cysteine (Cys) (C) | Ser; Ala |
| Glutamine (Gln) (Q) | Asn |
| Glutamic Acid (Glu) (E) | Asp; Gln |
| Glycine (Gly) (G) | Ala |
| Histidine (His) (H) | Asn; Gln |
| Isoleucine (Ile) (I) | Leu; Val |
| Leucine (Leu) (L) | Ile; Val |
| Lysine (Lys) (K) | Arg; His |
| Methionine (Met) (M) | Leu; Ile; Tyr |
| Phenylalanine (Phe) (F) | Tyr; Met; Leu |
| Proline (Pro) (P) | Ala |
| Serine (Ser) (S) | Thr |
| Threonine (Thr) (T) | Ser |
| Tryptophan (Trp) (W) | Tyr; Phe |
| Tyrosine (Tyr) (Y) | Trp; Phe |
| Valine (Val) (V) | Ile; Leu |

As used herein, the term "polypeptide" or "peptide" refers to a polymer of amino acids of three or more amino acids in a serial array, linked through peptide bonds. As used herein, the term "amino acid sequence" refers to a list of abbreviations, letters, characters or words representing amino acid residues. "Polypeptides" can be proteins, protein fragments, protein analogs, oligopeptides and the like. The amino acids that comprise the polypeptide may be naturally derived or synthetic. The polypeptide may be purified from a biological sample. For example, a *Klebsiella pneumoniae* sequence type 258 polypeptide or peptide expressing wzi50, wzi154 or wzi29 capsular polysaccharide may be composed of at least 3, 4, 5, 6, 7, 8, 9, 10, 11, 12, 13, 14, 15, 16, 17, 18, 19, 20, 21, 22, 23, 24, or 25 contiguous amino acids. In some aspects, the polypeptide has at least 25, 30, 35, 40, 45, 50, 55, 60, 65, 70, 75, 80, 85, 90, 95, 100, 105, 110, 115, 120, 125, 130, or 135, contiguous amino acids. In some aspects, the *Klebsiella pneumoniae* sequence type 258 polypeptide or peptide expressing wzi50, wzi154 or wzi29 capsular polysaccharide comprises at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 134 contiguous amino acid residues of the amino acid sequence.

By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

As used herein, the term "analog" refers to a polypeptide that possesses a similar or identical function as a reference polypeptide but does not necessarily comprise a similar or identical amino acid sequence of the reference polypeptide, or possess a similar or identical structure of the reference polypeptide. The reference polypeptide may be a fragment of a *Klebsiella pneumoniae* sequence type 258 or other *Klebsiella pneumonia* strain expressing wzi50, wzi154 or wzi29 capsular polysaccharides, or an anti-*Klebsiella pneumoniae* sequence type 258 wzi50, wzi154 or wzi29 capsular polysaccharide antibody, or other anti-*Klebsiella pneumoniae* strain wzi50, wzi154 or wzi29 capsular polysaccharide antibody. A polypeptide that has a similar amino acid sequence with a reference polypeptide refers to a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the reference polypeptide, which can be a *Klebsiella pneumoniae* sequence type 258 or other *Klebsiella pneumoniae* strain expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody as described herein. A polypeptide with similar structure to a reference polypeptide refers to a polypeptide that has a secondary, tertiary, or quaternary structure similar to that of the reference polypeptide, which can be a *Klebsiella pneumoniae* sequence type 258 or other *Klebsiella pneumoniae* strain expressing wzi50, wzi154 or wzi29 capsular polysaccharide or an anti-*Klebsiella pneumoniae* sequence type 258 wzi50, wzi154 or wzi29 capsular polysaccharide antibody or other anti-*Klebsiella* strain *pneumoniae* wzi50, wzi154 or wzi29 capsular polysaccharide antibody described herein. The structure of a polypeptide can determined by methods known to those skilled in the art. including, but not limited to, X-ray crystallography, nuclear magnetic resonance (NMR), and crystallographic electron microscopy.

The term "fragment" can refer to a portion (e.g., at least 5, 10, 25, 50, 100, 125, 150, 200, 250, 300, 350, 400 or 500, etc. amino acids or nucleic acids) of a protein or nucleic acid molecule that is substantially identical to a reference protein or nucleic acid and retains the biological activity of the reference. In some aspects, the fragment or portion retains at least 50%, 75%, 80%, 85%, 90%, 95% or 99% of the biological activity of the reference protein or nucleic acid described herein. Further, a fragment of a referenced peptide can be a continuous or contiguous portion of the referenced polypeptide (e.g., a fragment of a peptide that is ten amino acids long can be any 2-9 contiguous residues within that peptide).

As used herein, the term "variant" when used in relation to a *Klebsiella pneumoniae* sequence type 258 or other *Klebsiella pneumoniae* strain expressing wzi50, wzi154 or wzi29 capsular polysaccharides or an anti-*Klebsiella pneumoniae* sequence type 258 wzi50, wzi154 or wzi29 capsular polysaccharide antibody refers to a polypeptide or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody having one or more amino acid sequence substitutions, deletions, and/or additions as compared to a native or unmodified *Klebsiella pneumoniae* sequence type 258 or other *Klebsiella pneumoniae* strain expressing wzi50, wzi154 or wzi29 capsular polysaccharide sequence or anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody sequence. For example, a *Klebsiella pneumoniae* sequence type 258 or other *Klebsiella pneumoniae* strain expressing wzi50, wzi154 or wzi29 capsular polysaccharide or to an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody refers to a polypeptide or anti-*Klebsiella pneumoniae* sequence type 258 or other anti-*Klebsiella pneumoniae* strain wzi50, wzi154 or wzi29 capsular polysaccharide antibody having one or more amino acid sequence substitutions, deletions, and/or additions as compared to a native or unmodified *Klebsiella pneumoniae* sequence type 258 or other *Klebsiella pneumoniae* strain expressing wzi50, wzi154 or wzi29 capsular polysaccharide sequence or anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody sequence can have about 1 to about 25, about 1 to about 20, about 1 to about 15, about 1 to about 10, or about 1 to about 5 amino acid sequence substitutions, deletions, and/or additions as compared to a native or unmodified *Klebsiella pneumoniae* sequence type 258 or other *Klebsiella pneumoniae* strain expressing wzi50, wzi154 or wzi29 capsular polysaccharide sequence or anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody sequence. A *Klebsiella pneumoniae* sequence type 258 or other *Klebsiella pneumoniae* expressing wzi50, wzi154 or wzi29 capsular polysaccharides variant can result from one or more (such as, for example, about 1 to about 25, about 1 to about 20, about 1 to about 15, about 1 to about 10, or about 1 to about 5) changes to an amino acid sequence of a native *Klebsiella pneumoniae* sequence type 258 or other *Klebsiella pneumoniae* strain expressing wzi50, wzi154 or wzi29 capsular polysaccharides. Also by way of example, a variant of an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody can result from one or more (such as, for example, about 1 to about 25, about 1 to about 20, about 1 to about 15, about 1 to about 10, or about 1 to about 5 changes to an amino acid sequence of a native or previously unmodified anti-*Klebsiella pneumoniae* sequence type 258 wzi50, wzi154 or wzi29 capsular polysaccharide antibody or other anti-*Klebsiella pneumoniae* wzi50, wzi154 or wzi29 capsular polysaccharide antibody. Variants can be naturally occurring, such as allelic or splice variants, or can be artificially constructed. Polypeptide variants can be prepared from the corresponding nucleic acid molecules encoding the variants.

A "variant" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions can include those within the following groups: Ser, Thr, and Cys; Leu, Ile, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, a variant may include selenocysteine (e.g., seleno-L-cysteine) at any position. including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and omithine is basic. Proline may be substituted with hydroxyproline and retain the conformation conferring properties of proline.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g., Met, Ala, Val, Leu, and Ile), among residues with neutral hydrophilic side chains (e.g., Cys, Ser, Thr, Asn and Gln), among residues with acidic side chains (e.g., Asp, Glu), among amino acids with basic side chains (e.g., His, Lys, and Arg), or among residues with aromatic side chains (e.g., Trp, Tyr, and Phe). As known in the art, conservative substitution usually does not cause significant change in the protein conformational structure, and therefore could retain the biological activity of a protein.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (e.g., an "algorithm"). Methods that may be used to calculate the identity of the aligned nucleic acids or polypeptides include those described in Lesk, A. M., ed., 1988, Computational Molecular Biology, New York: Oxford University Press; Smith, D. W., ed., 1993, Biocomputing Informatics and Genome Projects, New York: Academic Press; Griffin, A. M., et al., 1994, Computer Analysis of Sequence Data, Part I, New Jersey: Humana Press; von Heinje, G., 1987, Sequence Analysis in Molecular Biology, New York: Academic Press; Gribskov, M. et al., 1991, Sequence Analysis Primer, New York: M. Stockton Press; and Carillo et al., 1988, Applied Math., 48:1073.

In calculating percent identity, the sequences being compared can be aligned in a way that gives the largest match between the sequences. An example of a computer program that can be used to determine percent identity is the GCG program package, which includes GAP (Devereux et al., 1984, Nucl. Acid Res., 12:387; Genetics Computer Group, University of Wisconsin, Madison. WI), which is a computer algorithm used to align the two polypeptides or polynucleotides to determine their percent sequence identity. The sequences can be aligned for optimal matching of their respective amino acid or nucleotide sequences (the "matched span" as determined by the algorithm). A gap opening penalty (which is calculated as 3 times the average diagonal, wherein the "average diagonal" is the average of the diagonal of the comparison matrix being used, and the "diagonal" is the score or number assigned to each perfect amino acid match by the particular comparison matrix; and a gap extension penalty (which is usually 1/10 times the gap opening penalty), as well as a comparison matrix such as PAM 250 or BLOSUM 62, are used in conjunction with the algorithm. In some aspects, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. USA 89:10915-10919 for the BLOSUM 62 comparison matrix) is also used by the algorithm. Exemplary parameters for determining percent identity for polypeptides or nucleotide sequences using the GAP program include the following: (i) Algorithm: Needleman et al., 1970, J. Mol. Biol., 48:443-453; (ii) Comparison matrix: BLOSUM 62 from Henikoff et al., Id.; (iii) Gap Penalty: 12 (but with no penalty for end gaps); (iv) Gap Length Penalty: 4; and (v) Threshold of Similarity: 0.

Certain alignment schemes for aligning two amino acid sequences can result in matching only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans a representative number of amino acids, for example, at least 50 contiguous amino acids, of the target polypeptide.

Percent (%) amino acid sequence identity with respect to a reference polypeptide sequence is defined as the percentage of amino acid residues in a candidate sequence that is identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill of the practitioner in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the term "derivative" refers to a polypeptide that comprises an amino acid sequence of a reference polypeptide that has been altered by the introduction of amino acid residue substitutions, deletions or additions. The reference polypeptide can be a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody. The term "derivative" as used herein also refers to a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody that has been chemically modified, e.g., by the covalent attachment of any type of molecule to the polypeptide. For example, a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody can be chemically modified, e.g., by glycosylation, acetylation, pegylation, phosphorylation, amidation, derivatization by known protecting/blocking groups, proteolytic cleavage, linkage to a cellular ligand, linkage to a peptide or protein tag molecule, or other protein, etc. The derivatives are modified in a manner that is different from the naturally occurring or starting peptide or polypeptides, either in the type or location of the molecules attached. Derivatives may further include deletion of one or more chemical groups which are naturally present on the peptide or polypeptide. A derivative of a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody may be chemically modified by chemical modifications using techniques known to those of skill in the art, including, but not limited to, specific chemical cleavage, acetylation, formulation, metabolic synthesis by tunicamycin, etc. Further, a derivative of a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody can contain one or more non-classical amino acids. A polypeptide derivative possesses a similar or identical function as the reference polypeptide, which can be a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody described herein, especially an anti-*Klebsiella pneumoniae* sequence type 258 wzi50, wzi154 or wzi29 capsular polysaccharide monoclonal antibody or other anti-*Klebsiella pneumoniae* strain wzi50, wzi154 or wzi29 capsular polysaccharide antibody.

The term "fusion protein" as used herein refers to a polypeptide that includes amino acid sequences of at least two heterologous polypeptides. the term "fusion" when used in relation to a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody refers to the joining, fusing, or coupling of a *Klebsiella pneumoniae* sequence type 258 or other *Klebsiella pneumoniae* expressing wzi50, wzi154 or wzi29 capsular polysaccharides or an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody, variant and/or derivative thereof, with a heterologous peptide or polypeptide. In some aspects, the fusion protein retains the biological activity of the *Klebsiella pneumoniae* sequence type 258 or other *Klebsiella pneumoniae* expressing wzi50, wzi54 or wzi29 capsular polysaccharides or the anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody. In some aspects, the fusion protein includes an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody VH region, VL region, VH CDR (one, two or three VH CDRs), and/or VL CDR (one, two or three VL CDRs) coupled, fused, or joined to a heterologous peptide or polypeptide, wherein the fusion protein binds to an epitope on a *Klebsiella pneumoniae* sequence type 258 or other *Klebsiella pneumoniae* expressing wzi50, wzi154 or wzi29 capsular polysaccharides. Fusion proteins may be prepared via chemical coupling reactions as practiced in the art, or via molecular recombinant technology.

As used herein, the term "composition" refers to a product containing specified component ingredients (e.g., a polypeptide or an antibody provided herein) in, optionally, specified or effective amounts, as well as any desired product which results, directly or indirectly, from the combination or interaction of the specific component ingredients in, optionally, the specified or effective amounts.

As used herein, the term "carrier" includes pharmaceutically acceptable carriers, excipients, diluents, vehicles, or stabilizers that are nontoxic to the cell or mammal being exposed thereto at the dosages and concentrations employed. Often, the physiologically acceptable carrier is an aqueous pH buffered solution. Examples of physiologically acceptable carriers include buffers such as phosphate, citrate, succinate, and other organic acids; antioxidants including ascorbic acid; low molecular weight (e.g., less than about 10 amino acid residues) polypeptides; proteins, such as serum albumin, gelatin, or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose, sucrose, or dextrins; chelating agents such as EDTA; sugar alcohols such as mannitol or sorbitol; salt-forming counterions such as sodium; and/or nonionic surfactants such as TWEENT™, polyethylene glycol (PEG), and PLURONICS™. The term "carrier" can also refer to a diluent, adjuvant (e.g., Freund's adjuvant, complete or incomplete), excipient, or vehicle with which the therapeutic is administered. Such carriers, including pharmaceutical carriers, can be sterile liquids, such as water and oils, including those of petroleum, animal, vegetable or synthetic origin, such as peanut oil, soybean oil, mineral oil, sesame oil and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include, without limitation, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. Compositions can take the form of solutions, suspensions, emulsion, tablets, pills, capsules, powders, sustained-release formulations and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, (1990) Mack Publishing Co., Easton, PA. Compositions, including pharmaceutical compounds, can contain a therapeutically effective amount of an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody in isolated or purified form, together with a suitable amount of carrier so as to provide the form for proper administration to the subject (e.g., patient). The composition or formulation should suit the mode of administration.

As used herein, the term "excipient" refers to an inert substance which is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, for reference, Remington's Pharmaceutical Sciences, (1990) Mack Publishing Co., Easton, PA, which is hereby incorporated by reference in its entirety.

As used herein, the term "pharmaceutically acceptable" or "pharmacologically acceptable" refers to molecular entities, formulations and compositions that do not produce an adverse, allergic, or other untoward or unwanted reaction when administered, as appropriate, to an animal, such as a human. The preparation of a pharmaceutical composition comprising an antibody or additional active ingredient are known to those of skill in the art in light of the present disclosure, as exemplified by Remington's Pharmaceutical Sciences, Id. Moreover, for animal (e.g., human) administration, it will be understood that preparations should meet sterility, pyrogenicity, general safety, and purity standards as required by a regulatory agency of the Federal or a state government, such as the FDA Office of Biological Standards or as listed in the U.S. Pharmacopeia, European Pharmacopeia, or other generally recognized Pharmacopeia for use in animals, and more particularly, in humans.

The term "pharmaceutical formulation" refers to a preparation which is in such form as to permit the biological activity of the active ingredient (e.g., an isolated antibody as described herein, including, but not limited to an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody to be effective, and which contains no additional components that would be are unacceptably toxic to a subject to whom the formulation would be administered. Such a formulation can be sterile, i.e., aseptic or free from all living microorganisms and their spores, etc.

The term "package insert" is used to refer to instructions customarily included in commercial packages of therapeutic products, that contain information about the indications, usage, dosage, administration, contraindications and/or warnings concerning the use of such therapeutic products.

The terms "antibody," "immunoglobulin," and "Ig" are used interchangeably herein in a broad sense and specifically cover, for example, individual anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody, such as the monoclonal antibodies described herein, (including agonist, antagonist, neutralizing antibodies, full length or intact monoclonal antibodies, peptide fragments of antibodies that maintain antigen binding activity); anti-*Klebsiella pneumoniae* sequence type 258 wzi150, wzi154 or wzi29 capsular polysaccharide antibody or other anti-*Klebsiella pneumoniae* strain wzi50, wzi154 or wzi29 capsular polysaccharide antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody, and fragments of anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody, as described herein. An antibody can be human, humanized, chimeric and/or affinity matured. An antibody may be from other species, for example, mouse, rat, rabbit, etc. The term "antibody" is intended to include a polypeptide product of B cells within the immunoglobulin class of polypeptides that is able to bind to a specific molecular antigen. An antibody is typically composed of two identical pairs of polypeptide chains, wherein each pair has one heavy chain (about 50-70 kDa) and one light chain (about 25 kDa); and wherein the amino-terminal portion of the heavy and light chains includes a variable region of about 100 to about 130 or more amino acids and the carboxy-terminal portion of each chain includes a constant region (See, Borrebaeck (ed.), 1995, Antibody Engineering, Second Ed., Oxford University Press.; Kuby, 1997 Immunology, Third Ed., W.H. Freeman and Company, New York). In some aspects, the specific molecular antigen bound by an antibody provided herein includes a *Klebsiella pneumoniae* sequence type 258 or other *Klebsiella pneumoniae* expressing wzi50, wzi154 or wzi29 capsular polysaccharides, a *Klebsiella pneumoniae* sequence type 258 expressing wzi50, wzi154 or wzi29 capsular polysaccharides fragment, or a *Klebsiella pneumoniae* sequence type 258 expressing wzi50, wzi154 or wzi29 capsular polysaccharides epitope. An antibody or a peptide fragment thereof that binds to a *Klebsiella pneumoniae* sequence type 258 or other *Klebsiella pneumoniae* expressing wzi50, wzi154 or wzi29 capsular polysaccharides antigen can be identified, for example, by immunoassays, BIAcore, or other techniques known to those of skill in the art. An antibody or a fragment thereof binds specifically to a *Klebsiella pneumoniae* sequence type 258 or other *Klebsiella pneumoniae* expressing wzi50, wzi154 or wzi29 capsular polysaccharide antigen when it binds to a *Klebsiella pneumoniae* sequence type 258 or other *Klebsiella pneumoniae* expressing wzi50, wzi154 or wzi29 capsular polysaccharides antigen with higher affinity than to any cross-reactive antigen as determined using experimental techniques, such as radioimmunoassays (RIA) and enzyme linked immunosorbent assays (ELISAs). Typically, a specific or selective binding reaction will be at least twice background signal or noise, and more typically more than 5-10 times background signal or noise. See, e.g., Paul, ed., 1989, *Fundamental Immunology Second Edition*, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigen-binding fragments) of any of the above. A binding fragment refers to a portion of an antibody heavy or light chain polypeptide, such as a peptide portion, that retains some or all of the binding activity of the antibody from which the fragment is derived. Non-limiting examples of functional fragments (e.g., antigen-binding fragments) include single-chain Fvs (scFv) (e.g., including monospecific, bispecific, etc.), Fab fragments, F(ab') fragments, $F(ab)_2$ fragments, $F(ab')_2$ fragments, disulfide-linked Fvs (sdFv), Fd fragments, Fv fragments, diabodies, triabodies, tetrabodies and minibodies. In particular, antibodies provided herein include immunoglobulin molecules and immunologically active portions of immunoglobulin molecules, for example, antigen binding domains or molecules that contain an antigen-binding site that binds to a *Klebsiella pneumoniae* sequence type 258 expressing wzi50, wzi154 or wzi29 capsular polysaccharide antigen, (e.g., one or more complementarity determining regions (CDRs) of an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody. Description of such antibody fragments can be found in, for example, Harlow and Lane, 1989, *Antibodies: A Laboratory Manual*, Cold Spring Harbor Laboratory, New York; Myers (ed.), *Molec. Biology and Biotechnology: A Comprehensive Desk Reference*, New York: VCH Publisher, Inc.; Huston et al., 1993, *Cell Biophysics,* 22:189-224; Plückthun and Skerra, 1989, *Meth. Enzymol.,* 178:497-515 and in Day, E. D., 1990, *Advanced Immunochemistry*, Second Ed., Wiley-Liss, Inc., New York, NY. The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. Anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody can be agonistic antibodies or antagonistic antibodies. In some aspects, the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody can be fully human, such as fully human monoclonal anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody. In some aspects, the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody can be humanized, such as humanized monoclonal anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody. In some aspects, the antibodies provided herein can be IgG antibodies, or a class (e.g., human IgG1 or IgG4) or subclass thereof, in particular, IgG1 subclass antibodies.

A four-chain antibody unit is a heterotetrameric glycoprotein composed of two identical light (L) chains and two identical heavy (H) chains. In the case of IgGs, the molecular weight of the four-chain (unreduced) antibody unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. At the N-terminus, each H chain has a variable domain ($V_H$) followed by three constant domains ($C_H$) for each of the α and γ chains and four CH domains for μ and ε isotypes. Each L chain has at the N-terminus, a variable domain ($V_L$) followed by a constant domain ($C_L$) at its carboxy terminus. The $V_L$ domain is aligned with the $V_H$ domain, and the $C_L$ domain is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site, although certain $V_H$ and $V_L$ domains can bind antigen without pairing with a $V_L$ or $V_H$ domain, respectively. The basic structure of immunoglobulin molecules is understood by those having skill in the art. For example, the structure and properties of the different classes of antibodies may be found in Terr, Abba I. et al., 1994*, Basic and Clinical Immunology,* 8th edition, Appleton & Lange, Norwalk, CT, page 71 and Chapter 6.

A "single-chain variable fragment (scFv)" means a protein comprising the variable regions of the heavy and light chains of an antibody. A scFv can be a fusion protein comprising a variable heavy chain, a linker, and a variable light chain. In some aspects, the linker can be a short, flexible fragment that can be about 8 to 20 amino acids in length. For example, (G4S)n can be used (n=1, 2, 3 or 4).

A "fragment antigen-binding fragment (Fab)" is a region of an antibody that binds to antigen. A Fab comprises constant and variable regions from both heavy and light chains.

As used herein, the term "antigen" or "target antigen" is a predetermined molecule to which an antibody can selectively bind. A target antigen can be a polypeptide, peptide, carbohydrate, nucleic acid, lipid, hapten, or other naturally occurring or synthetic compound.

In some aspects, a target antigen can be a small molecule. In some aspects, the target antigen can a polypeptide or peptide. In some aspects, the target antigen can be *Klebsiella pneumoniae* sequence type 258 or other *Klebsiella pneumoniae* expressing wzi50, wzi154 or wzi29 capsular polysaccharides. In some aspects, the target antigen can be *Klebsiella pneumoniae* sequence type 258 or other *Klebsiella pneumoniae* expressing wzi50, wzi154 and wzi29 capsular polysaccharides.

As used herein, the term "antigen binding fragment," "antigen binding domain," "antigen binding region," and similar terms refer to that portion of an antibody which includes the amino acid residues that interact with an antigen and confer on the antibody as binding agent its specificity and affinity for the antigen (e.g., the CDRs of an antibody are antigen binding regions). The antigen binding region can be derived from any animal species, such as rodents (e.g., rabbit, rat, or hamster) and humans. In some aspects, the antigen binding region can be of human origin.

An "isolated" antibody is substantially free of cellular material or other contaminating proteins from the cell or tissue source and/or other contaminant components from which the antibody is derived, or is substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of an antibody that have less than about 30%, 25%, 20%, 15%, 10%, 5%, or 1% (by dry weight) of heterologous protein (also referred to herein as a "contaminating protein"). In some aspects, when the antibody is recombinantly produced, it is substantially free of culture medium, e.g., culture medium represents less than about 20%, 15%, 10%, 5%, or 1% of the volume of the protein preparation. In some aspects, when the antibody is produced by chemical synthesis, it is substantially free of chemical precursors or other chemicals, for example, it is separated from chemical precursors or other chemicals which are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and can include enzymes, hormones, and other proteinaceous or nonproteinaceous solutes. In some aspects, the antibody is purified (1) to greater than or equal to 95% by weight of the antibody, as determined by the Lowry method (Lowry et al., 1951*, J. Bio. Chem.,* 193: 265-275), such as 95%, 96%, 97%, 98%, or 99%, by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody also includes the antibody in situ within recombinant cells since at least one component of the antibody's natural environment will not be present. An isolated antibody is typically prepared by at least one purification step. In some aspects, the antibodies provided herein are isolated.

The term "monoclonal antibody" (monoclonal antibody) refers to an antibody, or population of like antibodies, obtained from a population of substantially homogeneous antibodies, and is not to be construed as requiring production of the antibody by any particular method, including but not limited to, monoclonal antibodies can be made by the hybridoma method first described by Kohler and Milstein (Nature, 256: 495497, 1975), or by recombinant DNA methods.

As used herein, the term "binds" or "binding" refers to an interaction between molecules including, for example, to form a complex. Illustratively, such interactions embrace non-covalent interactions, including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site of an antibody and its epitope on a target (antigen) molecule, such as *Klebsiella pneumoniae* sequence type 258 expressing wzi50, wzi154 or wzi29 capsular polysaccharides, is the affinity of the antibody or functional fragment for that epitope. The ratio of association ($k_{on}$) to dissociation ($k_{off}$) of an antibody to a monovalent antigen ($k_{on}/k_{off}$) is the association constant $K_a$, which is a measure of affinity. The value of K varies for different complexes of antibody and antigen and depends on both $k_{on}$ and $k_{off}$. The association constant $K_a$ for an antibody provided herein may be determined using any method provided herein or any other method known to those skilled in the art. The affinity at one binding site does not always reflect the true strength of the interaction between an antibody and an antigen. When complex antigens containing multiple, repeating antigenic determinants come into contact with antibodies containing multiple binding sites, the interaction of antibody with antigen at one site will increase the probability of an interaction at a second binding site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_d$). Affinity can be measured by common methods known in the art, including those described herein. Low-affinity antibodies generally bind antigen slowly and tend to dissociate readily, while high-affinity antibodies generally bind antigen faster and tend to remain bound longer to antigen. A variety of methods for measuring binding affinity are known in the art, any of which may be used for purposes of the present disclosure. Specific illustrative aspects include the following: In some aspects, the "$K_d$" or "$K_d$ value" is measured by assays known in the art, for example, by a binding assay. The $K_d$ can be measured in a radiolabeled antigen binding assay (RIA), for example, performed with the Fab portion of an antibody of interest and its antigen (Chen, et al., 1999, *J. Mol. Biol.*, 293:865-881). The $K_d$ or $K_d$ value may also be measured by using surface plasmon resonance (SPR) assays (by BIAcore) using, for example, a BIAcore™-2000 or a BIAcore™-3000 (BIAcore, Inc., Piscataway, NJ), or by biolayer interferometry (BLI) using, for example, the OctetQK384 system (ForteBio, Menlo Park, CA), or by quartz crystal microbalance (QCM) technology. An "on-rate" or "rate of association" or "association rate" or "$k_{on}$" can also be determined with the same surface plasmon resonance or biolayer interferometry techniques described above, using, for example, a BIAcore™-2000 or a BIAcore™-3000 (BIAcore, Inc., Piscataway, NJ), or the OctetQK384 system (ForteBio, Menlo Park, CA).

Disclosed herein are isolated antibodies including, but not limited to, anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody, antibodies that specifically bind to *Klebsiella pneumoniae* sequence type 258 or other *Klebsiella pneumoniae* expressing wzi50, wzi154 or wzi29 capsular polysaccharides and antibodies that specifically bind to a *Klebsiella pneumoniae* sequence type 258 or other *Klebsiella pneumoniae* expressing wzi50, wzi154 or wzi29 capsular polysaccharide epitope. The terms "anti-*Klebsiella pneumoniae* sequence type 258 wzi50, wzi154 or wzi29 capsular polysaccharide antibody," "anti-*Klebsiella pneumoniae* sequence type 258 wzi50, wzi154 or wzi29 capsular polysaccharide monoclonal antibody", "monoclonal anti-*Klebsiella pneumoniae* sequence type 258 wzi50, wzi154 or wzi29 capsular polysaccharide", "an antibody that specifically binds to *Klebsiella pneumoniae* sequence type 258 expressing wzi50, wzi154 or wzi29 capsular polysaccharides," or "antibody that is specific for *Klebsiella pneumoniae* sequence type 258 expressing wzi50, wzi154 or wzi29 capsular polysaccharides," "antibodies that specifically bind to a *Klebsiella pneumoniae* sequence type 258 expressing wzi50, wzi154 or wzi29 capsular polysaccharides epitope," "an antibody that selectively binds to *Klebsiella pneumoniae* sequence type 258 expressing wzi50, wzi154 or wzi29 capsular polysaccharides," "antibodies that selectively bind to a *Klebsiella pneumoniae* sequence type 258 expressing wzi50, wzi154 or wzi29 capsular polysaccharides epitope," "an antibody that preferentially binds to *Klebsiella pneumoniae* sequence type 258 expressing wzi150, wzi154 or wzi29 capsular polysaccharides", and analogous terms refer to antibodies capable of binding *Klebsiella pneumoniae* sequence type 258 expressing wzi50, wzi154 or wzi29 capsular polysaccharides, with sufficient affinity and specificity, particularly compared with mutants of *Klebsiella pneumoniae* sequence type 258 expressing wzi50, wzi154 or wzi29 capsular polysaccharides.

By "specifically binds" is meant that an antibody recognizes and physically interacts with its cognate antigen (for example, *Klebsiella pneumoniae* sequence type 258 or other *Klebsiella pneumoniae* expressing wzi50, wzi154 or wzi29 capsular polysaccharides) and does not significantly recognize and interact with other antigens; such an antibody may be a polyclonal antibody or a monoclonal antibody, which are generated by techniques that are well known in the art.

"Preferential binding" of the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody as provided herein may be determined or defined based on the quantification of fluorescence intensity of the antibodies' binding to *Klebsiella pneumoniae* sequence type 258 or other *Klebsiella pneumoniae* expressing wzi50, wzi154 or wzi29 capsular polysaccharides expressed on cells versus an appropriate control, such as binding to variant *Klebsiella pneumoniae* sequence type 258 or other *Klebsiella pneumoniae* expressing wzi50, wzi154 or wzi29 capsular polysaccharides, or to cells expressing a variant form of *Klebsiella pneumoniae* sequence type 258 or other *Klebsiella pneumoniae* expressing wzi50, wzi154 or wzi29 capsular polysaccharides, for example, molecularly engineered cells, cell lines or tumor cell isolates. Preferential binding of anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody as described to a *Klebsiella pneumoniae* sequence type 258 or other *Klebsiella pneumoniae* expressing wzi50, wzi154 or wzi29 capsular polysaccharide-expressing cell is indicated by a measured fluorescent binding intensity (MFI) value, as assessed by cell flow cytometry, of at least 2-fold, at least 3-fold, at least 4-fold, at least 5-fold, at least 6-fold, at least 7-fold, at least 8-fold, at least 10-fold, at least 15-fold, at least 20-fold or greater, as compared with binding of the antibody to a mutant *Klebsiella pneumoniae* sequence type 258 or other *Klebsiella pneumoniae* expressing wzi50, wzi154 or wzi29 capsular polysaccharide polypeptide or a mutant *Klebsiella pneumoniae* sequence type 258 or other *Klebsiella pneumoniae* expressing wz50, wzi154 or wzi29 capsular polysaccharides-expressing cell, wherein the antibody to be assayed is directly or indirectly detectable by a fluorescent label or marker, such as FITC. In some aspects, the antibody to be assayed is directly labeled with a fluorescent marker, such as FITC. In some aspects, an anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody that preferentially or selectively binds *Klebsiella pneumoniae* sequence type 258 or other *Klebsiella pneumoniae* expressing wzi50, wzi154 or wzi29 capsular polysaccharide exhibits an MFI value of from 1.5-fold to 25-fold, or from 2-fold to 20-fold, or from 3-fold to 15-fold, or from 4-fold to 8-fold, or from 2-fold to 10-fold, or from 2-fold to 5-fold or more greater than the MFI value of the same antibody for binding a *Klebsiella pneumoniae* sequence type 258 or other *Klebsiella pneumoniae* expressing wzi50, wzi154 or wzi29 capsular polysaccharide polypeptide or a *Klebsiella pneumoniae* sequence type 258 or other *Klebsiella pneumoniae* expressing wzi50, wzi154 or wzi29 capsular polysaccharide polypeptide variant. Fold-fluorescence intensity values between and equal to all of the foregoing are intended to be included. In some aspects, an antibody that specifically binds to a *Klebsiella pneumoniae* sequence type 258 expressing wzi50, wzi154 or wzi29 capsular polysaccharides antigen does not cross-react with other antigens. In some aspects, an antibody that specifically binds to a *Klebsiella pneumoniae* sequence type 258 or other *Klebsiella pneumoniae* expressing wzi50, wzi154 or wzi29 capsular polysaccharides antigen and inhibits growth in whole blood and promotes phagocytosis. An antibody that specifically binds to a *Klebsiella pneumoniae* sequence type 258 or other *Klebsiella pneumoniae* expressing wzi50, wzi154 or wzi29 capsular polysaccharides antigen can be identified, for example, by immunofluorescence binding assays, immunohistochemistry assay methods, immunoassay methods, Biacore, or other techniques known to those of skill in the art.

In some aspects, an antibody that binds to *Klebsiella pneumoniae* sequence type 258 wzi50, as described herein, has a dissociation constant ($K_d$) of less than or equal to 5 nM, 4 nM, 0.9 nM, 0.8 nM, 0.7 nM, 0.6 nM, 0.5 nM, 0.4 nM, 0.3 nM, 0.2 nM, or 0.1 nM, and/or is greater than or equal to 0.1 nM. In some aspects, an antibody that binds to *Klebsiella pneumoniae* sequence type 258 wzi50, as described herein, has a dissociation constant ($K_d$) of less than or equal to 4.7 nM. Typically a specific or selective reaction will be at least twice background signal or noise and can be more than 10 times background. See, e.g.. Paul, ed., 1989, *Fundamental Immunology Second Edition*, Raven Press, New York at pages 332-336 for a discussion regarding antibody specificity. In some aspects, the extent of binding of the antibody to a "non-target" protein will be less than about 10% of the binding of the antibody to its particular target protein, for example, as determined by fluorescence activated cell sorting (FACS) analysis or radioimmunoprecipitation (RIA).

As used herein, in reference to an antibody, the term "heavy (H) chain" refers to a polypeptide chain of about 50-70 kDa. wherein the amino-terminal portion includes a variable (V) region (also called V domain) of about 115 to 130 or more amino acids and a carboxy-terminal portion that includes a constant (C) region. The constant region (or constant domain) can be one of five distinct types, (e.g., isotypes) referred to as alpha (a), delta (δ), epsilon (ε), gamma (γ) and mu (μ), based on the amino acid sequence of the heavy chain constant region. The distinct heavy chains differ in size: α, δ and γ contain approximately 450 amino acids, while p and a contain approximately 550 amino acids. When combined with a light chain, these distinct types of heavy chains give rise to five well known classes (e.g., isotypes) of antibodies, namely, IgA, IgD, IgE, IgG and IgM, respectively, including four subclasses of IgG, namely IgG1, IgG2, IgG3 and IgG4. An antibody heavy chain can be a human antibody heavy chain.

As used herein in reference to an antibody, the term "light (L) chain" refers to a polypeptide chain of about 25 kDa, wherein the amino-terminal portion includes a variable domain of about 100 to about 110 or more amino acids and a carboxy-terminal portion that includes a constant region. The approximate length of a light chain (both the V and C domains) is 211 to 217 amino acids. There are two distinct types of light chains, referred to as kappa (κ) and lambda (λ), based on the amino acid sequence of the constant domains. Light chain amino acid sequences are well known in the art. An antibody light chain can be a human antibody light chain.

As used herein, the term "variable (V) region" or "variable (V) domain" refers to a portion of the light (L) or heavy (H) chains of an antibody polypeptide that is generally located at the amino-terminus of the L or H chain. The H chain V domain has a length of about 115 to 130 amino acids, while the L chain V domain is about 100 to 110 amino acids in length. The H and L chain V domains are used in the binding and specificity of each particular antibody for its particular antigen. The V domain of the H chain can be referred to as "VH." The V region of the L chain can be referred to as "VL." The term "variable" refers to the fact that certain segments of the V domains differ extensively in sequence among different antibodies. While the V domain mediates antigen binding and defines specificity of a particular antibody for its particular antigen, the variability is not evenly distributed across the 110-amino acid span of antibody V domains. Instead, the V domains consist of less variable (e.g., relatively invariant) stretches called framework regions (FRs) of about 15-30 amino acids separated by shorter regions of greater variability (e.g., extreme variability) called "hypervariable regions" or "complementarity determining regions" (CDRs) that are each about 9-12 amino acids long or 3-17 amino acids long. The V domains of antibody H and L chains each comprise four FRs, largely adopting a § sheet configuration, connected by three hypervariable regions, called, which form loops connecting, and in some cases forming part of, the § sheet structure. The hypervariable regions in each chain are held together in close proximity by the FRs and, with the hypervariable regions from the other chain, contribute to the formation of the antigen-binding site of antibodies (see, e.g., Kabat et al., 1991, Sequences of Proteins of Immunological Interest, 5th Ed. Public Health Service, National Institutes of Health, Bethesda, MD). The C domains are not involved directly in binding an antibody to an antigen, but exhibit various effector functions, such as antibody dependent cellular cytotoxicity (ADCC) and complement dependent cytotoxicity (CDC). The V domains differ extensively in sequence among different antibody classes or types. The variability in sequence is concentrated in the CDRs, which are primarily responsible for the interaction of the antibody with antigen. In some aspects, the variable domain of an antibody is a human or humanized variable domain.

As used herein, the terms "complementarity determining region," "CDR," "hypervariable region," "HVR," and "HV" are used interchangeably. A "CDR" or "complementarity determining region" is a region of hypervariability interspersed within regions that are more conserved, termed "framework regions" (FR). A "CDR" refers to one of three hypervariable regions (H1, H2 or H3) within the non-framework region of the antibody VH β-sheet framework, or to one of three hypervariable regions (L1, L2 or L3) within the non-framework region of the antibody VL β-sheet framework. The term, when used herein, refers to the regions of an antibody V domain that are hypervariable in sequence and/or form structurally defined loops. Generally, antibodies comprise six hypervariable regions: three (H1, H2, H3) in the VH domain and three (L1, L2, L3) in the VL domain. Accordingly, CDRs are typically highly variable sequences interspersed within the framework region sequences of the V domain. "Framework" or "FR" residues are those variable region residues flanking the CDRs. FR residues are present, for example, in chimeric, humanized, human, domain antibodies, diabodies, linear antibodies, and bispecific antibodies.

A number of hypervariable region delineations are in use and are encompassed herein. CDR regions are well known to those skilled in the art and have been defined by, for example, Kabat as the regions of most hypervariability within the antibody V domains (Kabat et al., 1977, J. Biol. Chem., 252:6609-6616; Kabat, 1978, Adv. Prot. Chem., 32:1-75). The Kabat CDRs are based on sequence variability and are the most commonly used (see, e.g., Kabat et al., 1991, Sequences of Proteins of Immunological Interest, 5th Ed. Public Health Service, National Institutes of Health, Bethesda, MD). CDR region sequences also have been defined structurally by Chothia as those residues that are not part of the conserved β-sheet framework, and thus are able to adopt different conformations (Chothia et al., 1987, J. Mol. Biol., 196:901-917). Chothia refers instead to the location of the structural loops. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). Both numbering systems and terminologies are well recognized in the art.

Recently, a universal numbering system has been developed and widely adopted, ImMunoGeneTics (IMGT) Information System® (Lafranc et al., 2003, Dev. Comp. Immunol., 27(1):55-77). IMGT is an integrated information system specializing in immunoglobulins (Ig), T cell receptors (TR) and the major histocompatibility complex (MHC) of human and other vertebrates. Herein, the CDRs are referred to in terms of both the amino acid sequence and the location within the light or heavy chain. As the "location" of the CDRs within the structure of the immunoglobulin V domain is conserved between species and present in structures called loops, by using numbering systems that align variable domain sequences according to structural features, CDR and framework residues and are readily identified. This information can be used in grafting and in the replacement of CDR residues from immunoglobulins of one species into an acceptor framework from, typically, a human antibody. An additional numbering system (AHon) has been developed by Honegger et al., 2001, J. Mol. Biol., 309: 657-670. Correspondence between the numbering system, including, for example, the Kabat numbering and the IMGT unique numbering system, is well known to one skilled in the art (see, e.g., Kabat, Id; Chothia et al., Id.; Martin, 2010, Antibody Engineering, Vol. 2, Chapter 3, Springer Verlag; and Lefranc et al., 1999, Nuc. Acids Res., 27:209-212).

CDR region sequences have also been defined by AbM, Contact and IMGT. The AbM hypervariable regions represent a compromise between the Kabat CDRs and Chothia structural loops, and are used by Oxford Molecular's AbM antibody modeling software (see, e.g., Martin, 2010, Antibody Engineering, Vol. 2, Chapter 3, Springer Verlag). The "contact" hypervariable regions are based on an analysis of the available complex crystal structures. ne residues from each of these hypervariable regions or CDRs are noted below.

The positions of CDRs within a canonical antibody variable region have been determined by comparison of numerous structures (Al-Lazikani et al., 1997, J. Mol. Biol., 273:927-948); Morea et al., 2000, Methods, 20:267-279). Because the number of residues within a hypervariable region varies in different antibodies, additional residues relative to the canonical positions are conventionally numbered with a, b, c and so forth next to the residue number in the canonical variable region numbering scheme (Al-Lazikani et al., Id). Such nomenclature is similarly well known to those skilled in the art.

An "affinity matured" antibody is one with one or more alterations (e.g., amino acid sequence variations, including changes, additions and/or deletions) in one or more HVRs thereof that result in an improvement in the affinity of the antibody for antigen, compared to a parent antibody which does not possess those alteration(s). In some aspects, affinity matured antibodies will have nanomolar or even picomolar affinities for the target antigen, such as *Klebsiella pneumoniae* sequence type 258 wzi50. Affinity matured antibodies are produced by procedures known in the art. For reviews, see Hudson and Souriau, 2003, Nature Medicine, 9:129-134; Hoogenboom, 2005, Nature Biotechnol., 23:1105-1116; Quiroz and Sinclair, 2010, Revista Ingeneria Biomedia, 4: 39-51.

A "chimeric" antibody is one in which a portion of the H and/or L chain, e.g., the V domain, is identical with or homologous to a corresponding amino acid sequence in an antibody derived from a particular species or belonging to a particular antibody class or subclass, while the remainder of the chain(s), e.g., the C domain, is identical with or homologous to corresponding sequences in antibodies derived from another species or belonging to another antibody class or subclass, as well as a fragment of such an antibody, so long as it exhibits the desired biological activity (see, e.g., U.S. Pat. No. 4,816,567; and Morrison et al., 1984, Proc. Natl. Acad. Sci. USA. 81:6851-6855).

The term "humanized antibody" refers to forms of antibodies that contain sequences from non-human (e.g., murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody can comprise all or substantially all of at least one, and in one aspect two, variable domains, in which all or substantially all of the hypervariable loops correspond to those of a non-human immunoglobulin and all or substantially all of the FR regions are those of a human immunoglobulin sequence. The humanized antibody optionally also can comprise at least a portion of an immunoglobulin constant region (Fc), or that of a human immunoglobulin (see, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1: Queen et al. (1989) Proc. Natl. Acad. Sci. USA, Vol 86:10029-10033). The terms "human antibody" and "fully human antibody" are used interchangeably herein and refer to an antibody that possesses an amino acid sequence which corresponds to that of an antibody produced by a human and/or has been made using any of the techniques for making human antibodies as practiced by those skilled in the art. This definition of a human antibody specifically excludes a humanized antibody comprising non-human antigen-binding residues. Human antibodies can be produced using various techniques known in the art, including phage-display libraries (Hoogenboom et al., 1991. J Mol. Biol., 227:381; Marks et al., 1991, J. Mol. Biol., 222:581 and yeast display libraries (Chao et al., 2006, Nature Protocols, 1:755-768). Also available for the preparation of human monoclonal antibodies are methods described in Cole et al., 1985 Monoclonal Antibodies and Cancer Therapy, Alan R Liss, p. 77; Boemer et al., 1991, J. Immunol., 147(1):86-95. See also van Dijk et al., 2001, Curr. Opin. Pharmacol., 5: 368-74. Human antibodies can be prepared by administering an antigen to a transgenic animal whose endogenous Ig loci have been disabled, e.g., a mouse, and that has been genetically modified to harbor human immunoglobulin genes which encode human antibodies, such that human antibodies are generated in response to antigenic challenge (see, e.g., Jakobovits, A., 1995, Curr. Opin. Biotechnol. 6(5):561-566; Brilggemann et al., 1997 Curr. Opin. Biotechnol., 8(4):455-8; and U.S. Pat. Nos. 6,075,181 and 6,150,584 regarding XENOMOUSE™ technology). See also, for example, Li et al., 2006, Proc. Natl. Acad. Sci. USA, 103:3557-3562 regarding human antibodies generated via a human B-cell hybridoma technology. In some aspects, human antibodies comprise a variable region and constant region of human origin. "Fully human" anti-*Klebsiella pneumoniae* sequence type 258 wzi50, wzi154 or wzi29 capsular polysaccharide antibodies, in some aspects, can also encompass antibodies which bind anti-*Klebsiella pneumoniae* sequence type 258 wzi50, wzi154 or wzi29 capsular polysaccharide polypeptides and are encoded by nucleic acid sequences which are naturally occurring somatic variants of human germline immunoglobulin nucleic acid sequence. In some aspects, the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody provided herein are fully human antibodies. The term "fully human antibody" includes antibodies having variable and constant regions corresponding to human germline immunoglobulin sequences as described by Kabat et al. (See Kabat et al., 1991, Sequences of Proteins of Immunological Interest, Fifth Edition, U.S. Department of Health and Human Services, NIH Publication No. 91-3242). The phrase "recombinant human antibody" includes human antibodies that are prepared, expressed, created, or isolated by recombinant means, such as antibodies expressed using a recombinant expression vector transfected into a host cell; antibodies isolated from a recombinant, combinatorial human antibody library; antibodies isolated from an animal (e.g., a mouse or cow) that is transgenic and/or transchromosomal for human immunoglobulin genes (see e.g., Taylor, L. D. et al., 1992, Nucl. Acids Res. 20:6287-6295); or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat et al., 1991, Sequences of Proteins of Immunological Interest, Fifth Edition, U.S. Department of Health and Human Services, NIH Publication No. 91-3242). In some aspects, however, such recombinant human antibodies are subjected to in vitro mutagenesis (or, when an animal transgenic for human Ig sequences is used, in vivo somatic mutagenesis) and, thus, the amino acid sequences of the VH and VL regions of the recombinant antibodies are sequences that, while derived from and related to human germline VH and VL sequences, may not naturally exist within the human antibody germline repertoire in vivo.

As used herein, the term "epitope" is the site(s) or region(s) on the surface of an antigen molecule to which a single antibody molecule binds, such as a localized region on the surface of an antigen, e.g., a *Klebsiella pneumoniae* sequence type 258 or other *Klebsiella pneumoniae* wzi50 polypeptide that is capable of being bound by one or more antigen binding regions of an anti-*Klebsiella pneumonlae* sequence type 258 wzi50, wzi154 or wzi29 capsular polysaccharide antibody or other anti-*Klebsiella pneumoniae* strain wzi50, wzi154 or wzi29 capsular polysaccharide antibody. An epitope can be immunogenic and capable of eliciting an immune response in an animal. Epitopes need not necessarily be immunogenic. Epitopes often consist of chemically active surface groupings of molecules such as amino acids or sugar side chains and have specific three dimensional structural characteristics as well as specific charge characteristics. An epitope can be a linear epitope and a conformational epitope. A region of a polypeptide contributing to an epitope can be contiguous amino acids of the polypeptide, forming a linear epitope, or the epitope can be formed from two or more non-contiguous amino acids or regions of the polypeptide, typically called a conformational epitope. the epitope may or may not be a three-dimensional surface feature of the antigen. In some aspects, a *Klebsiella pneumoniae* sequence type 258 wzi50 epitope is a three-dimensional surface feature of a *Klebsiella pneumoniae* sequence type 258 wzi50 polypeptide. In some aspects, a *Klebsiella pneumoniae* sequence type 258 wzi50 epitope is linear feature of a *Klebsiella pneumoniae* sequence type 258 wzi50 polypeptide.

An antibody binds "an epitope" or "essentially the same epitope" or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies to antigen is measured using a detectable signal, e.g., radioactive, fluorescent or enzyme labels.

The term "compete" when used in the context of anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody that compete for the same epitope or binding site on a *Klebsiella pneumoniae* sequence type 258 or other *Klebsiella pneumoniae* wzi50 target protein or peptide thereof means competition as determined by an assay in which the antibody under study, or binding fragment thereof, prevents, blocks, or inhibits the specific binding of a reference molecule (e.g., a reference ligand, or reference antigen binding protein, such as a reference antibody) to a common antigen (e.g., *Klebsiella pneumoniae* sequence type 258 or other *Klebsiella pneumoniae* expressing wzi50 or a fragment thereof). Numerous types of competitive binding assays can be used to determine if a test antibody competes with a reference antibody for binding to *Klebsiella pneumoniae* sequence type 258 or other *Klebsiella pneumonia* expressing wzi50.

Examples of assays that can be employed include solid phase direct or indirect radioimmunoassay (RIA); solid phase direct or indirect enzyme immunoassay (EIA); sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619); solid phase direct labeled assay; solid phase direct labeled sandwich assay (see, e.g.. Harlow and Lane, 1988, Antibodies, A Laboratory Manual, Cold Spring Harbor Press); solid phase direct label RIA using labeled iodine (1125 label) (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of a purified antigen (e.g., *Klebsiella pneumoniae* sequence type 258 or other *Klebsiella pneumoniae* expressing wzi50) bound to a solid surface, or cells bearing either of an unlabeled test antigen binding protein (e.g., test anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody or a labeled reference antigen binding protein (e.g., reference anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody. Competitive inhibition can be measured by determining the amount of label bound to the solid surface or cells in the presence of a known amount of the test antigen binding protein. Usually the test antigen binding protein is present in excess. Antibodies identified by competition assay (competing antibodies) include antibodies binding to the same epitope as the reference antibody and/or antibodies binding to an adjacent epitope sufficiently proximal to the epitope bound by the reference antibody causing steric hindrance to occur. Additional details regarding methods for determining competitive binding are described herein. Usually, when a competing antibody protein is present in excess, it will inhibit specific binding of a reference antibody to a common antigen by at least 15%, or at least 20%, for example, without limitation, 25%, 30%, 35%, 40%, 45%, 50%, 55%, 60%, 65%, 70% or 75% or greater, as well as percent amounts between the amounts stated. In some aspects, binding can be inhibited by at least 80%, 85%, 90%, 95%, 96% or 97%, 98%, 99% or more.

As used herein, the term "blocking" antibody or an "antagonist" antibody refers to an antibody that prevents, inhibits, blocks, or reduces biological or functional activity of the antigen to which it binds. Blocking antibodies or antagonist antibodies can substantially or completely prevent, inhibit, block, or reduce the biological activity or function of the antigen. For example, a blocking anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody can prevent, inhibit, block, or reduce *Klebsiella pneumoniae* sequence type 258 or other *Klebsiella pneumoniae* wzi50, wzi154 or wzi29 capsular polysaccharide growth in whole human blood, thus preventing, blocking, inhibiting, or reducing *Klebsiella pneumoniae* sequence type 258 or other *Klebsiella pneumoniae* wzi50 infection. In some aspects, the preventing, blocking, inhibiting, or reducing of *Klebsiella pneumoniae* sequence type 258 or other *Klebsiella pneumoniae* infection can be via promoting phagocytosis. The terms block, inhibit, and neutralize are used interchangeably herein and refer to the ability of the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibody to prevent or otherwise disrupt or reduce *Klebsiella pneumoniae* sequence type 258 or other *Klebsiella pneumoniae* growth in blood.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Capsular polysaccharides (CPS) have been shown to be a useful immunotherapy target against infections by Carbapenem-resistant *Klebsiella pneumoniae* (CR-Kp) strain sequence type ST258, which is the most prevalent CR-Kp strain in the United States. However, the most pressing challenge of anti-capsular antibody endeavors remains maximizing coverage against CR-Kps' heterogeneous CPS serotypes, which are defined by wzi typing. ST258 CR-Kp strains express different wzi types (wzi 50, 29, 154), however, so far the wzi154 strains have been successfully targeted by monoclonal antibodies (mAb). wzi50-type capsular polysaccharide is an immunotherapy candidate because it elicits cross protective antibodies in infected patients. Therefore, a murine mAb 24D11 (IgG2b isotype)

was developed by vaccinating mice with purified wzi50 type CPS. Cross-reactivity and protective efficacy of mAb 24D11 were confirmed against CR-Kp of 3 prevalent CPS types (wzi29, wzi154, and wzi50) using both in vitro and in vivo infection models. mAb 24D11 induced complement-mediated and complement-independent opsonophagocytosis of the tested CR-Kp strains. In addition, mAb 24D11 induced significant killing in whole-blood derived from healthy donors of both wzi50 as well as discordant CR-Kp strains. Using a murine intratracheal infection model, it was also demonstrated that mAb 24D11 reduced lung burden and dissemination of CR-Kp expressing different wzi-types pre but also if given 4 hours post infection. Additionally, the protective efficacy of mAb 24D11 remained effective in neutropenic mice. Lastly, combination of mAb 24D11 with anti-wzi154 mAb 17H12 did not further enhance potent protection against clade 2 CR-Kp (wzi154) infection. This the monoclonal antibody described herein exhibits cross-protective efficacy against clade 1 and clade 2 ST258 CR-Kp strains. It overcomes a major barrier to successfully target wzi29, a major CPS expressed by ST258 CR-Kp including that which cause the CR-Kp outbreak at the NIH in 2009. The finding that 24D11 also exhibits potent protective efficacy against wzi154 expressing CR-Kp strains as a monotherapy and as a lead agent for CR-Kp infected patients.

Compositions

Anti-*Klebsiella pneumoniae* sequence type 258 wzi50. wzi154 or wzi29 capsular polysaccharide antibodies or other anti-*Klebsiella pneumoniae* strain wzi50, wzi154 or wzi29 capsular polysaccharide antibodies. Disclosed herein are isolated antibodies, including, but not limited to, anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies or binding fragments thereof. Disclosed herein are anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies or binding fragments thereof that bind to *Klebsiella pneumoniae* sequence type 258 or other *Klebsiella pneumoniae* expressing wzi50, wzi154 or wzi29 capsular polysaccharide. Disclosed herein are anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies or binding fragments thereof that bind to *Klebsiella pneumoniae* sequence type 258 or other *Klebsiella pneumoniae* wzi50, wzi154 or wzi29 capsular polysaccharide and inhibit growth of *Klebsiella pneumoniae* sequence type 258 or other *Klebsiella pneumoniae* and/or promote phagocytosis. Disclosed herein are anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies or binding fragments thereof useful in treating and preventing *Klebsiella pneumonia* (e.g., ST258 or ESBL) infections. Also disclosed herein are anti-*Klebsiella pneumoniae* sequence type 258 wzi50, wzi154 or wzi29 capsular polysaccharide antibodies or other anti-*Klebsiella pneumonia* e strain wzi50, wzi154 or wzi29 capsular polysaccharide antibodies or binding fragments thereof useful in inhibiting, treating or preventing *Klebsiella pneumonia* ST258 or other *Klebsiella pneumoniae* infections, inducing complement-mediated or complement-independent opsonophagocytosis, or inducing an immune response, reducing lung burden or dissemination of *Klebsiella pneumonia* ST258 or other *Klebsiella pneumoniae*, reducing lung, liver or spleen bacterial load of a *Klebsiella pneumonia* ST258 or other *Klebsiella pneumoniae* infection, or increasing opsonophagocytic uptake.

The anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies disclosed herein can be of the IgG, IgM, IgA, IgD, and IgE Ig classes, as well as polypeptides comprising one or more antibody CDR domains that retain antigen binding activity. Illustratively, the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies may be chimeric, affinity matured, humanized, or human antibodies. In some aspects, the anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies can be monoclonal antibodies. In some aspects, the monoclonal anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody can be a humanized antibody. By known means and as described herein, polyclonal or monoclonal antibodies, antibody fragments, binding domains and CDRs (including engineered forms of any of the foregoing) may be created that are specific for to *Klebsiella pneumoniae* sequence type 258 or other *Klebsiella pneumoniae* expressing wzi50, wzi154 or wzi29 capsular polysaccharide antigen, one or more of its respective epitopes, or conjugates of any of the foregoing, whether such antigens or epitopes are isolated from natural sources or are synthetic derivatives or variants of the natural protein.

Also disclosed herein are compositions comprising the disclosed isolated antibodies, including, but not limited to anti-*Klebsiella pneumoniae* sequence type 258 wzi50, wzi154 or wzi29 capsular polysaccharide antibodies or other anti-*Klebsiella pneumoniae* strain wzi50, wzi154 or wzi29 capsular polysaccharide antibodies. In some aspects, the antibodies disclosed herein can be isolated antibodies. Examples of the CDR sequences and heavy or light chain variable region sequences of anti-*Klebsiella pneumoniae* sequence type 258 wzi50, wzi154 or wzi29 capsular polysaccharide or other anti-*Klebsiella pneumoniae* strain wzi50, wzi154 or wzi29 capsular polysaccharide antibodies are shown in Table 3.

Disclosed herein are isolated antibodies comprising a light chain variable region and a heavy chain variable region. In some aspects, the light chain variable region can comprise a complementarity determining region light chain 1 (CDRL1) amino acid sequence of SEQ ID NO: 1; a complementarity determining region light chain 2 (CDRL2) amino acid sequence of SEQ ID NO: 2; and a complementarity determining region light chain 3 (CDRL3) amino acid sequence of SEQ ID NO: 3. In some aspects, the heavy chain variable region can comprise a complementarity determining region heavy chain 1 (CDRH1) amino acid sequence of SEQ ID NO: 5; a complementarity determining region heavy chain 2 (CDRH2) amino acid sequence of SEQ ID NO: 6; and a complementarity determining region heavy chain 3 (CDRH3) amino acid sequence of SEQ ID NO: 7.

Also disclosed herein, are isolated antibodies comprising a light chain variable region amino acid sequence of SEQ ID NO: 4 and a heavy chain variable region amino acid sequence of SEQ ID NO: 8.

In some aspects, any of the antibodies disclosed herein can comprise a light chain variable region amino acid sequence comprising SEQ ID NO: 4. In some aspects, any of the antibodies disclosed herein can comprise a heavy chain variable region amino acid sequence comprising SEQ ID NO: 8. In some aspects, a light chain variable region has an amino acid sequence that is at least 90% identical to amino acid sequence SEQ ID NO: 4. In some aspects, a heavy chain variable region has an amino acid sequence that is at least 90% identical to amino acid sequence SEQ ID NO: 8.

Disclosed herein are isolated antibodies comprising a light chain variable region and a heavy chain variable region, wherein the light chain variable region comprises the amino acid sequence of SEQ ID NO: 4. Also disclosed herein are isolated antibodies comprising a light chain variable region and a heavy chain variable region, wherein the heavy chain variable region comprises the amino acid sequence of SEQ ID NO: 8.

Disclosed herein are isolated antibodies comprising a light chain variable region and a heavy chain variable region, wherein the light chain variable region comprises the amino acid sequence of SEQ ID NO: 4. In some aspects, a light chain variable region has an amino acid sequence that is at least 90% identical to amino acid sequence SEQ ID NO: 4.

Also disclosed herein are isolated antibodies comprising a light chain variable region and a heavy chain variable region, wherein the heavy chain variable region comprises the amino acid sequence of SEQ ID NO: 8. In some aspects, a heavy chain variable region has an amino acid sequence that is at least 90% identical to amino acid sequence SEQ ID NO: 8.

Disclosed herein are isolated antibodies comprising a light chain variable region and a heavy chain variable region, wherein the light chain variable region comprises a complementarity determining region light chain 1 (CDRL1) amino acid sequence of SEQ ID NO: 1; a determining region light chain 2 (CDRL2) amino acid sequence of SEQ ID NO: 2; and a determining region light chain 3 (CDRL3) amino acid sequence of SEQ ID NO: 3; and wherein the heavy chain variable region comprises a complementarity determining region heavy chain 1 (CDRH1) amino acid sequence of SEQ ID NO: 5; a complementarity determining region heavy chain 2 (CDRH2) amino acid sequence of SEQ ID NO: 5; and a complementarity determining region heavy chain 3 (CDRH3) amino acid sequence of SEQ ID NO: 6, wherein one or more of the CDRL1, CDRL2, CDRL3, CDRH1, CDRH2, or CDRH3 comprise 1, 2, 3, 4, or 5 conservative amino acid substitutions.

Disclosed herein are isolated antibodies comprising a light chain variable region amino acid sequence of SEQ ID NO: 4 and a heavy chain variable region amino acid sequence of SEQ ID NO: 8, wherein the isolated antibody comprises 1, 2, 3, 4, or 5 conservative amino acid substitutions in the light or heavy chain variable region amino acid sequences.

TABLE 2

Exemplary Amino Acid Sequences of anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody.

| SEQ ID NO: | Sequence | Description |
|---|---|---|
| 1 | KSSQSLLYSNGKTYLN | CDRL1, IMGT |
| 2 | LVSKLDS | CDRL2, IMGT |
| 3 | VQGTHFPQT | CDRL3, IMGT |
| 4 | DVVMTQTPLTLSVTIGQPASISCKSSQS LLYSNGKTYLNWLLQRPGQSPKRLIYL VSKLDSGVPDRFTGSGSGTDFTLKISRV EAEDLGVYYCVQGTHFPQTFGGGTKL EIK | Kappa Light Chain Variable Domain, IMGT |
| 5 | NYVIH | CDRH1, IMGT |
| 6 | YINPYSDGTKYNEKFKD | CDRH2, IMGT |
| 7 | GGPYYDYGGYTMDY | CDRH3, IMGT |
| 8 | EVQLQQSGPELVKPGASVKMSCKAS GYTFTNYVIHWVKQKPGQGLEWIGY INPYSDGTKYNEKFKDKATLTSDKSS STAYMELISLTSEDSAVYYCARGGPY YDYGGYTMDYWGQGTSVTVSS | Heavy Chain Variable Domain, IMGT |
| 9 | MSPAQFLFLLVLWIQETNGDVVMTQT PLTLSVTIGQPASISCKSSQSLLYSNGK TYLNWLLQRPGQSPKRLIYLVSKLDS GVPDRFTGSGSGTDFTLKISRVEAEDL GVYYCVQGTHFPQTFGGGTKLEIKRA DAAPTVSIFPPSSEQLTSGGASVVCFL NNFYPKDINVKWKIDGSERQNGVLN SWTDQDSKDSTYSMSSTLTLTKDEY ERHNSYTCEATHKTSTSPIVKSFNRNEC | Light chain with signal peptide underlined |
| 10 | DVVMTQTPLTLSVTIGQPASISCKSSQ SLLYSNGKTYLNWLLQRPGQSPKRLI YLVSKLDSGVPDRFTGSGSGTDFTLK ISRVEAEDLGVYYCVQGTHFPQTFGG GTKLEIKRADAAPTVSIFPPSSEQLTSG GASVVCFLNNFYPKDINVKWKIDGSE RQNGVLNSWTDQDSKDSTYSMSSTLT LTKDEYERHNSYTCEATHKTSTSPIVK SFNRNEC | Light chain without signal peptide |
| 11 | MEWSWIFLFLLSGTAGVHSEVQLQQ SGPELVKPGASVKMSCKASGYTFTN YVIHWVKQKPGQGLEWIGYINPYSD GTKYNEKFKDKATLTSDKSSSTAYM ELISLTSEDSAVYYCARGGPYYDYGG YTMDYWGQGTSVTVSSAKTTPPSVY PLAPGCGDTTGSSVTLGCLVKGYFPE SVTVTWNSGSLSSSVHTFPALLQSGL YTMSSSVTVPSSTWPSQTVTCSVAHP ASSTTVDKKLEPSGPISTINPCPPCKEC HKCPAPNLEGGPSVFIFPPNIKDVLMIS LTPKVTCVVVDVSEDDPDVQISWFVN NVEVHTAQTQTHREDYNSTIRVVSTL PIQHQDWMSGKEFKCKVNNKDLPSPIE RTISKIKGLVRAPQVYILPPPAEQLSRK DVSLTCLVVGFNPGDISVEWTSNGHTE ENYKDTAPVLDSDGSYFIYSKLNMKTS | Heavy chain with signal peptide underlined |

TABLE 2-continued

Exemplary Amino Acid Sequences of anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody.

| SEQ ID NO: | Sequence | Description |
|---|---|---|
| | KWEKTDSFSCNVRHEGLKNYYLKKTIS<br>RSPGK | |
| 12 | EVQLQQSGPELVKPGASVKMSCKASG<br>YTFTNYVIHWVKQKPGQGLEWIGYIN<br>PYSDGTKYNEKFKDKATLTSDKSSST<br>AYMELISLTSEDSAVYYCARGGPYYD<br>YGGYTMDYWGQGTSVTVSSAKTTPP<br>SVYPLAPGCGDTTGSSVTLGCLVKGY<br>FPESVTVTWNSGSLSSSVHTFPALLQSGL<br>YTMSSSVTVPSSTWPSQTVTCSVAHP<br>ASSTTVDKKLEPSGPISTINPCPPCKEC<br>HKCPAPNLEGGPSVFIFPPNIKDVLMIS<br>LTPKVTCVVVDVSEDDPDVQISWFVN<br>NVEVHTAQTQTHREDYNSTIRVVSTL<br>PIQHQDWMSGKEFKCKVNNKDLPSPIE<br>RTISKIKGLVRAPQVYILPPPAEQLSRK<br>DVSLTCLVVGFNPGDISVEWTSNGHTE<br>ENYKDTAPVLDSDGSYFIYSKLNMKTS<br>KWEKTDSFSCNVRHEGLKNYYLKKTIS<br>RSPGK | Heavy chain without signal peptide |

TABLE 3

Exemplary Nucleic Acid Sequences of anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody.

| SEQ ID NO: | Sequence | Description |
|---|---|---|
| 13 | AAGTCAAGTCAGAGCCTCTTATATAGTAATG<br>GAAAAACCTATTTGAAT | CDRL1, IMGT |
| 14 | CTGGTGTCTAAACTGGACTCT | CDRL2, IMGT |
| 15 | GTGCAAGGTACACATTTTCCTCAGACG | CDRL3, IMGT |
| 16 | ATGAGTCCTGCCCAGTTCCTGTTTCTGTTAGT<br>GCTCTGGATTCAGGAAACCAACGGTGATGTT<br>GTGATGACCCAGACTCCACTCACTTTGTCGG<br>TTACCATTGGACAACCAGCCTCTATCTCTTG<br>CAAGTCAAGTCAGAGCCTCTTATATAGTAAT<br>GGAAAAACCTATTTGAATTGGTTATTACAGA<br>GGCCAGGCCAGTCTCCAAAGCGCCTAATCTA<br>TCTGGTGTCTAAACTGGACTCTGGAGTCCCTG<br>ACAGGTTCACTGGCAGTGGATCAGGAACAGA<br>TTTTACACTGAAAATCAGCAGAGTGGAGGCT<br>GAGGATTTGGGAGTTTATTACTGCGTGCAAG<br>GTACACATTTTCCTCAGACGTTCGGTGGAGG<br>CACCAAGCTGGAAATCAAACGGGCTGATGCT<br>GCACCAACTGTATCCATCTTCCCACCATCCAG<br>TGAGCAGTTAACATCTGGAGGTGCCTCAGTC<br>GTGTGCTTCTTGAACAACTTCTACCCCAAAGA<br>CATCAATGTCAAGTGGAAGATTGATGGCAGT<br>GAACGACAAAATGGCGTCCTGAACAGTTGGA<br>CTGATCAGGACAGCAAAGACAGCACCTACAG<br>CATGAGCAGCACCCTCACGTTGACCAAGGAC<br>GAGTATGAACGACATAACAGCTATACCTGTG | Kappa Light Chain Variable Domain, IMGT; signal sequence is underlined; and the stop codon is in bold |

TABLE 3-continued

Exemplary Nucleic Acid Sequences of anti-*Klebsiella pneumoniae* sequence type 258 wzi50, wzi154 or wzi29 capsular polysaccharide antibody or other anti-*Klebsiella pneumoniae* strain wzi50, wzi154 or wzi29 capsular polysaccharide antibody.

| SEQ ID NO: | Sequence | Description |
|---|---|---|
| | AGGCCACTCACAAGACATCAACTTCACCCAT<br>TGTCAAGAGCTTCAACAGGAATGAGTGT**TAG** | |
| 17 | AACTATGTTATACAC | CDRH1, IMGT |
| 18 | TATATTAATCCTTACAGTGATGGTACTAAGT<br>ACAATGAGAAGTTCAAAGAC | CDRH2, IMGT |
| 19 | GGGGGGCCCTACTATGATTACGGAGGGTAT<br>ACTATGGACTAC | CDRH3, IMGT |
| 20 | ATGGAATGGAGTTGGATATTTCTCTTTCTCC<br>TGTCAGGAACTGCAGGTGTCCACTCTGAGG<br>TCCAGCTGCAGCAGTCTGGACCTGAGCTGG<br>TAAAGCCTGGGGCTTCAGTGAAGATGTCCT<br>GCAAGGCTTCTGGATACACATTCACTAACT<br>ATGTTATACACTGGGTGAAGCAGAAGCCT<br>GGGCAGGGCCTTGAGTGGATTGGATATATT<br>AATCCTTACAGTGATGGTACTAAGTACAAT<br>GAGAAGTTCAAAGACAAGGCCACACTGACT<br>TCAGACAAATCCTCCAGCACAGCCTACATGG<br>AGCTCATCAGCCTGACCTCTGAGGACTCTGC<br>GGTCTATTACTGTGCAAGAGGGGGGCCCTAC<br>TATGATTACGGAGGGTATACTATGGACTACT<br>GGGGTCAAGGAACCTCAGTCACCGTCTCCTC<br>AGCCAAAACAACACCCCCATCAGTCTATCCA<br>CTGGCCCCTGGGTGTGGAGATACAACTGGTT<br>CCTCCGTGACTCTGGGATGCCTGGTCAAGGG<br>CTACTTCCCTGAGTCAGTGACTGTGACTTGG<br>AACTCTGGATCCCTGTCCAGCAGTGTGCACA<br>CCTTCCCAGCTCTCCTGCAGTCTGGACTCTAC<br>ACTATGAGCAGCTCAGTGACTGTCCCCTCCA<br>GCACCTGGCCAAGTCAGACCGTCACCTGCAG<br>CGTTGCTCACCCAGCCAGCAGCACCACGGTG<br>GACAAAAAACTTGAGCCCAGCGGGCCCATTT<br>CAACAATCAACCCCTGTCCTCCATGCAAGGA<br>GTGTCACAAATGCCCAGCTCCTAACCTCGAG<br>GGTGGACCATCCGTCTTCATCTTCCCTCCAAA<br>TATCAAGGATGTACTCATGATCTCCCTGACAC<br>CCAAGGTCACGTGTGTGGTGGTGGATGTGAG<br>CGAGGATGACCCAGACGTCCAGATCAGCTGG<br>TTTGTGAACAACGTGGAAGTACACACAGCTC<br>AGACACAAACCCATAGAGAGGATTACAACAG<br>TACTATCCGGGTGGTCAGCACCCTCCCCATCC<br>AGCACCAGGACTGGATGAGTGGCAAGGAGTT<br>CAAATGCAAGGTCAACAACAAAGACCTCCCA<br>TCACCCATCGAGAGAACCATCTCAAAAATTAA<br>AGGGCTAGTCAGAGCTCCACAAGTATACATCT<br>TGCCGCCACCAGCAGAGCAGTTGTCCAGGAAA<br>GATGTCAGTCTCACTTGCCTGGTCGTGGGCTTC<br>AACCCTGGAGACATCAGTGTGGAGTGGACCAG<br>CAATGGGCATACAGAGGAGAACTACAAGGACA<br>CCGCACCAGTCCTGGACTCTGACGGTTCTTACTT<br>CATATATAGCAAGCTCAATATGAAAACAAGCAA<br>GTGGGAGAAAACAGATTCCTTCTCATGCAACGT<br>GAGACACGAGGGTCTGAAAAATTACTACCTGAA<br>GAAGACCATCTCCCGGTCTCCGGGTAAA**TGA** | Heavy Chain Variable Domain, IMGT; signal sequence is underlined; and the stop codon is in bold |

The CDRs disclosed herein may also include variants. Generally, the amino acid identity between individual variant CDRs is at least 90%, 91%, 92%, 93%, 94%, 95%, 96%, 97%, 98%, 99%, or 100%. Thus, a "variant CDR" is one with the specified identity to the parent or reference CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR. For example, a "variant CDR" can be a sequence that contains 1, 2, 3, 4 or 5 amino acid changes as compared to the parent or reference CDR of the invention, and shares or improves biological function, specificity and/or activity of the parent CDR.

In some aspects, any of CDR sequences disclosed herein can include a single amino acid change as compared to the parent or reference CDR In some aspects, any of the CDR sequences disclosed herein can include at least two amino acid changes as compared to the parent or reference CDR In some aspects, the amino acid change can be a change from a cysteine residue to another amino acid. In some aspects, the amino acid change can be a change from a glycine residue to another amino acid. The amino acid identity between individual variant CDRs can be at least 60%, 65%, 70%, 75%, 80%, 85%, 90%, 91%, 92%, 93%, 94%, 95%, 96%, 97%, 98%, 99% or 100%. Thus, a "variant CDR" can be one with the specified identity to the parent CDR of the invention, and shares biological function, including, but not limited to, at least 800%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR For example, the parent CDR sequence can be one or more of SEQ ID NOs: 1, 2, 3, 5, 6, and/or 7. The variant CDR sequence can be at least 60%, 65%, 70%, 75%, 80%, 85%, 90%, 91%, 92%, 93%, 94%, 95%, 96%, 97%, 98%, 99% or 100% identical to any one of SEQ ID NOs: 1, 2, 3, 5, 6, and/or 7. The variant CDR sequence can also share at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

As discussed herein, minor variations in the amino acid sequences of any of the antibodies disclosed herein are contemplated as being encompassed by the instant disclosure, providing that the variations in the amino acid sequence maintains at least 75%, more preferably at least 80%, 90%, 95%, and most preferably 99% sequence identity to the parent sequence. In some aspects, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, an isolated replacement of a leucine with an isoleucine or valine, an aspartate with a glutamate, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are known to one of ordinary skill in the art.

In some aspects, amino acid substitutions can be those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. In some aspects, single or multiple amino acid substitutions (preferably conservative amino acid substitutions) can be made in the non-CDR sequence of the heavy chain, the light chain or both. In some aspects, one or more amino acid substitutions can be made in one or more of the CDR sequences of the heavy chain, the light chain or both.

Many methods have been developed for chemical labeling and enhancement of the properties of antibodies and their common fragments, including the Fab and F(ab')2 fragments. Somewhat selective reduction of some antibody disulfide bonds has been previously achieved, yielding antibodies and antibody fragments that can be labeled at defined sites, enhancing their utility and properties. Selective reduction of the two hinge disulfide bonds present in F(ab')2 fragments using mild reduction has been useful. In some aspects, cysteine and methionine can be susceptible to rapid oxidation, which can negatively influence the cleavage of protecting groups during synthesis and the subsequent peptide purification. In some instances, cysteine residues in peptides used for antibody production can affect the avidity of the antibody, because free cysteines are uncommon in vivo and therefore may not be recognized by the native peptide structure. In some aspects, the disclosed antibodies and fragments thereof comprise a sequence where a cysteine reside outside of the CDR (e.g. in the non-CDR sequence of the heavy chain, the light chain or both) is substituted. In some aspects, cysteine can be replaced with serine and methionine replaced with norleucine (Nle). Multiple cysteines on a peptide or in one of the disclosed antibodies or fragments thereof may be susceptible to forming disulfide linkages unless a reducing agent such as dithiothreitol (DTT) is added to the buffer or the cysteines can be replaced with serine residues.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities as described herein.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions. deletions, insertions, or any combination thereof may be used to arrive at a final derivative or variant. Generally, these changes are done on a few amino acids to minimize the alteration of the molecule, particularly the immunogenicity and specificity of the antigen binding protein. However, larger changes may be tolerated in certain circumstances.

By "Fab" or "Fab region" as used herein is meant the polypeptide that comprises the VH, CH1, VL, and CL immunoglobulin domains. Fab may refer to this region in isolation, or this region in the context of a full-length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

Disclosed herein are isolated antibodies comprising a light chain variable region, wherein the light chain variable region comprises a variant complementarity determining region light chain 1 (CDRL1), positions 24-39 of SEQ ID NO: 4. In some aspects, the variant CDRL1 can comprise one or two amino acid substitutions when compared to positions 24-39 of SEQ ID NO: 4. Also, disclosed herein are isolated antibodies comprising a light chain variable region, wherein the light chain variable region comprises a variant CDRL2, positions 55-64 of SEQ ID NO: 4. In some aspects, the variant CDRL2 can comprise one or two amino acid substitutions when compared to positions 55-64 of SEQ ID NO: 4. Further disclosed herein are isolated antibodies comprising a light chain variable region, wherein the light chain variable region comprises a variant CDRL3, 94-102 positions of SEQ ID NO: 4. In some aspects, the variant CDRL3 can comprise one or two amino acid substitutions when compared to positions 94-102 of SEQ ID NO: 4.

Disclosed herein are isolated antibodies comprising a heavy chain variable region, wherein the heavy chain variable region comprises a variant complementarity determining region heavy chain 1 (CDRH1), positions 31-35 of SEQ ID NO: 8. In some aspects, the variant CDRH1 can comprise one or two amino acid substitutions when compared to positions 31-35 of SEQ ID NO: 8. Also disclosed herein are isolated antibodies comprising a heavy chain variable region, wherein the heavy chain variable region comprises a variant CDRH2, positions 50-66 of SEQ ID NO: 8. In some aspects, the variant CDRH2 can comprise one or two amino acid substitutions when compared to positions 50-66 of SEQ ID NO: 8. Further disclosed herein are isolated antibodies comprising a heavy chain variable region, wherein the heavy chain variable region can comprise a variant CDRH3, positions 99-112 of SEQ ID NO: 8. In some aspects, the variant CDRH3 can comprise one or two amino acid substitutions when compared to positions 99-112 of SEQ ID NO: 8.

Disclosed herein are isolated antibodies comprising a light chain variable region and a heavy chain variable region, wherein the light chain variable region comprises a variant complementarity determining region light chain 1 (CDRL1) comprising positions 24-39 of SEQ ID NO: 4, wherein the variant CDRL 1 comprises one or two amino acid substitutions when compared to positions 24-39 of SEQ ID NO: 4; a variant complementarity determining region light chain 2 (CDRL2) comprising positions 55-61 of SEQ ID NO: 4, wherein the variant CDRL2 comprises one or two amino acid substitutions when compared to positions 55-61 of SEQ ID NO: 74; and a variant complementarity determining region light chain 3 (CDRL3) comprising 94-102 positions of SEQ ID NO: 4, wherein the variant CDRL3 comprises one or two amino acid substitutions when compared to positions 94-102 of SEQ ID NO: 4; wherein the heavy chain variable region comprises a variant complementarity determining region heavy chain 1 (CDRH1) comprising positions 31-35 of SEQ ID NO: 8, wherein the variant CDRH1 comprises one or two amino acid substitutions when compared to positions 31-35 of SEQ ID NO: 8; a variant complementarity determining region heavy chain 2 (CDRH2) comprising positions 50-66 of SEQ ID NO: 8, and wherein the variant CDRH2 comprises one or two amino acid substitutions when compared to positions 50-66 of SEQ ID NO: 8; and a variant complementarity determining region heavy chain 3 (CDRH3) comprising positions 99-112 of SEQ ID NO: 8, wherein the variant CDRH3 comprises one or two amino acid substitutions when compared to positions 99-112 of SEQ ID NO: 8.

Substitutional variants typically contain the exchange of one amino acid for another at one or more sites within the protein and may be designed to modulate one or more properties of the polypeptide, with or without the loss of other functions or properties. Substitutions may be conservative, that is, one amino acid is replaced with one of similar shape and charge. Conservative substitutions are as described in Table 1, supra. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some aspects, the CDRs can be defined according to the Kabat definition. In some aspects, the CDRs can be defined according to the IMGT definition.

In some aspects, the antibodies disclosed herein can be recombinantly engineered, chimerized, or humanized. In some aspects, the antibodies disclosed herein can be affinity matured or human antibodies. In some aspects, the antibodies disclosed herein can be a Fab, an Fab', an F(ab')2, a Fv, a scFv, a diabody or fragments thereof. In some aspects, the antibody can be a monoclonal antibody. In some aspects, the monoclonal antibodies can be humanized or chimeric forms thereof. In some aspects, the monoclonal antibody can be a humanized antibody. By known means and as described herein, polyclonal or monoclonal antibodies, antibody fragments, binding domains and CDRs (including engineered forms of any of the foregoing) may be created that are specific for *Klebsiella pneumoniae* sequence type 258 expressing wzi50, wzi154 or wzi29 capsular polysaccharide antigen, one or more of its respective epitopes, or conjugates of any of the foregoing, whether such antigens or epitopes are isolated from natural sources or are synthetic derivatives or variants of the natural protein.

A monoclonal antibody is a single, clonal species of antibody wherein every antibody molecule recognizes the same epitope because all antibody producing cells are derived from a single, antibody-producing B-lymphocyte (or other clonal cell, such as a cell that recombinantly expresses the antibody molecule). The methods for generating monoclonal antibodies (MAbs) generally begin along the same lines as those for preparing polyclonal antibodies. In some aspects, rodents such as mice and rats are used in generating monoclonal antibodies. In some aspects, rabbit, sheep, or frog cells are used in generating monoclonal antibodies. The use of rats is well known and may provide certain advantages. Mice (e.g., BALB/c mice) are routinely used and generally give a high percentage of stable fusions. Hybridoma technology as used in monoclonal antibody production involves the fusion of a single, antibody-producing B lymphocyte isolated from a mouse previously immunized with a *Klebsiella pneumoniae* sequence type 258 or other *Klebsiella pneumoniae* wzi50, wzi154 or wzi29 capsular polysaccharide protein or peptide with an immortalized cell, e.g., a mouse cell line. This technology provides a method to propagate a single antibody-producing cell for an indefinite number of generations, such that unlimited quantities of structurally identical antibodies having the same antigen or epitope specificity, i.e., monoclonal antibodies, may be produced.

Methods have been developed to replace light and heavy chain constant domains of the monoclonal antibody with analogous domains of human origin, leaving the variable regions of the foreign antibody intact. Alternatively, "fully human" monoclonal antibodies are produced in mice or rats that are transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDRs are derived from non-human (e.g., mouse, rat, chicken, llama, etc.) monoclonal antibodies, and the framework regions are derived from human antibody amino acid sequences. The replacement of amino acid sequences in the antibody that are characteristic of rodents with amino acid sequences found in the corresponding positions of human antibodies reduces the likelihood of adverse immune reaction to foreign protein during therapeutic use in humans. A hybridoma or other cell producing an antibody may also be subject to genetic mutation or other changes, which may or may not alter the binding specificity of antibodies produced by the hybridoma.

Engineered antibodies may be created using monoclonal and other antibodies and recombinant DNA technology to produce other antibodies or chimeric molecules that retain the antigen or epitope binding specificity of the original antibody, i.e., the molecule has a specific binding domain. Such techniques may involve introducing DNA encoding the immunoglobulin variable region or the CDRs of an antibody into the genetic material for the framework regions, constant regions, or constant regions plus framework regions, of a different antibody. See, for instance, U.S. Pat. Nos. 5,091,513 and 6,881,557, which are incorporated herein by reference.

By known means as described herein, polyclonal or monoclonal antibodies, antibody fragments having binding activity, binding domains and CDRs (including engineered forms of any of the foregoing), may be created that specifically bind to *Klebsiella pneumoniae* sequence type 258 or other *Klebsiella pneumoniae* wzi50, wzi154 or wzi29 capsular polysaccharide, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. In some aspects, the antibodies can be ovine, murine (e.g., mouse and rat), rabbit, goat. guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in Marks et al., 1992, *Bio/Technol.,* 10:779-783; Stemmer, 1994, *Nature,* 370:389-391; Gram et al., 1992, *Proc. Natl. Acad. Sci. USA,* 89:3576-3580; Barbas et al., 1994, *Proc. Natl. Acad. Sci. USA,* 91:3809-3813; and Schier et al., 1996, *Gene,* 169(2):147-155.

Methods for producing polyclonal antibodies in various animal species, as well as for producing monoclonal antibodies of various types, including humanized, chimeric, and fully human, are well known in the art and are highly reproducible. For example, the following U.S. patents provide descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098.

In some aspects, the antibody can be a single chain antibody. In some aspects, the antibody can be linked to a detectable label. In some aspects, antibody can be a monovalent or a bivalent antibody.

In some aspects, the antibodies disclosed herein can be an IgG, an IgM, an IgA, an IgD, or an IgE antibody or antigen binding fragment thereof. In some aspects, the antibodies can be of the IgG, IgM, IgA, IgD, and IgE Ig classes or a genetically modified IgG class antibody, as well as polypeptides comprising one or more antibody CDR regions that retain antigen binding activity. In some aspects, the antibody can be an IgG class of antibody. In some aspects, the IgG class antibody can be an IgG1, IgG2, IgG3, or IgG4 class antibody.

In some aspects, the antibody can be a bispecific antibody. Unifying two antigen binding sites of different specificity into a single construct, bispecific antibodies have the ability to bring together two discreet antigens with exquisite specificity and therefore have great potential as therapeutic agents. Bispecific antibodies were originally made by fusing two hybridomas, each capable of producing a different immunoglobulin. Bispecific antibodies can also be produced by joining two scFv antibody fragments while omitting the Fc portion present in full immunoglobulins. Each scFv unit in such constructs can contain one variable domain from each of the heavy ($V_H$) and light ($V_L$) antibody chains, joined with one another via a synthetic polypeptide linker, the latter often being genetically engineered so as to be minimally immunogenic while remaining maximally resistant to proteolysis. Respective scFv units may be joined by a number of known techniques, including incorporation of a short (usually less than 10 amino acids) polypeptide spacer bridging the two scFv units, thereby creating a bispecific single chain antibody. The resulting bispecific single chain antibody is therefore a species containing two $V_H/V_L$ pairs of different specificity on a single polypeptide chain, in which the $V_H$ and $V_L$ domains in a respective scFv unit are separated by a polypeptide linker long enough to allow intramolecular association between these two domains, such that the so-formed scFv units are contiguously tethered to one another through a polypeptide spacer kept short enough to prevent unwanted association between, for example, the VH domain of one scFv unit and the VL of the other scFv unit.

Examples of antibody fragments suitable for use include, without limitation: (i) the Fab fragment, consisting of $V_L$, $V_H$, $C_L$, and CHI domains; (ii) the "Fd" fragment consisting of the $V_H$ and $CH_1$ domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), in which a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent, or multispecific fragments constructed by gene fusion (U.S. Patent Appln. Pub. No. 20050214860). Fv, scFv, or diabody molecules may be stabilized by the incorporation of disulfide bridges linking the $V_H$ and $V_L$ domains. Minibodies comprising a scFv joined to a $C_{H3}$ domain (Hu et al., 1996, *Cancer Res.,* 56:3055-3061) may also be useful. In addition, antibody-like binding peptidomimetics are also contemplated. "Antibody like binding peptidomimetics" (ABiPs), which are peptides that act as pared-down antibodies and have certain advantages of longer serum half-life as well as less cumbersome synthesis methods, have been reported by Liu et al., 2003, *Cell Mol. Biol.,* 49:209-216.

Animals may be inoculated with an antigen, such as a *Klebsiella pneumoniae* sequence type 258 wzi50, wzi154 or wzi29 capsular polysaccharide to generate an immune response and produce antibodies specific for the *Klebsiella pneumoniae* sequence type 258 or other *Klebsiella pneumoniae* wzi50, wzi154 or wzi29 capsular polysaccharide. Frequently, an antigen is bound or conjugated to another molecule to enhance the immune response. As used herein, a conjugate can be any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

The antibodies described herein directed to *Klebsiella pneumoniae* sequence type 258 or other *Klebsiella pneumoniae* wzi50, wzi154 or wzi29 capsular polysaccharide will have the ability to neutralize, block or inhibit *Klebsiella pneumonia* ST258 or other *Klebsiella pneumoniae* regardless of the animal species, monoclonal cell line or other source of the antibody. Certain animal species may be less preferable for generating therapeutic antibodies because they may be more likely to cause an immune or allergic response due to activation of the complement system through the "Fc" portion of the antibody. However, whole antibodies may be enzymatically digested into the "Fc" (complement binding) fragment, and into peptide fragments having the binding domains or CDRs. Removal of the Fc portion reduces the likelihood that this antibody fragment will elicit an undesirable immunological response and, thus, antibodies without an Fc portion may be preferential for prophylactic or therapeutic treatments. As described above, antibodies may also be constructed so as to be chimeric, humanized, or partially or fully human, so as to reduce or eliminate potential adverse immunological effects resulting from administering to an animal an antibody that has been produced in, or has amino acid sequences from, another species.

In some aspects, the antibody binds to *Klebsiella pneumoniae* sequence type 258 wzi50, wzi154 or wzi29 capsular polysaccharide an affinity of greater than or equal to 4 nM. In some aspects, the antibody binds to *Klebsiella pneumoniae* sequence type 258 wzi50, wzi154 or wzi29 capsular polysaccharide an affinity of greater than or equal to 4.7 nM. In some aspects, the antibody selectively binds to *Klebsiella pneumoniae* sequence type 258 expressing wzi50, wzi154 or wzi29 capsular polysaccharide and inhibits or prevents a *Klebsiella pneumonia* ST258 infection. In some aspects, the antibody selectively binds to *Klebsiella pneumoniae* sequence type 258 expressing wzi50, wzi154 or wzi29 capsular polysaccharide and inhibits growth in whole blood and promotes phagocytosis. In some aspects, the whole blood can be whole blood in a human subject.

The term "specifically binds" (or "immunospecifically binds") is not intended to indicate that an antibody binds exclusively to its intended target. Rather, an antibody "specifically binds" if its affinity for its intended target is about, for example, 5-fold greater when compared to its affinity for a non-target molecule. Suitably there is no significant cross-reaction or cross-binding with undesired substances. The affinity of the antibody will, for example, be at least about 5-fold, such as 10-fold, such as 25-fold, especially 50-fold, and particularly 100-fold or more, greater for a target molecule than its affinity for a non-target molecule. In some aspects, specific binding between an antibody or other binding agent and an antigen means a binding affinity of at least $10^6$ $M-^1$. Antibodies may, for example, bind with affinities of at least about 107 $M-^1$, such as between about $10^8$ $M-^1$ to about 109 $M-^1$, about 109 $M-^1$ to about $10^{10}$ $M-^1$, or about $10-^{10}M-^1$ to about $10^{11}$ $M-^1$. Antibodies may, for example, bind with an EC50 of 50 nM or less, 10 nM or less, 1 nM or less, 100 pM or less, or more preferably 10 pM or less. In some aspects, the antibodies can bind with an EC50 of about 60 μg/ml, 59 μg/ml, 58 μg/ml, 57 μg/ml, 56 μg/ml, 55 μg/ml, 54 μg/ml, 53 μg/ml, 52 μg/ml, 51 μg/ml, 50 μg/ml or less. In some aspects, the antibodies can bind with an EC50 of about 50 μg/ml, 49 μg/ml, 48 μg/ml, 47 μg/ml, 46 μg/ml, 45 μg/ml, 44 μg/ml, 43 μg/ml, 42 μg/ml, 41 μg/ml, 40 μg/ml or less. In some aspects, the antibodies can bind with an EC50 of about 40 μg/ml, 39 μg/ml, 38 μg/ml, 37 μg/ml, 36 μg/ml, 35 μg/ml, 34 μg/ml, 33 μg/ml, 32 μg/ml, 31 μg/ml, 30 μg/ml or less.

In some aspects, the antibodies described herein comprise a heavy chain variable region, wherein the heavy chain variable region comprises one or more complementarity determining region (CDRHs) CDRH1, CDRH2 and CDRH3 with amino acid sequences that have 0, 1, 2, 3, 4, or 5 conservative amino acid substitutions in 1, 2 or 3 CDRHs having the amino acid sequences of SEQ ID NO: 5, SEQ ID NO: 6 or SEQ ID NO: 7, respectively; and/or a light chain variable region comprising one or more complementarity determining region (CDRLs) CDRL1, CDRL2 and CDRL3 with the amino acid sequences that have 0, 1, 2, 3, 4, or 5 conservative amino acid substitutions in 1, 2 or 3 CDRLs having the amino acid sequences of SEQ ID NO: 1, SEQ ID NO: 2, and SEQ ID NO: 3, respectively.

In some aspects, the antibodies disclosed herein can specifically bind to *Klebsiella pneumoniae* sequence type 258 or other *Klebsiella pneumoniae* expressing wzi50, wzi154 or wzi29 capsular polysaccharide. In some aspects, the antibodies disclosed herein can bind to at least one polysaccharide in Table 5. In some aspects, the antibodies disclosed herein can specifically bind to at least one polysaccharide in Table 5.

In some aspects, the antibodies disclosed herein can inhibits or prevents a *Klebsiella pneumonia* ST258 or other *Klebsiella pneumoniae* infection. In some aspects, the antibodies disclosed herein can induce an immune response. In some aspects, the antibodies disclosed herein can induce complement-mediated or complement-independent opsonophagocytosis. In some aspects, the antibodies disclosed herein can reduce lung burden or dissemination of *Klebsiella pneumonia* ST258 or other *Klebsiella pneumoniae* expressing wzi50, wzi154 or wzi29 capsular polysaccharides. In some aspects, the antibodies disclosed herein can reduce lung liver or spleen bacterial load. In some aspects, the antibodies disclosed herein can increase opsonophagocytic uptake.

Antibody proteins may be recombinant, or synthesized in vitro. It is contemplated that in anti-*Klebsiella pneumoniae* sequence type 258 wzi50, wzi154 or wzi29 capsular polysaccharide antibody-containing or other anti-*Klebsiella pneumoniae* strain wzi50, wzi154 or wzi29 capsular polysaccharide antibody-containing compositions as described herein can comprise between about 0.001 mg and about 10 mg of total antibody polypeptide per ml. Thus, the concentration of antibody protein in a composition can be about, at least about or at most about or equal to 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, at most about, or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds to *Klebsiella pneumoniae* sequence type 258 or other *Klebsiella pneumoniae* expressing wzi50, wzi154 or wzi29 capsular polysaccharides.

Disclosed herein are compositions comprising any of the antibodies or isolated antibodies described herein. In some aspects, the compositions can further comprise at least one pharmaceutically acceptable carrier or diluent.

In some aspects, the compositions described herein can comprise a detectable label or reporter. An antibody or an immunological portion of an antibody that retains binding activity, can be chemically conjugated to, or recombinantly expressed as, a fusion protein with other proteins. For the purposes as described herein, all such fused proteins are included in the definition of antibodies or an immunological portion of an antibody. In some aspects, antibodies and antibody-like molecules generated against *Klebsiella pneumoniae* sequence type 258 or other *Klebsiella pneumoniae* expressing wzi50, wzi154 or wzi29 capsular polysaccharides or polypeptides that are linked to at least one agent to form an antibody conjugate or payload are encompassed. In order to increase the efficacy of antibody molecules as diagnostic or therapeutic agents, it is conventional to link or covalently bind or complex at least one desired molecule or moiety to the antibody. Such a linked molecule or moiety may be, but is not limited to, at least one effector, detectable label or reporter molecule. Effector molecules comprise molecules having a desired activity, e.g., cytotoxic activity. Non-limiting examples of effector molecules that may be attached to antibodies include toxins, therapeutic enzymes, antibiotics, radio-labeled nucleotides and the like. By contrast, a reporter molecule or detectable label is defined as any moiety that may be detected using an assay. Non-limiting examples of reporter molecules and detectable labels that can be conjugated to antibodies include enzymes, radiolabels, haptens, fluorescent labels, phosphorescent molecules. chemiluminescent molecules, chromophores, luminescent molecules, photoaffinity molecules, colored particles or ligands, such as biotin, and the like. Several methods are known in the art for attaching or conjugating an antibody to a conjugate molecule or moiety. Some attachment methods involve the use of a metal chelate complex, employing by way of nonlimiting example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Antibodies, particularly the monoclonal antibodies as described herein, may also be reacted with an enzyme in the presence of a coupling agent such as glutaraldehyde or periodate. Conjugates with fluorescein markers are conventionally prepared in the presence of these coupling agents or by reaction with an isothiocyanate. In some aspects, an *Klebsiella pneumoniae* sequence type 258 or other *Klebsiella pneumoniae* expressing wzi50, wzi154 or wzi29 capsular polysaccharides antibody as described herein, particularly a binding fragment thereof, may be coupled or linked to a compound or substance, such as polyethylene glycol (PEG), to increase its in vivo half-life in plasma, serum, or blood following administration.

In some aspects, the antibodies described herein can be specifically bind to their intended target. In some aspects, the antibodies described herein have no off site or off target binding.

Disclosed herein are vectors comprising a sequence encoding the disclosed antibody or antibody fragment thereof.

Disclosed herein are nucleic acid sequences capable of encoding the disclosed antibody or antibody fragment thereof.

Disclosed herein are cells comprising the disclosed antibody or antibody fragment thereof, nucleic acid sequences encoding the disclosed antibody or antibody fragment thereof and vectors comprising a sequence encoding the disclosed antibody or antibody fragment thereof Methods Disclosed herein are methods for inhibiting, treating or preventing a *Klebsiella pneumonia* ST258 or other *Klebsiella pneumoniae* strain infection in a subject. The methods can comprise administering to the subject a therapeutically effective amount of any of the isolated antibodies described herein or any of the compositions described herein. In some aspects, the subject can be infected or exposed to *Klebsiella pneumonia* ST258 or other *Klebsiella pneumoniae* strains expressing wzi50, wzi154 or wzi29 capsular polysaccharides. In some aspects, the *Klebsiella pneumonia* ST258 or other *Klebsiella pneumoniae* strains can express wzi50, wzi154 and wzi29 capsular polysaccharides. In some aspects, the *Klebsiella pneumonia* ST258 or other *Klebsiella pneumoniae* strains can express wzi50, wzi154 or wzi29 capsular polysaccharides. In some aspects, the *Klebsiella pneumonia* ST258 can express wzi50, wzi154, wzi29 capsular polysaccharides or a combination thereof. In some aspects, other *Klebsiella pneumoniae* strains can express wzi50, wzi154 or wzi29 capsular polysaccharides (e.g., ESBL).

Disclosed herein are methods of inducing an immune response in a subject. In some aspects, the methods can comprise administering to the subject a therapeutically effective amount of any of the isolated antibodies described herein or any of the composition disclosed herein. In some aspects, the subject can be infected or exposed to *Klebsiella pneumonia* ST258 or other *Klebsiella pneumonia* strains expressing wzi50, wzi154 or wzi29 capsular polysaccharides. In some aspects, the *Klebsiella pneumonia* ST258 or other *Klebsiella pneumonia* strains can express wzi50, wzi154 and wzi29 capsular polysaccharides. In some aspects, the *Klebsiella pneumonia* ST258 or other *Klebsiella pneumonia* strains can express wzi50, wzi154 or wzi29 capsular polysaccharides. In some aspects, the *Klebsiella pneumonia* ST258 or other *Klebsiella pneumonia* strains can express wzi50, wzi154, wzi29 capsular polysaccharides or a combination thereof.

Disclosed herein are methods of inducing complement-mediated or complement-independent opsonophagocytosis in a subject. In some aspects, the methods can comprise administering to the subject a therapeutically effective amount of any of the isolated antibodies described herein or any of the composition disclosed herein. In some aspects, the subject can be infected or exposed to *Klebsiella pneumonia* ST258 or other *Klebsiella pneumonia* strains. In some aspects, the *Klebsiella pneumonia* ST258 or other *Klebsiella pneumonia* strains can express wzi50, wzi154 and wzi29 capsular polysaccharides. In some aspects, the *Klebsiella pneumonia* ST258 or other *Klebsiella pneumonia* strains can express wzi50, wzi154 or wzi29 capsular polysaccharides. In some aspects, the *Klebsiella pneumonia* ST258 or other *Klebsiella pneumonia* strains can express wzi50, wzi154, wzi29 capsular polysaccharides or a combination thereof.

Disclosed herein are methods of reducing lung burden or dissemination of *Klebsiella pneumonia* ST258 or other *Klebsiella pneumonia* strains in a subject. In some aspects, the methods can comprise administering to the subject a therapeutically effective amount of any of the isolated antibodies described herein or any of the composition disclosed herein. In some aspects, the subject can be infected or exposed to *Klebsiella pneumonia* ST258 or other *Klebsiella pneumonia* strains. In some aspects, the *Klebsiella pneumonia* ST258 or other *Klebsiella pneumonia* strains can express wzi50, wzi154 and wzi29 capsular polysaccharides. In some aspects, the *Klebsiella pneumonia* ST258 or other *Klebsiella pneumonia* strains can express wzi50, wzi154 or wzi29 capsular polysaccharides. In some aspects, the *Klebsiella pneumonia* ST258 or other *Klebsiella pneumonia* strains can express wzi50, wzi154, wzi29 capsular polysaccharides or a combination thereof.

Disclosed herein are methods of increasing opsonophagocytic uptake in a subject. In some aspects, the methods can comprise administering to the subject a therapeutically effective amount of any of the isolated antibodies described herein or any of the composition disclosed herein. In some aspects, the subject can be infected or exposed to *Klebsiella pneumonia* ST258 or other *Klebsiella pneumonia* strains. In some aspects, the *Klebsiella pneumonia* ST258 or other *Klebsiella pneumonia* strains can express wzi50, wzi154 and wzi29 capsular polysaccharides. In some aspects, the *Klebsiella pneumonia* ST258 or other *Klebsiella pneumonia* strains can express wzi50, wzi154 or wzi29 capsular polysaccharides. In some aspects, the *Klebsiella pneumonia* ST258 or other *Klebsiella pneumonia* strains can express wzi50, wzi154, wzi29 capsular polysaccharides or a combination thereof.

Disclosed herein are methods of reducing lung, liver or spleen bacterial load or dissemination of *Klebsiella pneumonia* ST258 or other *Klebsiella pneumonia* strains in a subject. In some aspects, the methods can comprise administering to the subject a therapeutically effective amount of any of the isolated antibodies described herein or any of the composition disclosed herein. In some aspects, the subject can be infected or exposed to *Klebsiella pneumonia* ST258 or other *Klebsiella pneumonia* strains. In some aspects, the *Klebsiella pneumonia* ST258 or other *Klebsiella pneumonia* strains can express wzi50, wzi154 and wzi29 capsular polysaccharides. In some aspects, the *Klebsiella pneumonia* ST258 or other *Klebsiella pneumonia* strains can express wzi50, wzi154 or wzi29 capsular polysaccharides. In some aspects, the *Klebsiella pneumonia* ST258 or other *Klebsiella pneumonia* strains can express wzi50, wzi154, wzi29 capsular polysaccharides or a combination thereof.

Examples of ST258 CR-*Klebsiella pneumonia* strains that express wzi 29 capsular polysaccharides include but are not limited to Kp3, Kp10, Kp22, Kp29, Kp36, Kp37, Kp44, and Kp54.

Examples of other *Klebsiella pneumonia* strains that express wzi 29 capsular polysaccharides include but are not limited to ESBL12, ESBL30, and ESBL31.

Examples of ST258 CR-*Klebsiella pneumonia* strains that express wzi 50 capsular polysaccharides include but are not limited to Kp14, Kp15, Kp18, Kp19, Kp38, Kp41, Kp42, and Kp43.

Examples of ST258 CR-*Klebsiella pneumonia* strains that express wzi 154 capsular polysaccharides include but are not limited to Kp1, Kp2, Kp5, Kp6, Kp11, Kp13, Kp24, Kp25, Kp26, Kp28, Kp30, and Kp34.

Examples of other *Klebsiella pneumonia* strains that express wzi 154 capsular polysaccharides include but are not limited to ESBL6, ESBL 15, ESBL20, ESBL22, ESBL28, ESBL39, and ESBL43.

In some aspects, the subject can be identified in need of treatment before the administering step. In some aspects, the antibody can be administered in a pharmaceutically acceptable composition. In some aspects, the antibody can be administered systemically, intravenously, intradermally, intramuscularly, intraperitoneally, subcutaneously, intranasally or by aerosolization.

In some aspects, the methods can further comprising administering one or more drugs or therapeutic agents to the subject. Examples of drugs or therapeutic agents that can be administered in combination with any of the antibodies described herein include but are not limited to oral quinolones, imipenem, aztreonam, intravenous aminoglycosides, third generation cephalosporins, piperacillin/tazobactam colistin, tigecycline, gentamicin, and carbapenem.

Also disclosed herein are methods for developing and producing the disclosed monoclonal antibodies against *Klebsiella pneumonia* strains expressing wzi50 capsular polysaccharides. Disclosed herein are methods of vaccinating and generating monoclonal antibodies of anti-wzi50 capsular polysaccharides (referred to herein as "24D11"). Briefly, C57BL/6 mice were injected with either unconjugated wzi50 CPS, Ba-PA conjugated wzi50 CPS or Ba-PA alone mixed with Complete Freund's Adjuvant for primary dose and mixed with Incomplete Freund's Adjuvant for booster doses. Mice were boosted four times with two weeks apart intervals and serum were collected for testing. Ten weeks post initial vaccination, mice and their serum collected for analyzing anti-wzi50 antibodies titers in vaccinated mice. Mice that were screened to be positive for anti-wzi50 antibodies titers (1:10,000), and were given a booster two weeks prior to sacrifice. Mice were then sacrificed, and their spleens were isolated for hybridoma fusion. PEG-mediated fusion of splenocytes to myeloma lines Ag.8 or NSO$^{bcl2}$ was performed, followed by selection in hypoxanthine-aminopterin-thymidine (HAT) medium. Fused splenocytes-myeloma cells were screened by ELISA for wzi50 CPS-binding antibodies and positive fused-cells were expanded and then cloned in soft agar (SeaPlaque) where individual clones underwent final confirmatory testing and isotyping by ELISA. 24D11 hybridoma clone was then expanded in CELLine (Wheaton) flasks and 24D11 monoclonal antibodies were purified using Pierce Protein G Affinity Chromatography as per manufacturer's protocol.

Treatment of diseases. Disclosed herein are antibodies or antigen binding fragments thereof, as described herein (e.g., an antibody that specifically and preferentially binds to *Klebsiella pneumonia* ST258 or other *Klebsiella pneumonia* strains that expresses wzi50, wzi154 or wzi29 capsular polysaccharides) that can be used in treatment methods and administered to inhibit, treat or prevent a *Klebsiella pneumonia* ST258 or other *Klebsiella pneumonia* strains infection. Accordingly, provided herein are methods of inhibiting, treating or preventing a *Klebsiella pneumonia* ST258 or other *Klebsiella pneumonia* strains infection in a subject having a *Klebsiella pneumonia* ST258 or other *Klebsiella pneumonia* strains infection, at risk for having a *Klebsiella pneumonia* ST258 or other *Klebsiella pneumonia* strains infection, or exposed to *Klebsiella pneumonia* ST258 or other *Klebsiella pneumonia* strains. In some aspects, the methods can comprise administering to a subject a therapeutically effective amount of any of the antibodies described herein or any of the compositions comprising at least one of antibodies as described herein. In some aspects, the drug or therapeutic agent can be an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody or a composition comprising at least one anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody.

The compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with an autoimmune disease or cancer, or undergoing or have undergone an allograft transplant in an amount sufficient to at least partially improve a sign or symptom or to inhibit the progression of (and preferably arrest) the symptoms of the disease or condition, its complications, and consequences. An amount adequate to accomplish this is defined as a "therapeutically effective amount." A therapeutically effective amount of a composition (e.g., a pharmaceutical composition) can be an amount that achieves a cure, but that outcome is only one among several that can be achieved. As noted, a therapeutically effective amount includes amounts that provide a treatment in which the onset or progression of a *Klebsiella pneumonia* ST258 or other *Klebsiella pneumonia* strain infection is delayed, hindered, or prevented, or a *Klebsiella pneumonia* ST258 or other *Klebsiella pneumonia* strain infection or a symptom of the a *Klebsiella pneumonia* ST258 or other *Klebsiella pneumonia* strain infection is ameliorated or its frequency can be reduced. One or more of the symptoms can be less severe. Recovery can be accelerated in an individual who has been treated. For example, treatment of a *Klebsiella pneumonia* ST258 or other *Klebsiella pneumonia* strain infection may involve, for example, a reduction lung burden or dissemination of a *Klebsiella pneumonia* ST258 or other *Klebsiella pneumonia* strain infection, a reduction in lung, liver or spleen bacterial load of a *Klebsiella pneumonia* ST258 or other *Klebsiella pneumonia* strain infection; or an increase in opsonophagocytic uptake, an induction of an immune response, an induction of complement-mediated or complement-independent opsonophagocytosis, or prevention of a *Klebsiella pneumonia* ST258 or other *Klebsiella pneumonia* strain infection.

Treatment of these subjects with an effective amount of at least one of the anti-*Klebsiella pneumoniae* sequence type 258 wzi50, wzi154 or wzi29 capsular polysaccharide antibodies as described herein can result in binding of one or more of the disclosed antibodies to *Klebsiella pneumoniae* sequence type 258 expressing wzi50, wzi154 or wzi29 capsular polysaccharides, thereby preventing dissemination of *Klebsiella pneumonia* ST258 or other *Klebsiella pneumonia* strain expressing wzi50, wzi154 and wzi29 capsular polysaccharides. Accordingly, the methods as provided are advantageous for a subject who is in need of, capable of benefiting from, or who is desirous of receiving the benefit of, the anti-infective results or the amelioration of one or more infectious symptoms achieved by the practice of the present methods. A subject's seeking the therapeutic benefits of the methods involving administration of at least one anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody in a therapeutically effective amount, or receiving such therapeutic benefits offer advantages to the art. In addition, the present methods offer the further advantages of eliminating or avoiding side effects, adverse outcomes, contraindications, and the like, or reducing the risk or potential for such issues to occur compared with other treatments and treatment modalities The anti-*Klebsiella pneumoniae* sequence type 258 wzi50, wzi154 or wzi29 capsular polysaccharide antibodies or other anti-*Klebsiella pneumonia* e sequence type 258 wzi50, wzi154 or wzi29 capsular polysaccharide antibodies, such as monoclonal antibodies, can be used as anti-infective agents in a variety of modalities. In some aspects, the methods described herein use the antibodies disclosed herein as anti-infective agents, and, thus, comprise contacting a population of cells with a therapeutically effective amount of one or more of the antibodies, or a composition containing one or more of the antibodies, for a time period sufficient to block or inhibit *Klebsiella pneumoniae* sequence type 258 or other *Klebsiella pneumoniae* strains expressing wz50, wzi154 or wzi29 capsular polysaccharides, induce an immune response, induce complement-mediated or complement-independent opsonophagocytosis, educe lung burden or dissemination of *Klebsiella pneumonia* ST258 or other *Klebsiella pneumoniae* strains, reduce lung, liver or spleen bacterial load of a *Klebsiella pneumonia* ST258 or other *Klebsiella pneumoniae* strain infection, or increase in opsonophagocytic uptake.

In some aspects, contacting a cell in vivo is accomplished by administering to a subject in need, for example, by intravenous, subcutaneous, intraperitoneal, or by aerosolization, a therapeutically effective amount of a physiologically tolerable composition comprising an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody as described herein. The antibody may be administered parenterally by injection or by gradual infusion over time. Useful administration and delivery regimens include intravenous, intraperitoneal, oral, intramuscular, subcutaneous, intracavity, intranasally, transdermal, dermal, peristaltic means, direct injection into the tissue containing the cells or by aerosolization.

Therapeutic compositions comprising antibodies are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle. The compositions comprising any of the anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies disclosed herein can be administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimens for initial and booster administration are also contemplated and may typically involve an initial administration followed by repeated doses at one or more intervals (hours) by a subsequent injection or other administration. In some aspects, multiple administrations can be suitable for maintaining continuously high serum and tissue levels of antibody. Alternatively, continuous intravenous infusion sufficient to maintain concentrations in the blood in the ranges specified for in vivo therapies are contemplated.

It is contemplated that an anti-*Klebsiella pneumoniae* sequence type 258 wzi50, wzi154 or wzi29 capsular polysaccharide antibody or other anti-*Klebsiella pneumoniae* sequence type 258 wzi50, wzi154 orwzi29 capsular polysaccharide antibodies as described herein can be administered systemically or locally to treat or prevent disease, such as to reduce lung burden or dissemination of *Klebsiella pneumonia* ST258 or other *Klebsiella pneumoniae* strains, inducing complement-mediated or complement-independent opsonophagocytosis, induce an immune response, reducing lung, liver or spleen bacterial load of a *Klebsiella pneumonia* ST258 or other *Klebsiella pneumoniae* strain infection, increasing opsonophagocytic uptake, or inhibit (or prevent) a *Klebsiella pneumonia* ST258 or other *Klebsiella pneumoniae* strain infection in infected patients or subjects exposed to or at risk for a *Klebsiella pneumonia* ST258 or other *Klebsiella pneumoniae* strains infection. The antibodies can be administered alone or in combination with anti-infective drugs or antibiotics. As noted herein, a therapeutically effective amount of an antibody can be a predetermined amount calculated to achieve the desired effect. Thus, the dosage ranges for the administration of an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibodies are those large enough to produce the desired effect in which the symptoms of lung burden or dissemination of *Klebsiella pneumonia* ST258 or other *Klebsiella pneumoniae* strains are reduced. Optimally, the dosage should not be so large as to cause adverse side effects, such as hyperviscosity syndromes, pulmonary edema, congestive heart failure, neurological effects, and the like. Generally, the dosage will vary with age of, condition of, size and gender of, and extent of the disease in the subject or patient and can be determined by one of skill in the art such as a medical practitioner or clinician. Of course, the dosage may be adjusted by the individual physician in the event of any complication.

Treatment methods. In some aspects, the compositions and methods as described herein comprise the administration of an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibodies as described herein, alone, or in combination with a second or additional drug or therapy. Such drug or therapy may be applied in the treatment of any disease that is associated with a *Klebsiella pneumonia* ST258 or other *Klebsiella pneumoniae* strain infection. the compositions and methods described herein can comprise at least one anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody that preferentially binds to *Klebsiella pneumoniae* sequence type 258 or other *Klebsiella pneumoniae* strains expressing wzi50, wzi154 or wzi29 capsular polysaccharides and has a therapeutic or protective effect in the treatment, inhibition or prevention of a *Klebsiella pneumonia* ST258 or other *Klebsiella pneumoniae* strain infection, thereby providing a therapeutic effect and treatment.

The compositions and methods, including combination therapies, have a therapeutic or protective effect and may enhance the therapeutic or protective effect, and/or increase the therapeutic effect of another drug, therapy or therapeutic agent (e.g., anti-infective or antibiotic therapy). In some aspects, a second or additional drug can be ceftazdime-avibactam.

Therapeutic and prophylactic methods and compositions can be provided in a combined amount effective to achieve the desired effect, such as the inhibition or prevention of a *Klebsiella pneumonia* ST258 or other *Klebsiella pneumoniae* strain infection, the induction complement-mediated or complement-independent opsonophagocytosis, induction an immune response, or reduction lung burden or dissemination or reduction in lung, liver or spleen bacterial load of a *Klebsiella pneumonia* ST258 or other *Klebsiella pneumoniae* strain infection. This process may involve administering an anti-*Klebsiella pneumoniae* sequence type 258 wzi50, wzi154 or wzi29 capsular polysaccharide antibody or a binding fragment thereof and a second therapy. The second therapy may or may not have a direct cytotoxic effect. A tissue and/or cell can be exposed to one or more compositions or pharmacological formulation(s) comprising one or more of the agents (e.g., an antibody or an anti-infective agent), or by exposing the tissue and/or cell with two or more distinct compositions or formulations, wherein one composition provides, for example, 1) an antibody, 2) an anti-infective agent, 3) both an antibody and an anti-infective agent, or 4) two or more antibodies. In some aspects, the second therapy can be also an anti-*Klebsiella pneumoniae* sequence type 258 wzi50, wzi154 or wzi29 capsular polysaccharide antibody. Also, it is contemplated that such a combination therapy can be used in conjunction with antibiotic therapy. In some aspects, a second therapy can be ceftazdime-avibactam.

By way of example, the terms "contacted" and "exposed," when applied to a cell, are used herein to describe a process by which a therapeutic polypeptide, for example, an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody as described herein, is delivered to a target cell or is placed in direct juxtaposition with the target cell, particularly to bind specifically to the target antigen, e.g., *Klebsiella pneumoniae* sequence type 258 or other *Klebsiella pneumoniae* strains expressing wzi50, wzi154 or wzi29 capsular polysaccharides. Such binding by a therapeutic anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody or binding fragment thereof prevents, blocks, inhibits, or reduces a *Klebsiella pneumonia* ST258 infection or other *Klebsiella pneumoniae* strains, thereby inhibiting or preventing a *Klebsiella pneumonia* ST258 or other *Klebsiella pneumoniae* strains infection. In some aspects. an anti-infective or antibiotic agent can also be administered or delivered to the subject in conjunction with the anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody or binding fragment thereof. In some aspects, the antibiotic agent can be ceftazidime-avibactam.

Any of the anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies disclosed herein may be administered before, during, after, or in various combinations relative to another treatment (e.g., anti-infective agent or antibiotic). The administrations may be in intervals ranging from concurrently to minutes to days to weeks before or after one another. In some aspects, in which the antibody is provided to a patient separately from an anti-infective agent or antibiotic, it would be generally ensured that a significant period of time did not expire between the time of each delivery, such that the administered compounds would still be able to exert an advantageously combined effect for the patient Illustratively, in such instances, it is contemplated that one may provide a patient with the antibody and the anti-infective therapy or antibiotic within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In some aspects, a course of treatment or treatment cycle will last 1-90 days or more (this range includes intervening days and the last day). It is contemplated that one agent may be given on any day of day 1 to day 90 (this such range includes intervening days and the last day) or any combination thereof, and another agent is given on any day of day 1 to day 90 (this such range includes intervening days and the last day) or any combination thereof. Within a single day (24-hour period), the patient may be given one or multiple administrations of the agent(s). Moreover, after a course of treatment, it is contemplated that there may be a period of time at which no second agent (e.g., anti-cancer treatment or immunosuppressant agent) is administered. This time period may last, for example, for 1-7 days, and/or 1-5 weeks, and/or 1-12 months or more (this such range includes intervening days and the upper time point), depending on the condition of the patient, such as prognosis, strength, health, etc. Treatment cycles would be repeated as necessary. Various combinations of treatments may be employed. In the representative examples of combination treatment regimens shown below, an antibody, such as anti-*Klebsiella pneumoniae* sequence type 258 wzi50, wzi154 or wzi29 capsular polysaccharide antibody or binding fragment thereof is represented by "A" and an anti-cancer therapy is represented by "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A.

Administration of any antibody or therapy as described herein to a patient will follow general protocols for the administration of such compounds, taking into account the toxicity, if any, of the agents. Therefore, in some aspects there is a step of monitoring adverse events and toxicity, particularly those that may be attributable to combination therapy.

In some aspects, methods are disclosed comprising administering an anti-*Klebsiella pneumonlae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody alone or in combination with another agent (e.g., anti-infective agent or antibiotic) to a subject in need thereof, i.e., a subject with a *Klebsiella pneumonia* ST258 or other *Klebsiella pneumoniae* strain infection or exposed to *Klebsiella pneumonia* ST258 or other *Klebsiella pneumoniae* strains). Prior to administration of the anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody, a sample of the subject's blood or one or more symptoms associated with a *Klebsiella pneumonia* ST258 or other *Klebsiella pneumoniae* strains) infection may be evaluated for the presence or level of a *Klebsiella pneumonia* ST258. If the results of such an evaluation reveals that the subject's blood or symptoms associated with the a *Klebsiella pneumonia* ST258 or other *Klebsiella pneumoniae* strains infection is positive for *Klebsiella pneumonia* ST258 or other *Klebsiella pneumoniae* strains or the level of *Klebsiella pneumonia* ST258 or other *Klebsiella pneumoniae* strains is increased compared to a reference sample or prior sample from the same subject, the subject would be selected for treatment based on the likelihood that subject's *Klebsiella pneumonia* ST258 or other *Klebsiella pneumoniae* strains blood sample or disease state or condition would be more amenable to treatment with the anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody and treatment may proceed with a more likely beneficial outcome. A medical professional or physician may advise the subject to proceed with the anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody treatment method, and the subject may decide to proceed with treatment based on the advice of the medical professional or physician. In addition, during the course of treatment, the subject's lungs or lung cells or blood cells may be assayed for the presence of *Klebsiella pneumonia* ST258 or other *Klebsiella pneumoniae* strains as a way to monitor the progress or effectiveness of treatment. If the assay shows a change, loss, or decrease, for example, in *Klebsiella pneumonia* ST258 or other *Klebsiella pneumoniae* strains on the subject's lungs, lung cells or blood cells, a decision may be taken by the medical professional in conjunction with the subject as to whether the treatment should continue or be altered in some fashion, e.g., a higher dosage, the addition of another anti-infective agent or therapy or antibiotic, and the like.

Anti-infective agents. A wide variety of anti-infective agents may be used in accordance with the treatment or therapeutic methods as described herein. The term "anti-infective" refers to the use of drugs to prevent or treat an infection or capable of inhibiting the spread of an infectious organism or by killing the infectious organism. A "anti-infective agent" connotes a compound or composition that is administered in the prevention or treatment of an infection. Examples of anti-infective agents include antibacterials, antivirals, antifungals and antiparasitic medications. Antibiotics can be divided into two classes based on their mechanism of action. Bactericidal antibiotics kill bacteria; and bacteriostatic antibiotics inhibit their growth or reproduction.

Nonlimiting examples of antibiotic agents include oral quinolones, imipenem, aztreonam, intravenous aminoglycosides, third generation cephalosporins, piperacillin/tazobactam colistin, tigecycline, gentamicin, ceftazdime-avibactam, and carbapenem, and pharmaceutically acceptable salts, acids, or derivatives of any of the above.

Protein Purification. Protein, including antibody and, particularly, anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody, purification techniques are well known to those of skill in the art. These techniques involve, at one level, the homogenization and crude fractionation of the cells, tissue, or organ into polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure protein or peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, the order of conducting the various purification steps may be changed, and/or certain steps may be omitted, and still result in a suitable method for the preparation of a substantially purified polypeptide.

A purified polypeptide, such as an anti-*Klebsiella pneumonmae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody as described herein, refers to a polypeptide which is isolatable or isolated from other components and purified to any degree relative to its naturally-obtainable state. An isolated or purified polypeptide, therefore, also refers to a polypeptide free from the environment in which it may naturally occur, e.g., cells, tissues, organs, biological samples, and the like. Generally, "purified" will refer to a polypeptide composition that has been subjected to fractionation to remove various other components, and which composition substantially retains its expressed biological activity. A "substantially purified" composition refers to one in which the polypeptide forms the major component of the composition, and as such, constitutes about 50%, about 60%, about 70%, about 80%, about 90%, about 95%, or more of the protein component of the composition.

Various methods for quantifying the degree of purification of polypeptides, such as antibody proteins, are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed polypeptide exhibits a detectable activity.

There is no general requirement that the polypeptide will always be provided in its most purified state. Indeed, it is contemplated that less substantially purified products may have utility in some aspects. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance (protein) to be isolated and a molecule to which it can specifically bind, e.g., a receptor-ligand type of interaction. The column material (resin) is synthesized by covalently coupling one of the binding partners to an insoluble matrix. The column material is then able to specifically adsorb the substance from the solution that is passed over the column resin. Elution occurs by changing the conditions to those in which binding will be disrupted/will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding; however, elution of the bound substance should occur without destroying the sample protein desired or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates, resulting in the separation of a solution of particles based on size. Provided that all of the particles are loaded simultaneously or near simultaneously, particles of the same size should elute together.

High-performance (aka high-pressure) liquid chromatography (HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used Pharmaceutical Preparations. Where clinical application of a pharmaceutical composition comprising an anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody is undertaken, it is generally beneficial to prepare a pharmaceutical or therapeutic composition appropriate for the intended application. In general, pharmaceutical compositions can comprise an effective amount of one or more polypeptides or additional agents dissolved or dispersed in a pharmaceutically acceptable carrier. In some aspects, pharmaceutical compositions may comprise, for example, at least about 0.1% of a polypeptide or antibody. In some aspects, a polypeptide or antibody may comprise between about 2% to about 75% of the weight of the unit, or between about 25% to about 60%, for example, and any range derivable there between, including the upper and lower values. The amount of active compound(s) in each therapeutically useful composition may be prepared in such a way that a suitable dosage will be obtained in any given unit dose. Factors, such as solubility, bioavailability, biological half-life, route of administration, product shelf life, as well as other pharmacological considerations, are contemplated by one skilled in the art of preparing such pharmaceutical formulations, and as such, a variety of dosages and treatment regimens may be desirable.

Further in some aspects, the composition suitable for administration can be provided in a pharmaceutically acceptable carrier with or without an inert diluent. The carrier should be assimilable and include liquid, semi-solid, e.g., gels or pastes, or solid carriers. Examples of carriers or diluents include but are not limited to fats, oils, water, saline solutions, lipids, liposomes, resins, binders, fillers, and the like, or combinations thereof. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate). dispersion media, coatings (e.g., lecithin), surfactants, antioxidants, preservatives (e.g., antibacterial or antifungal agents, antioxidants, chelating agents, inert gases, parabens (e.g., methylparabens, propylparabens), chlorobutanol, phenol, sorbic acid. thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc.), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in an administrable composition for the practice of the methods is appropriate. The pH and exact concentration of the various components in a pharmaceutical composition are adjusted according to well-known parameters. In some aspects, the composition can be combined with the carrier in any convenient and practical manner, i.e., by solution, suspension, emulsification, admixture, encapsulation, absorption, grinding, and the like. Such procedures are routine for those skilled in the art.

In some aspects, the compositions may comprise different types of carriers depending on whether they are to be administered in solid, liquid, or aerosol form, and whether it needs to be sterile for the route of administration, such as injection. The compositions can be formulated for administration intravenously. intradermally, transdermally, intrathecally, intra-arterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art. See, for example, *Remington's Pharmaceutical Sciences,* 18th Ed., 1990. Typically, such compositions can be prepared as either liquid solutions or suspensions; solid or reconstitutable forms suitable for use to prepare solutions or suspensions upon the addition of a liquid prior to injection can also be prepared; and, the preparations can also be emulsified.

In some aspects, the compositions disclosed herein can be formulated for administration as a vaccine.

The antibodies may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups may also be derived from inorganic bases, such as, for example, sodium, potassium, ammonium, calcium, or ferric hydroxides; or such organic bases as isopropylamine, trimethylamine, histidine, or procaine.

In some aspects, a pharmaceutical lipid vehicle composition that includes polypeptides. one or more lipids, and an aqueous solvent may be used. As used herein, the term "lipid" refers to any of a broad range of substances that are characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats. phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods. One of ordinary skill in the art would be familiar with the range of techniques that can be employed for dispersing a composition in a lipid vehicle. For example, the antibody may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic antibody or composition containing the therapeutic antibody calculated to produce the desired responses discussed above in association with its administration, i.e., the appropriate route and treatment regimen. The quantity to be administered, both according to number of treatments and unit dose, depends on the effect desired. The actual dosage amount of a composition as described herein that can be administered to a patient or subject can be determined by physical and physiological factors, such as body weight, the age, health, and sex of the subject, the type of disease being treated, the extent of disease penetration, previous or concurrent therapeutic interventions, idiopathy of the subject, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The foregoing doses include amounts between those indicated and are intended to also include the lower and upper values of the ranges. The practitioner responsible for administration will, in any event, determine the concentration of active ingredient(s) in a composition and appropriate dose(s) for the individual subject.

The particular nature of the therapeutic composition or preparation is not intended to be limiting. For example, suitable compositions may be provided in formulations together with physiologically tolerable liquid, gel, or solid carriers, diluents, and excipients. In some aspects, the therapeutic preparations may be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects, as described supra.

Fusions and Conjugates

The anti-*Klebsiella pneumoniae* sequence type 258 wzi50, wzi154 or wzi29 capsular polysaccharide antibodies or other anti-*Klebsiella pneumonia* e sequence type 258 wzi50, wzi154 or wzi29 capsular polysaccharide antibodies or polypeptides disclosed herein can also be expressed as fusion proteins with other proteins or chemically conjugated to another moiety. In some aspects, the antibodies or polypeptides can have an Fc portion that can be varied by isotype or subclass, can be a chimeric or hybrid, and/or can be modified, for example to improve effector functions, control half-life or tissue accessibility, augment biophysical characteristics, such as stability, and improve efficiency of production, which can be associated with cost reductions. Many modifications useful in the construction of fusion proteins and methods for making them are known in the art, for example, as reported by Mueller, J. P. et al., 1997*, Mol. Immun.* 34(6):441-452; Swann, P. G., 2008*, Curr. Opin. Immunol.,* 20:493-499; and Presta, L. G., 2008*, Curr. Opin. Immunol.,* 20:460-470. In some aspects, the Fc region can be the native IgG1, IgG2, or IgG4 Fc region of the antibody. In some aspects, the Fc region can be a hybrid, for example, a chimera containing IgG2/IgG4 Fc constant regions. Modifications to the Fc region include, but are not limited to, IgG4 modified to prevent binding to Fc gamma receptors and complement; IgG1 modified to improve binding to one or more Fc gamma receptors; IgG1 modified to minimize effector function (amino acid changes); and IgG1 with altered pH-dependent binding to FcRn. The Fc region can include the entire hinge region, or less than the entire hinge region of the antibody.

In some aspects, IgG2-4 hybrids and IgG4 mutants have reduced binding to FcR which can increase their half-life. Representative IG2-4 hybrids and IgG4 mutants are described, for example, in Angal et al., 1993*, Molec. Immunol.,* 30(1):105-108; Mueller et al., 1997*, Mol. Immun.,* 34(6):441-452; and U.S. Pat. No. 6,982,323; all of which are hereby incorporated by references in their entireties. In some aspects, the IgG1 and/or IgG2 domain can be deleted. For example, Angal et al., Id., describe proteins in which IgG1 and IgG2 domains have serine 241 replaced with a proline. In some aspects, fusion proteins or polypeptides having at least 10, at least 20, at least 30, at least 40, at least 50, at least 60, at least 70, at least 80, at least 90 or at least 100 amino acids are contemplated.

In some aspects, anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies or polypeptides can be linked to or covalently bind or form a complex with at least one moiety. Such a moiety may be, but is not limited to, one that increases the efficacy of the antibody as a diagnostic or a therapeutic agent. In some aspects, the moiety can be an imaging agent, a toxin, a therapeutic enzyme, an antibiotic, a radio-labeled nucleotide, a chemotherapeutic agent, and the like.

In some aspects, antibodies and polypeptides as described herein may be conjugated to a marker, such as a peptide, to facilitate purification. In some aspects, the marker can be a hexa-histidine peptide, i.e., the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some aspects, the moiety conjugated to the antibodies and polypeptides as described herein can be an imaging agent that can be detected in an assay. Such imaging agents can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, or colored particles or ligands, such as biotin. In some aspects, suitable enzymes include, but are not limited to, horseradish peroxidase, alkaline phosphatase, beta-galactosidase, or acetylcholinesterase; prosthetic group complexes include, but are not limited to, streptavidin/biotin and avidin/biotin; fluorescent materials include, but are not limited to, umbelliferone, fluorescein, fluorescein isothiocyanate, rhodamine, dichlorotriazinylamine fluorescein, dansylchloride or phycoerythrin; luminescent materials include, but are not limited to, luminol; bioluminescent materials include, but are not limited to, luciferase, luciferin, and aequorin; radioactive materials include, but are not limited to, bismuth ($^{213}$Bi), carbon ($^{14}$C), chromium ($^{51}$Cr), cobalt ($^{57}$Co), fluorine ($^{18}$F), gadolinium ($^{53}$Gd, $^{159}$Gd) gallium ($^{68}$Ga, $^{67}$Ga), germanium ($^{68}$Ge), holmium ($^{166}$Ho), indium ($^{115}$In, $^{113}$In, $^{112}$I, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The imaging agent can be conjugated to the antibodies or polypeptides described herein either directly or indirectly through an intermediate (such as, for example, a linker known in the art) using techniques known in the art. See, for example, U.S. Pat. No. 4,741,900 which reports on metal ions that can be conjugated to antibodies and other molecules as described herein for use as diagnostics. Some conjugation methods involve the use of a metal chelate complex employing, for example, an organic chelating agent, such as diethylenetriaminepentaacetic acid anhydride (DTPA); ethylenetriaminetetraacetic acid; N-chloro-p-toluenesulfonamide; and/or tetrachloro-3-6α-diphenylglycouril-3, attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

In some aspects, the anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies) as described herein can be conjugated to a second antibody to form an antibody heteroconjugate, for example, as described in U.S. Pat. No. 4,676,980. Such heteroconjugate antibodies can additionally bind to haptens (e.g., fluorescein), or to cellular markers.

In some aspects, the anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody or polypeptides described herein can also be attached to solid supports, which can be useful for carrying out immunoassays or purification of the target antigen or of other molecules that are capable of binding to the target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

Kits and Diagnostics

Disclosed herein are kits comprising therapeutic agents and/or other therapeutic and delivery agents. In some aspects, the kits can be used for preparing and/or administering a therapy involving the anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies described herein. The kits can comprise one or more sealed vials containing any of the pharmaceutical compositions as described herein. The kits can include, for example, at least one anti-*Klebsiella pneumoniae* sequence type 258 wzi50, wzi154 or wzi29 capsular polysaccharide antibody or other anti-*Klebsiella pneumoniae* sequence type 258 wzi50, wzi154 or wzi29 capsular polysaccharide antibody, as well as reagents to prepare, formulate, and/or administer one or more anti-*Klebsiella pneumoniae* sequence type 258 wzi50, wzi154 or wzi29 capsular polysaccharide antibodies or other anti-*Klebsiella pneumoniae* sequence type 258 wzi50, wzi154 or wzi29 capsular polysaccharide antibodies or to perform one or more steps of the described methods. In some aspects, the kits can also comprise a suitable container means, which is a container that will not react with components of the kit, such as an Eppendorf tube, an assay plate, a syringe, a bottle, or a tube. The container may be made from sterilizable materials, such as plastic or glass.

The kits can further include an instruction sheet that outlines the procedural steps of the methods set forth herein, and will follow substantially the same procedures as described herein or are known to those of ordinary skill. The instruction information may be in a computer readable medium containing machine-readable instructions that, when executed using a computer, cause the display of a real or virtual procedure of delivering a pharmaceutically effective amount of the therapeutic agent.

EXAMPLES

Example 1: An Anti-Capsular Antibody that Cross Protects Against Clade 1 Carbapenem-Resistant *Klebsiella pneumoniae*

Previous data examining human antibodies responses to clinical CR-Kp infection demonstrated wide cross reactivity of patient-derived CPS-specific antibodies to non-identical strains of the same wzi-type. Importantly, the data indicate that polyclonal serum from patients who recovered from wzi50 CR-Kp mediated infection conveyed protective immunity against wzi29 and wzi154 strains as well. This data suggested that there could be a shared epitope between wzi50, wzi29 and wzi154 CPS that elicits cross-protective antibodies. Thus, described herein are monoclonal antibodies developed by vaccinating with wzi50 type CPS and testing whether these monoclonal antibodies mediate a cross-protective effect.

Also described herein is the characterization of a monoclonal antibody (mAb 24D11) that binds purified wzi50 type CPS of CR-Kp. The data demonstrates that mAb 24D11 modulates protection against infection in vitro and in vivo. This is the first monoclonal antibody that presents broad activity against several dominant wzi types that are expressed by the majority of ST258 strains.

Results. Generation of monoclonal antibody against wzi50 capsular polysaccharide. With the knowledge that anti-wzi50 patient antibodies cross-react and protect against other capsular types, wzi50 was utilized as an immunogen to develop monoclonal antibodies. Balb/c mice were vaccinated with unconjugated purified wzi50 CPS, or with wzi50 CPS conjugated to *Bacillus anthracis* Protective Antigen (wzi50-BaPA), in addition to Freund's complete adjuvant to improve responses. Titer responses were poor for both groups of mice, requiring additional booster doses of CPS with adjuvant at 6 and 8 weeks to attempt to achieve sufficient titers (>1:10,000). This regiment was still insufficient to elicit strong anti-capsular titers in the BaPA-CPS vaccinated mice (≤1:6,400), whereas mice vaccinated with unconjugated wzi50 reached and maintained strong titers (>1:10,000) by 6 weeks post initial vaccination. As a result, the mice that were vaccinated with the unconjugated CPS for splenic fusions were used. Serum from these mice was also found to bind wzi29 CPS at a titer greater than 1:10,000, and wzi154 CPS at a titer higher than serum of the mice vaccinated with conjugated wzi50 CPS (FIG. 1B).

Splenic fusions with two hybridoma cell lines were screened for activity against wzi50, and 3 positive clones with NSO$^{bcl2}$ backgrounds were identified for downstream subcloning and soft agar selection. Of these, IgG2b-producing hybridoma 24D11 was selected and subcloned for further study, as it had significantly superior activity relative to the other 2 clones. The binding $EC_{50}$ of monoclonal antibody 24D11 to wzi50 was determined to be 4.72 nM by ELISA.

Figure 2A:
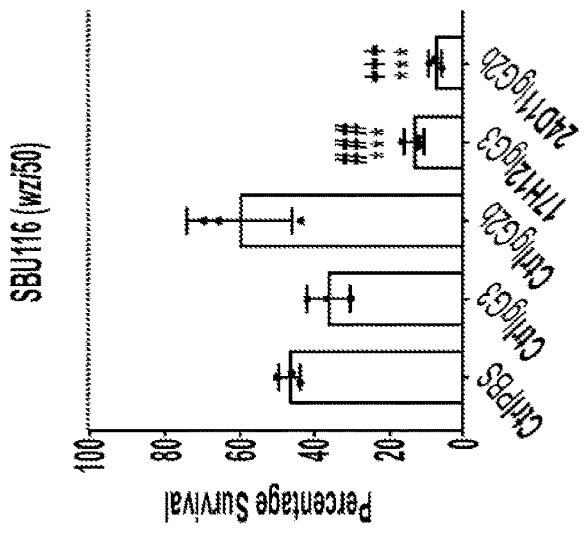
FIGS. 2A-C show that monoclonal antibody 24D11 promotes killing of CR-Kp of multiple serotypes in healthy donor blood. Whole blood samples were treated with isotype control or with 40 μg/ml of mAb 24D11 (mIgG2b) or 17H12 (mIgG3) and simultaneously inoculated with 10 CFU/ml live carbapenem-resistant *K. pneumoniae* strains: SBU116, which possesses the wzi50 allele (FIG. 2A), MMC36, which possesses the wzi29 allele (FIG. 2B), and MMC34 (FIG. 2C), which possesses the wzi154 allele. CFU/ml/survival values were determined after 1 hour in culture and plotted as a percentage of the initial starting inoculum (dotted line). The experiment was repeated as three separate replicates, which each symbol representing one replicate. For the studies, bars depict means, and SDs. Overall differences in percent survival between treatment groups (n=3 per group) were assessed for significance by one-way ANOVA with multiple-comparison correction. Symbols representing p-values for comparisons between antibody groups and PBS (black *), between monoclonal antibody 17H12 and its mIgG3 control (#), and between monoclonal antibody 24D11 and its mIgG2b control (+) are as follows: * if p<0.05,  if p<0.01, * if p<0.001.
Figure 2B:
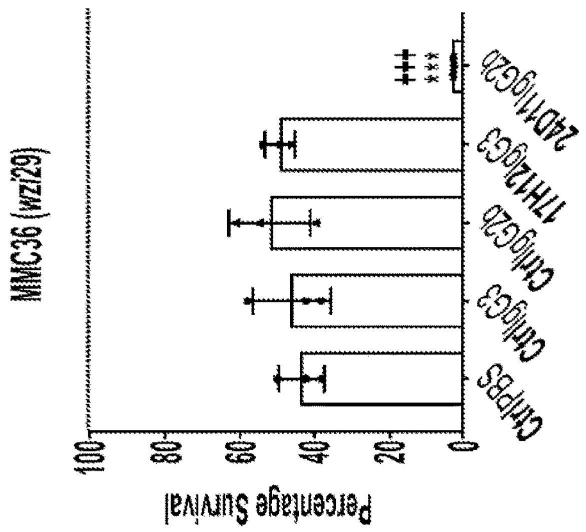
Figure 2C:
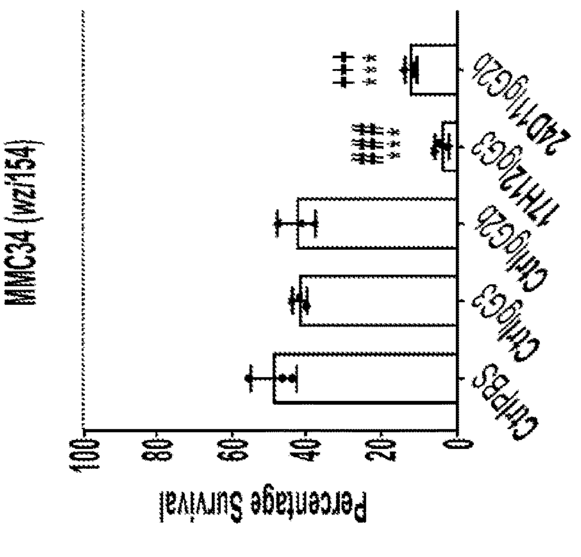
Figure 3:
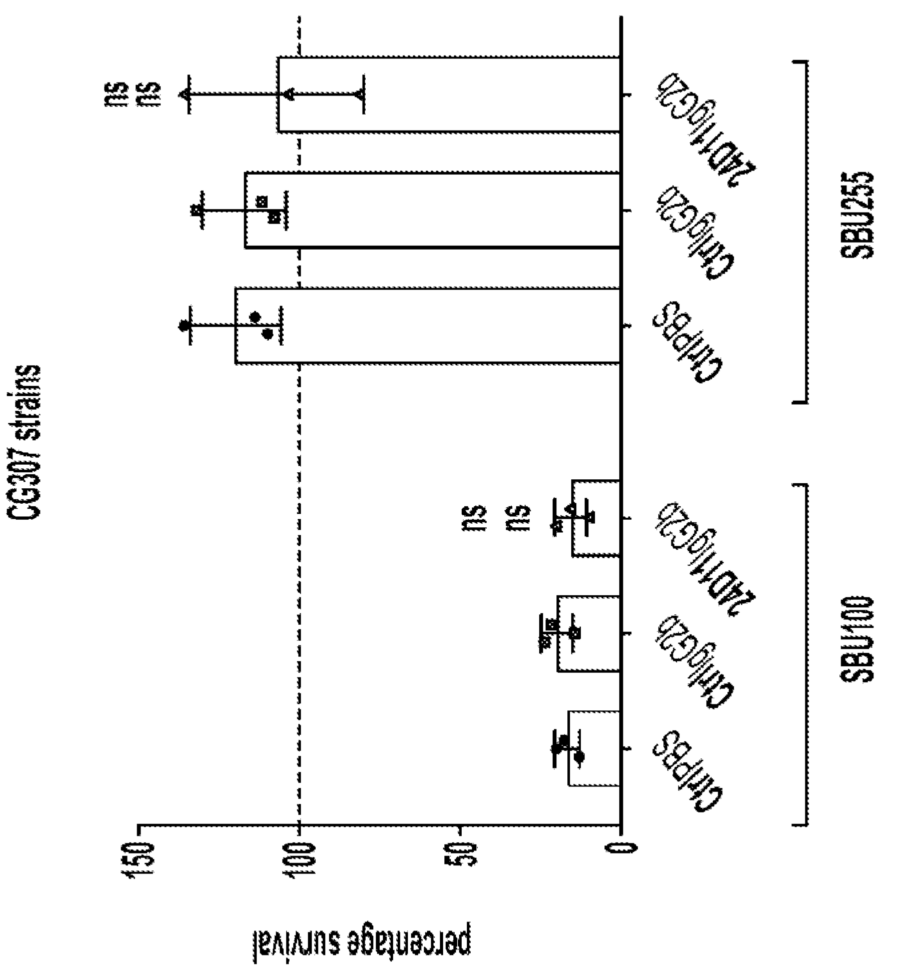
FIG. 3 shows that monoclonal antibody 24D11 is specific to ST258 CR-Kp strains, therefore it does not mediate killing of ST307 CR-Kp strains in whole blood. Monoclonal antibody 24D11 failed to promote whole blood killing of non-ST258 strains SBU100 and SBU255 (ST307 strains with wzi types 173). CFU counts after one hour of incubation with antibody, control, or PBS are plotted relative to initial inoculum, with symbols indicating CFU counts of each of three independent experiments. CFU/ml/survival values were determined after 1 hour in culture and plotted as a percentage of the initial starting inoculum (black dotted line). The experiment was repeated as three separate replicates, with each symbol representing one replicate. For the studies, bars depict means and SDs. Overall differences in percent survival between treatment groups (n=3 per group) were assessed for significance by one-way ANOVA with multiple-comparison correction. Comparisons between antibody groups and PBS (circles), and between 24D11 and its mIgG2b control (squares) were not significant (ns).

Anti-wzi5 antibody 24D11 mediates whole-blood killing of multiple CR-Kp strains. To explore the anti-infective effects of mAb 24D11, the antibody-mediated killing of multiple strains of CR-Kp was examined in whole blood. As a control, murine IgG3 (mIgG3) 17H12, developed against CPS of a wzi154-carrying CR-Kp strain was used. The CFU of the tested CR-Kp strains dropped to undetectable levels regardless of condition at 2h. At 1 hr, both monoclonal antibodies 24D11 and 17H12 reduced survival of wzi50-carrying SBU116 (~83% reduction in bacterial survival) significantly more so than their corresponding control antibodies did (p<0.0001) (FIG. 2A). Interestingly monoclonal antibody 24D11 cross-reacted and significantly reduced wzi29 MMC36 CR-Kp bacterial levels in whole blood by 90% (p<0.0001), whereas 17H12 did not significantly affect bacterial levels relative to its control antibody (FIG. 2B). Additionally, both monoclonal antibodies 24D11 and 17H12 promoted significant killing of wzi154-carrying MMC34 (~90% reduction in bacterial survival) when compared to their isotype controls (p<0.0001) (FIG. 2C). In addition, utilized CR-Kp SBU255, a strain belonging to the emerging clonal group CG307 Kp, which is genetically distinct from the ST258 clonal group and expresses an unrelated wzi173 CPS, was also used to test the specificity of monoclonal antibody 24D11. Monoclonal antibody 24D11 did not promote the killing of both CG307 CR-Kp strains (SBU100 and SBU255) in the whole blood assay at 1 hr (FIG. 3).

Figure 4A:
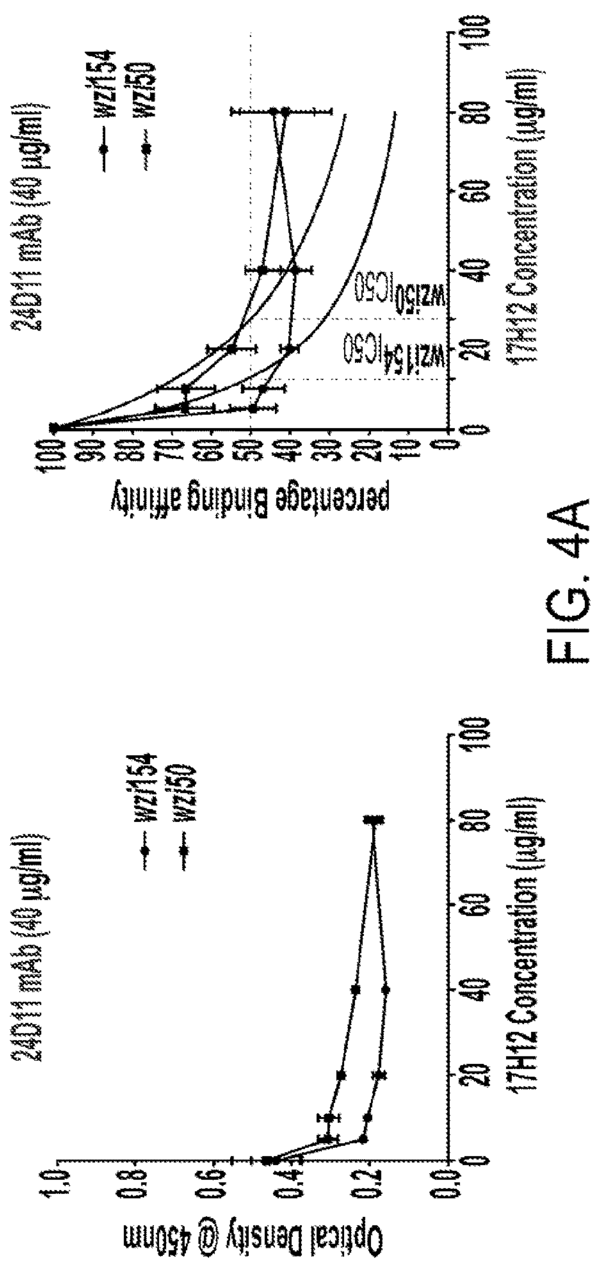
FIGS. 4A-B show the binding of 24D11 and 17H12 monoclonal antibodies against wzi50 and wzi154 CPS determined by competitive indirect-ELISA.
Figure 4B:
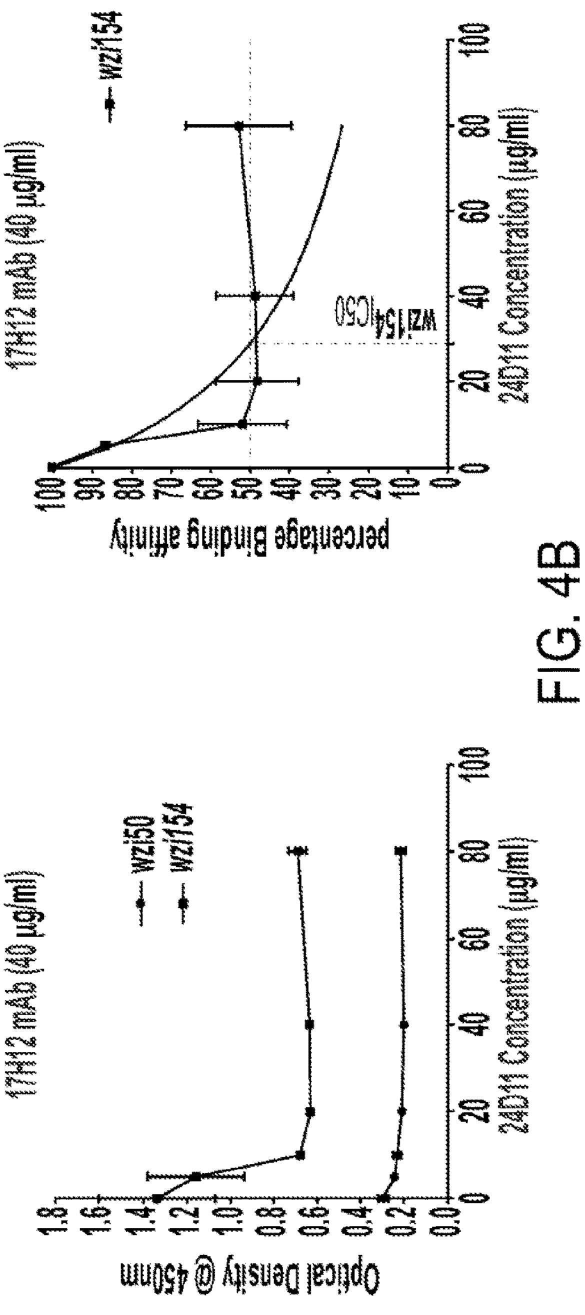

Furthermore, increased cross-reactive killing of MMC34 by monoclonal antibody 24D11 and of SBU116 by monoclonal antibody17H12 relative to controls was also observed (FIGS. 2A and 2C) (p<0.0001). This observation led to investigate whether both mAbs bind to any conserved epitopes on wzi50 and wzi154 CPS by performing modified competitive ELISA assays. Binding curves indicated that monoclonal antibody 17H12 began to compete with monoclonal antibody 24D11 binding to wzi50 CPS and wzi154 CPS at 5 μg/ml, whereas monoclonal antibody 24D11 began to compete with monoclonal antibody 17H12 binding to wzi154 at 10 μg/ml (FIG. 4).

Figure 5:
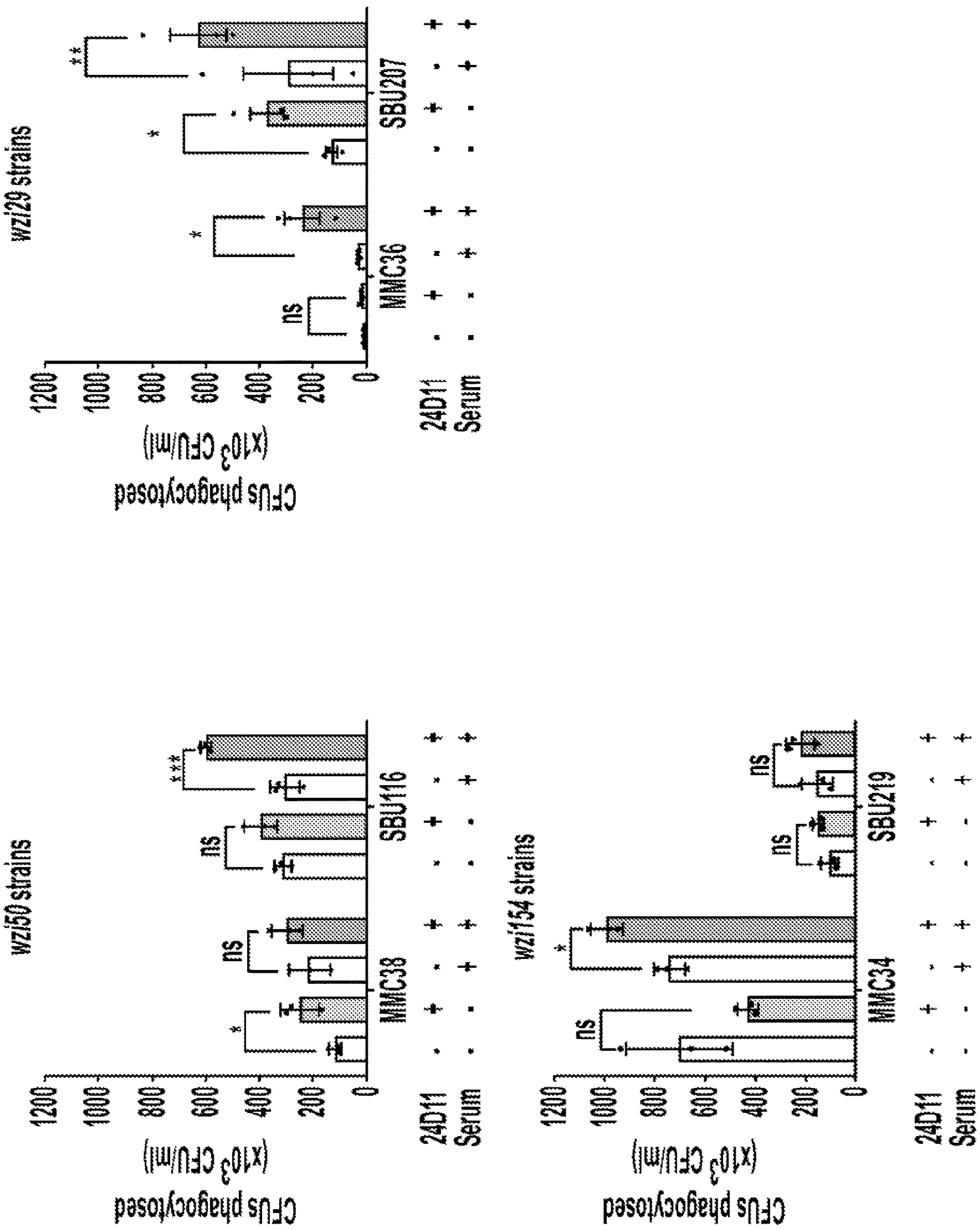
FIG. 5 shows that monoclonal antibody 24D11 promotes macrophage-mediated opsonophagocytosis of CR-Kp strains across several wzi-types. Opsonophagocytic uptake by J774.A1 murine macrophage-like cells of wzi50 strains (MMC38 and SBU116), wzi29 strains (MMC36 and SBU207) and wzi154 strains (MMC34 and SBU219) pre-opsonized with or without monoclonal antibody 24D11 was measured after 1 hour in the presence or absence of normal human serum. The CFUs phagocytosed was calculated as the number of CFU recovered after washing and macrophage lysis. Bars depict means and SDs of three independent experiments, with wells performed in triplicate. Differences between the non-serum treated group with or without 24D11 (*) and differences between the NHS-treated group with or without 24D11 (black *) were assessed for significance by repeated-measures two-way ANOVA with results of Tukey's post hoc test for multiple comparisons displayed in the graph. p-values are replaced with ns if ≥0.05, * if <0.05,  if <0.01, and * if <0.001.

Monoclonal antibody 24D11 promoted cross-protective opsonophagocytosis of multiple CR-Kp strains. Macrophages and monocytes are important players in CR-Kp clearance, and the antibody-mediated opsonophagocytic uptake by macrophages is important to cell-mediated protection against CR-Kp. Therefore, the ability of monoclonal antibody 24D11 to promote opsonophagocytic uptake of different CR-Kp strains by mouse macrophage-like cell line J774A.1 was investigated. The data showed that monoclonal antibody 24D11 promoted opsonophagocytosis of 5/6 CR-Kp strains, including two wzi29 strains and one wzi154 strain (FIG. 5). Three of these five strains required serum for monoclonal antibody 24D11 to significantly improve opsonophagocytosis relative to controls (SBU116, MMC34, MMC36), while two strains (MMC38, SBU207) showed serum-independent promotion of opsonophagocytosis. For one strain (MMC38), opsonophagocytosis of CR-Kp by monoclonal antibody 24D11 did not differ with controls in the presence of serum, with opsonophagocytosis levels equivalent to those in the presence of monoclonal antibody 24D11 without serum (FIG. 5).

Figure 6:
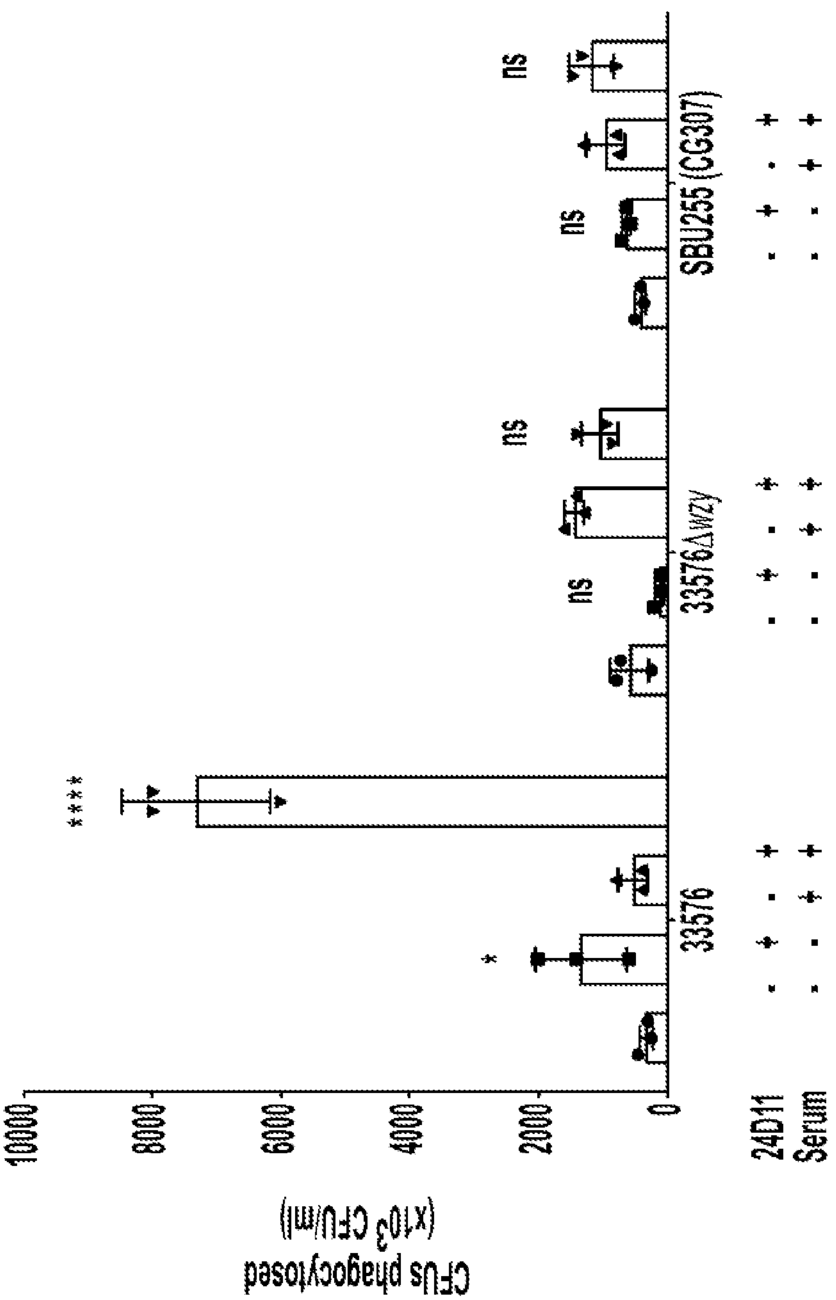
FIG. 6 shows that the coincubation with mAb 24D11 induces opsonophagocytosis of capsular ST258 CR-Kp strain, but not other CR-Kp strains tested due to its specificity. Monoclonal antibody 24D11 promoted the phagocytosis of wzi154 ST258 strain 33576 in the presence of serum relative to a PBS control but failed to do so for its a capsular variant 33576Δwzy or for ST307 strain SBU255. Raw CFU counts are plotted as Mean+−SD of three individual experiments with wells performed in triplicate. Phosphate-buffered saline (PBS) served as the negative controls for the assay. Overall differences between treatment groups were determined to be significant by repeated measures two-way ANOVA using Tukey's post hoc test, displayed in-graph. For the in-graph statistics, p-values displayed in black are comparisons to the PBS control. Data is shown as Mean±SD and p-values are replaced with ns if ≥0.05, * if <0.05,  if <0.01, * if <0.001, and **** if <0.0001.

To ensure that monoclonal antibody 24D11's cross-reactivity was dependent on the presence of CPS and not due to non-specific binding to the bacteria, its ability to promote opsonophagocytosis of CR-Kp 33576 (wzi54) and its a capsular mutant 33576Δwzy was tested (FIG. 6). Monoclonal antibody 24D11 mediated phagocytosis of the capsular 33576 bacteria but did not promote phagocytic uptake of the a capsular 33576Δwzy. Additionally, monoclonal antibody 24D11 when tested against CG307 strain SBU255, and did not promote phagocytosis of CG307 strain SBU255 (FIG. 6).

Figure 7A:
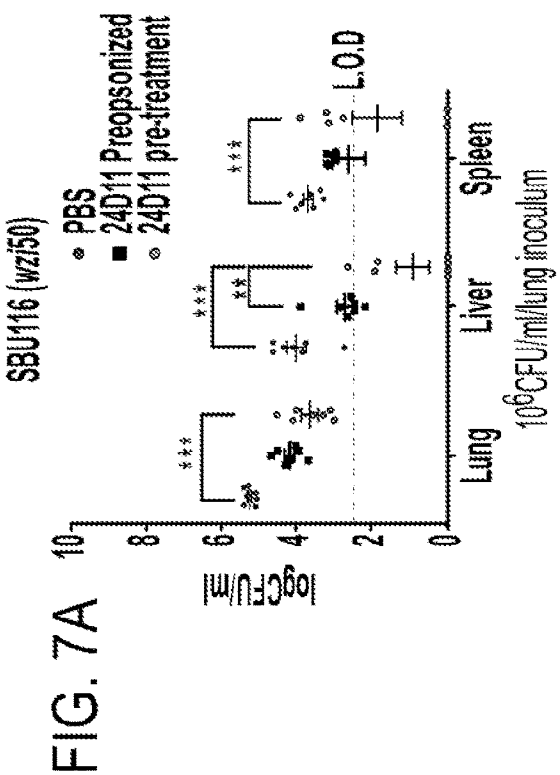
FIGS. 7A-D show that monoclonal antibody 24D11 exhibits potent protective efficacy in CR-Kp pulmonary infection when given prophylactically. Organ burden was measured in mice one day after infection with SBU116 (FIGS. 7A, 7B), MMC36 (FIG. 7C) and MMC34 (FIG. 7D) strains at indicated inoculums in the presence or absence of monoclonal antibody 24D11, either as a pre-opsonization mix with the bacterial prior to infection (40 μg/ml final concentration, squares), or as a prophylactic intraperitoneal dose four hours-prior to infection (10 mg/kg, circles). Symbols represent individual mice pooled from a single experiment, and bars represent means and SD. Differences between CFU between treatment groups were compared by assessed for significance by one-way ANOVA with results of Tukey's post hoc test for multiple comparisons displayed in the graph. Asterisks are used to indicate significant CFU differences to PBS or significant CFU differences between treatment groups are displayed if p-values were below 0.05 (*), 0.01 (), or 0.001 (*).
Figure 7B:
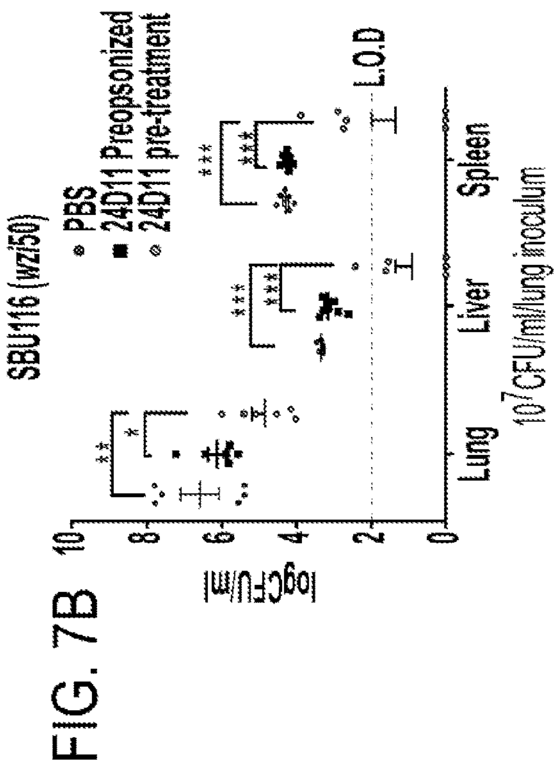
Figure 7C:
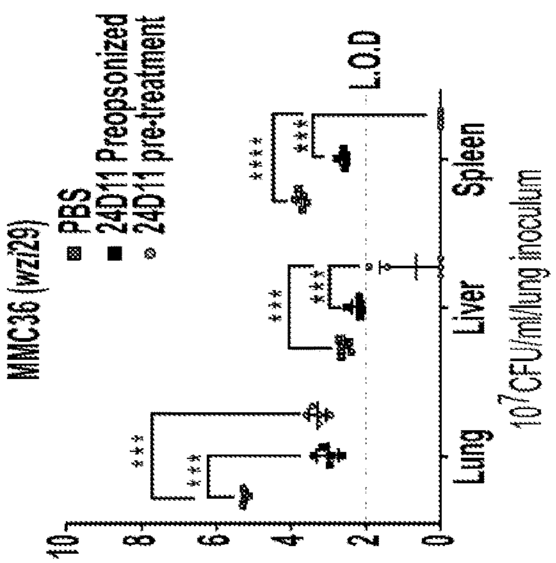
Figure 7D:
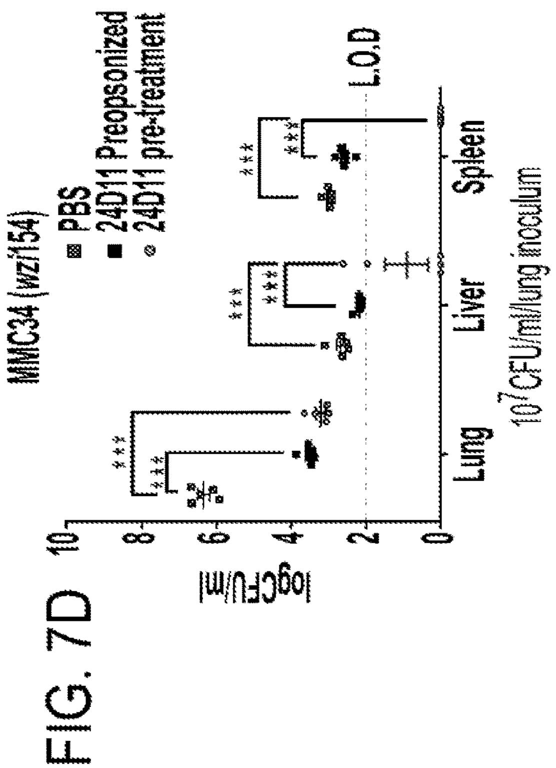

Intraperitoneal delivery of mAb 24D11 provides cross-protection in intratracheal lung infection model. Following the in vitro observation, the cross-protective efficacy of monoclonal antibody 24D11 was explored in vivo by testing its ability to reduce organ burden in mice intratracheally infected with wzi50, wzi29, or wzi154-carrying CR-Kp strains. For this investigation, a pre-opsonized model, and a prophylactic model were used where monoclonal antibody 24D11 was given intraperitoneally (IP) 4 hours prior to intratracheal (i.t) infection to explore whether monoclonal antibody 24D11 was able to decrease bacterial lung burden and dissemination in C57BL/6 mice (FIGS. 7A-D). Mice injected with $10^6$ CFU/inoculum pre-opsonized wzi50 SBU116 exhibited a moderate 1-$\log_{10}$ reduction in the lung with no effect on the dissemination of the bacteria to liver and spleen (FIG. 7A). Further, mice infected with $10^1$ CFU/inoculum pre-opsonized SBU116 also showed a decrease of 1-$\log_{10}$ in bacterial lung burden with no significant reduction observed on bacterial dissemination to liver or spleen (FIG. 7B). On the contrary, prophylactic administration of monoclonal antibody 24D11 prior to CR-Kp intratracheal infection significantly reduced the lung bacterial burden by 2-$\log_{10}$ and bacterial spread by 3-$\log_{10}$ for both inoculum of SBU116 (p<0.001) (FIGS. 7A-B). Furthermore, at high inoculum dose of SBU116, better lung CR-Kp clearance was observed as well as inhibition of bacterial spread in 3 out of 6 mice within the pre-treated group as compared to pre-opsonized group (FIGS. 7A-B). In mice infected with monoclonal antibody 24D11-opsonized wzi29 MMC36 strain (FIG. 7C) and wzi154 MMC34 strain (FIG. 7D), a more significant CFU reduction of 3-$\log_{10}$ and 2-login fold in lung tissue, respectively, was observed. Further, a moderate drop was shown in the bacterial load of liver and spleen in antibody opsonized MMC36- and MMC34-infected mice (FIGS. 7C-D). Pre-treatment with monoclonal antibody 24D11 had similar effect in the reduction of lung bacterial burden, but for both MMC36 (FIG. 7C) and MMC34 (FIG. 7D) most of the animals showed significant inhibition in bacterial dissemination when compared to their pre-opsonized counterparts (FIGS. 7C-D).

Figure 8A:
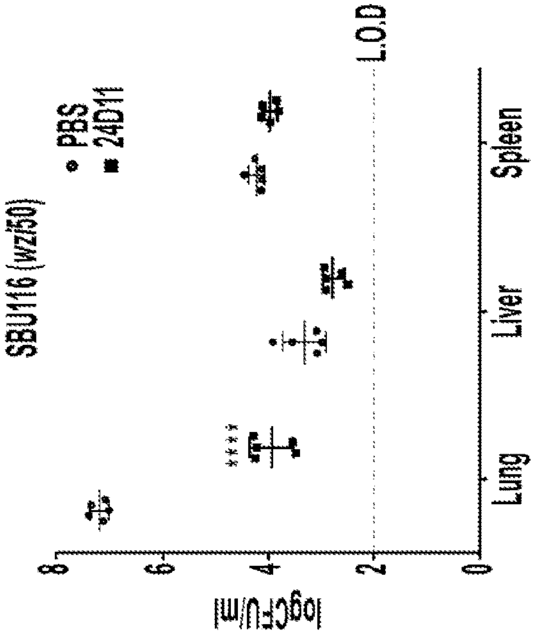
FIGS. 8A-C show that monoclonal antibody 24DI1 has protective efficacy when given post-infection. Organ burden was measured in mice one day after infection with 100 μl of $1\times10^8$ CFU/ml of SBU116 (FIG. 8A), MMC36 (FIG. 8B), and MMC34 (FIG. 8C) strains and then treated with intraperitoneal administration of PBS or monoclonal antibody 24D11 (10 mg/kg) four hours after infection. Symbols represent individual mice pooled from 2 individual experiments performed on two separate days. Bars represent means and SD. Differences between PBS group and monoclonal antibody 24D11 post-infection treatment group for SBU116, MMC36, and MMC34 were compared and assessed for significance by multiple t-tests (one unpaired t-tests per organ between two groups) with False Discovery Approach (FDR) at 1% displayed in the graph. Asterisks indicating significant CFU differences are displayed if p-values were below 0.05 (*), 0.01 (), 0.001 (*), or 0.0001 (****).
Figure 8B:
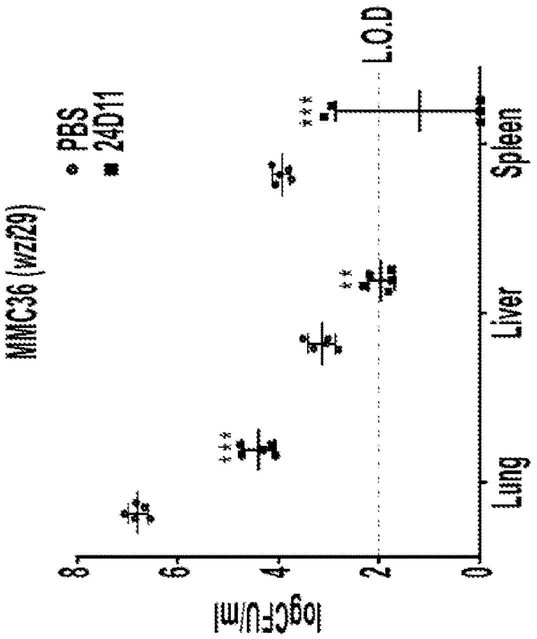
Figure 8C:
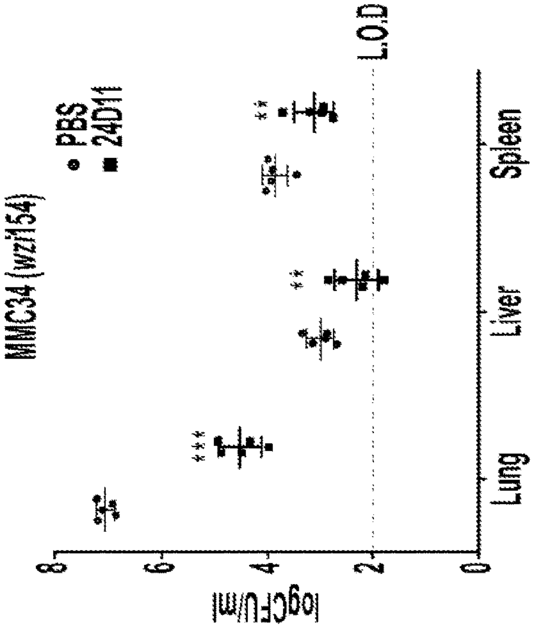

Next, it was investigated whether monoclonal antibody 24D11 also protected CR-Kp infected mice if treated intraperitoneally 4 hrs post-surgery (FIG. 8). To better mimic clinical therapy, CR-Kp infected mice were treated 4 hours after it. infection. These data demonstrated a significant drop of 3-login fold in the lung burden of SBU116 CR-Kp infected mice when compared to control group (FIG. 8A). In addition, SBU116 infected mice treated intraperitoneally with mAb 24D11 showed a moderate 1–$\log_{10}$ reduction in the bacterial CFU disseminated to other organs (FIG. 8A). For MMC29 (wzi29) and MMC34 (wzi154) infected mice IP-treatment with monoclonal antibody 24D11 post-i.t. surgery also demonstrated significant decrease of the bacterial organ load in lungs (FIGS. 8B-C). Furthermore, IP-treatment with mAb 24D11 prevented dissemination to the limit of detection to liver and spleen in 3 out of 5 MMC36 infected mice (FIG. 8B) and reduced bacterial spread to other affected-organs in MMC34 infected mice (FIG. 8C).

Figure 9A:
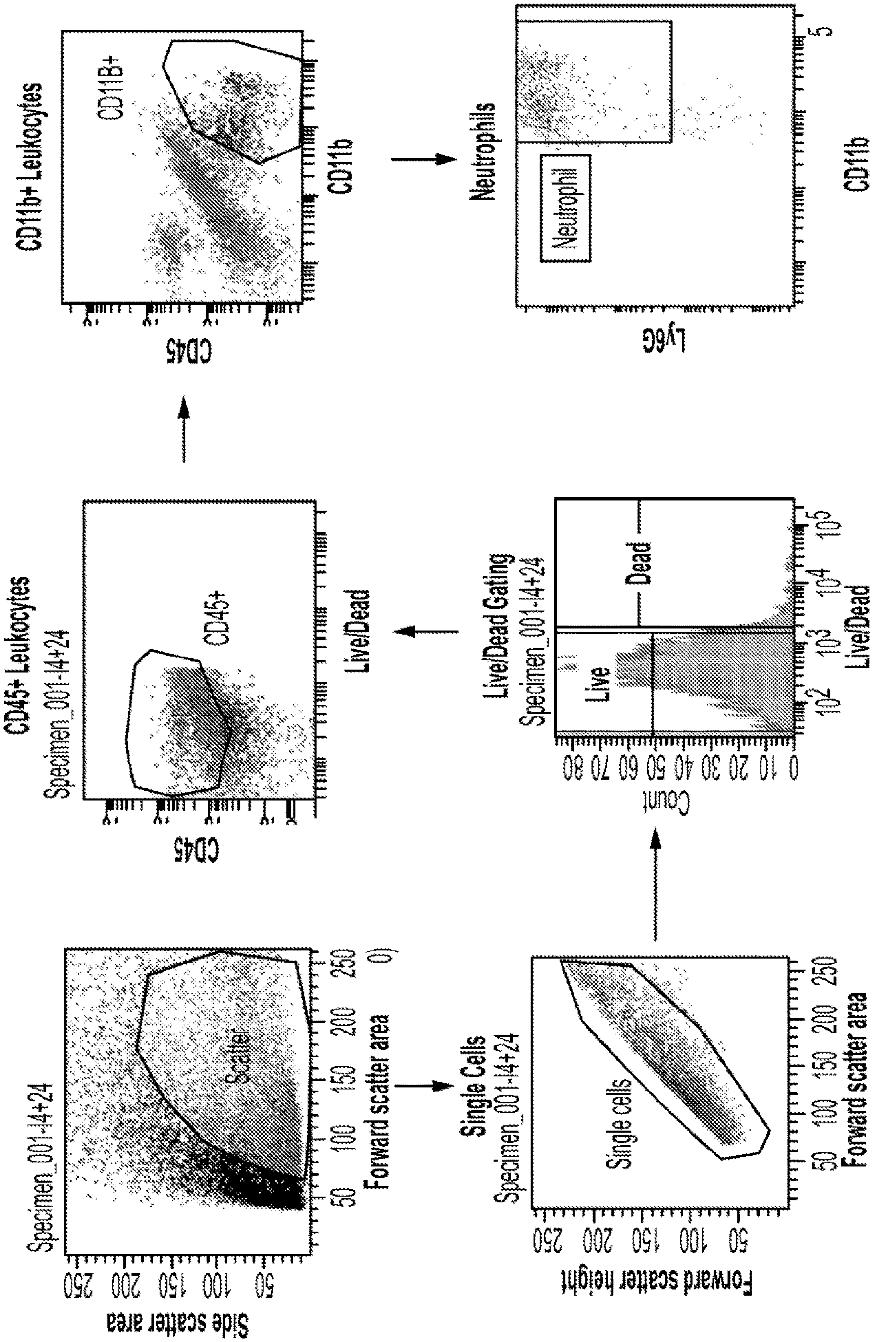
FIGS. 9A-E show that monoclonal antibody 24D11 exerts anti-CR-Kp efficacy in neutropenic mice. Cells were gated in an SSC-A and FSC-A dot plot to eliminate dead cells and aggregated cells. Single cells were gated in an FSC-H vs. FSC-A dot plot to eliminate doublets. Single cells were then gated on the Live/Dead Alexa 700 axis to eliminate dead cells: CD45+ live leukocytes were gated. CD45+CD11b+ leukocytes were gated and Ly6G+ gating on CD11b+ leukocytes were chosen to analyze neutrophils. Flow cytometry isotype control showing 0% of cells in the Ly6G+ Neutrophils gate. Percentage neutrophils from each treatment group are shown in the Ly6G+ Neutrophils gate. FSC-A: Forward scatter area. FSC-H: Forward scatter height. SSC-A: Side scatter area (FIG. 9A).
Figure 9A:
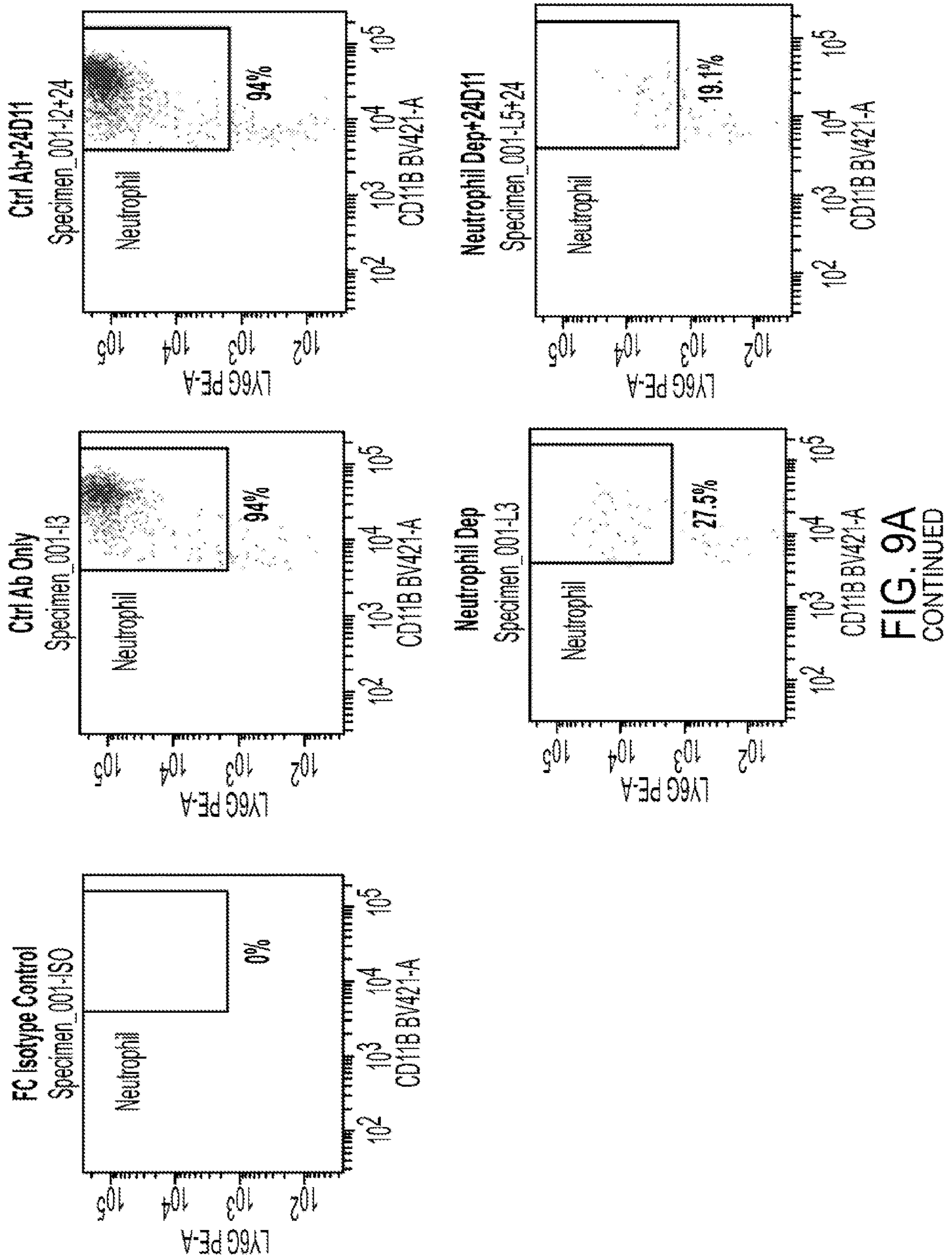
Figure 9B:
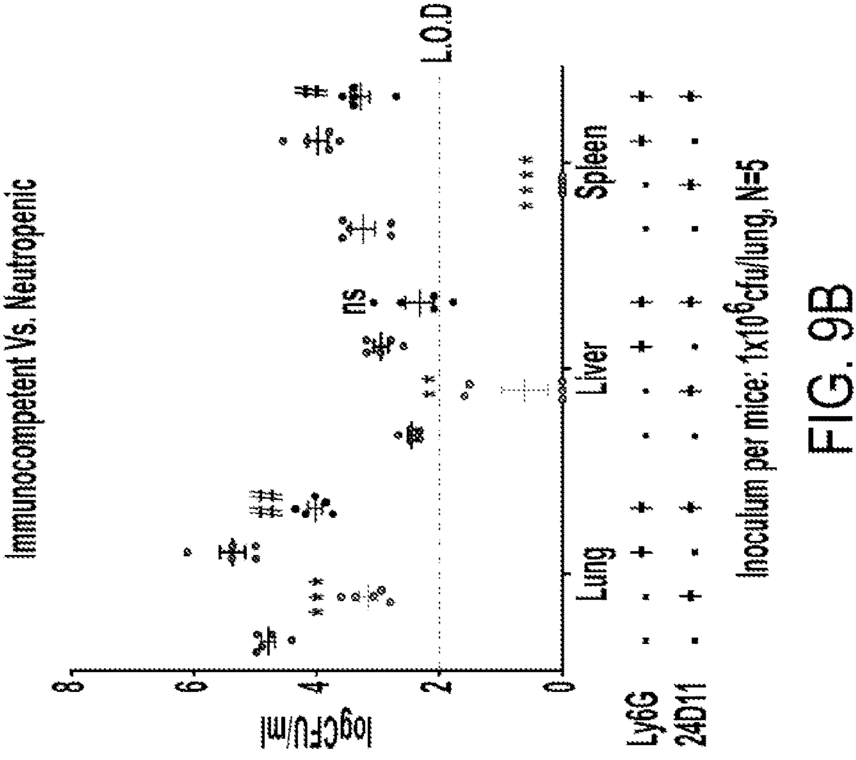
Figure 10:
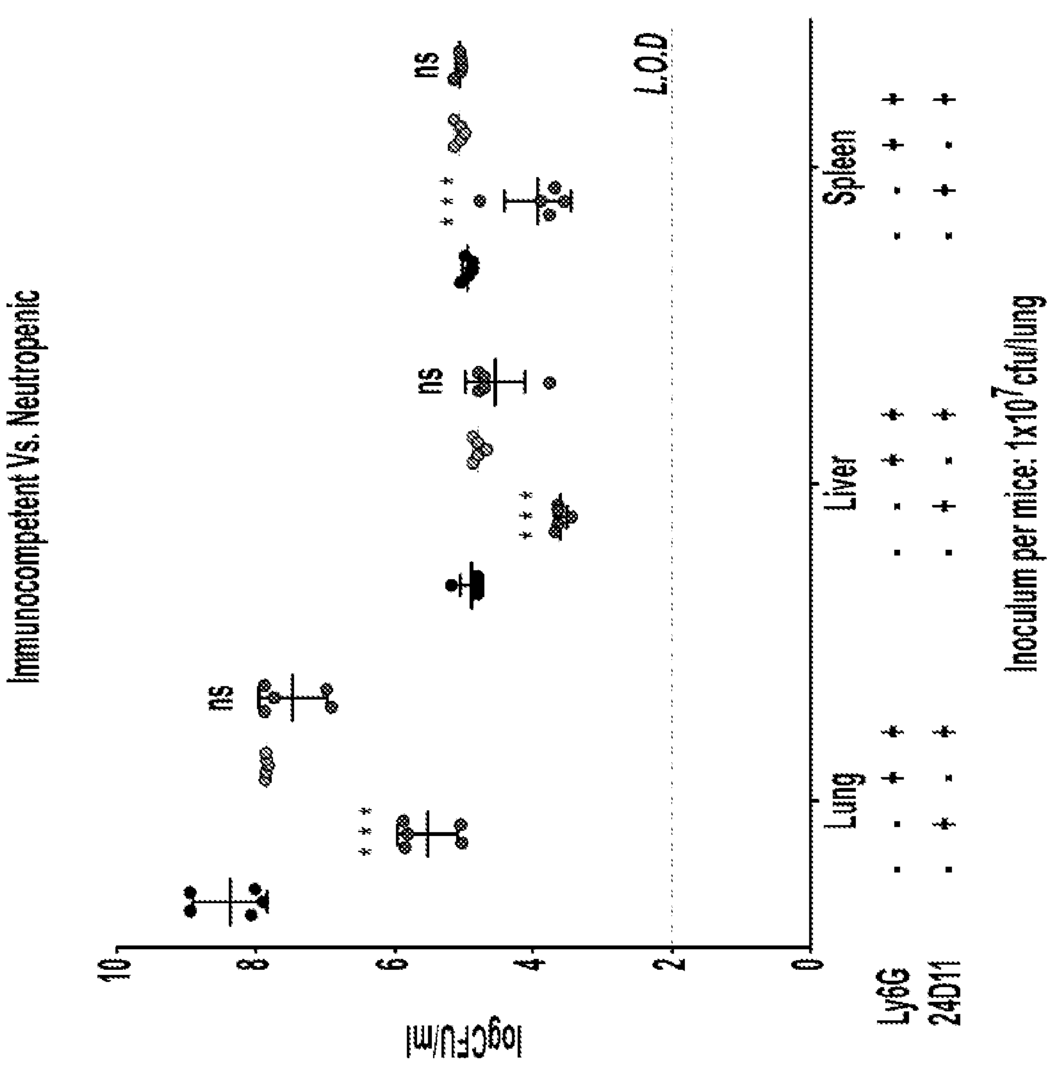
FIG. 10 shows that neutrophil depletion ablates the protective efficacy of mAb 24D11 at high inoculum dose. Bacterial burden in lungs, liver, and spleen of neutropenic and immunocompetent mice infected with a high inoculum of $10^7$ CFU/inoculum of wzi50 strain SBU116. Results depicted a single experiment containing 5 animals in each treatment group. log CFU/ml quantitation in organs was assessed for significance by Two-Way ANOVA and the limit of detection (L.O.D) was set at y=2. Individual comparisons made between treatment groups of mice with same neutrophil status, or between wild type and neutrophil-depleted were tested using Tukey's post-hoc test with p values displayed in-graph. For the in-graph statistics, p-values displayed in blue are comparisons to the wild-type PBS control, and green are for comparisons to the neutrophil-depleted PBS control. Data is shown as Mean±SD and p-values are replaced with ns if ≥0.05, * if <0.05,  if <0.01, * if <0.001, and **** if <0.0001.

CR-Kp lung clearance is improved by mAb 24D11 in neutropenic mice. It was tested whether mAb 24D11 was protective in neutropenic mice when infected with SBU116 CR-Kp strain. Ly6G-mediated neutrophil depletion and generation of neutropenic mice was confirmed by Flow Cytometry (FIG. 9A). The data showed that mice depleted of neutrophils with Ly6G infected with SBU116 ($10^6$ CFU/inoculum) exhibited a higher bacterial lung burden compared to immunocompetent untreated and antibody-treated mice (FIG. 9B). Intraperitoneal treatment with mAb 24D11 decreased the bacterial burden from the lung tissue in both immunocompetent and neutropenic mice by more than 100-fold with respect to untreated controls (FIG. 9B). Monoclonal antibody 24D11 treatment also prevented dissemination in immunocompetent mice but not in neutropenic mice (FIG. 9B). mAb 24D11 had no effect in neutropenic mice when a higher inoculum was used (FIG. 10).

Figure 9C:
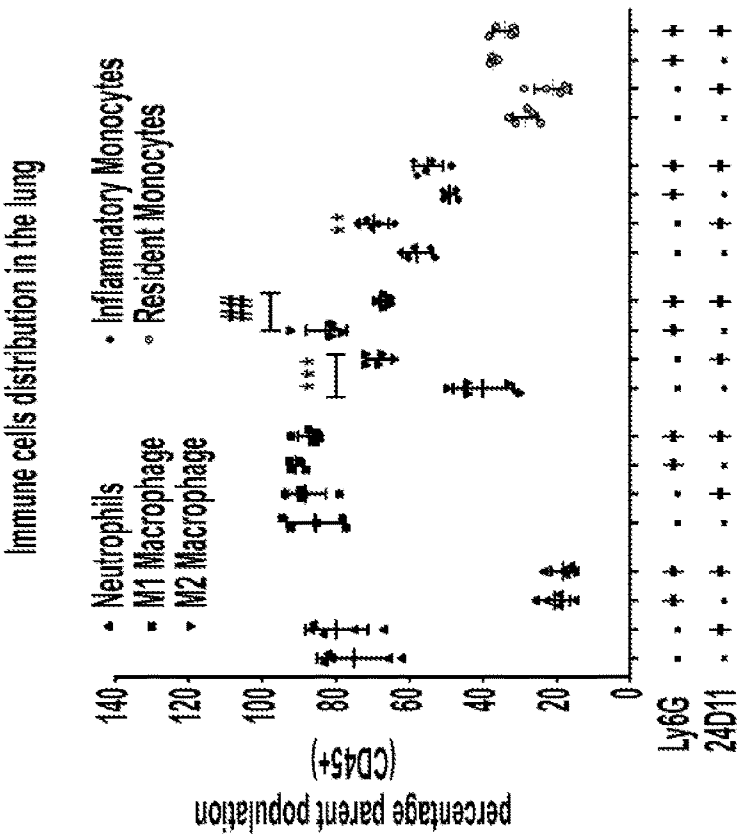
Figure 9D:
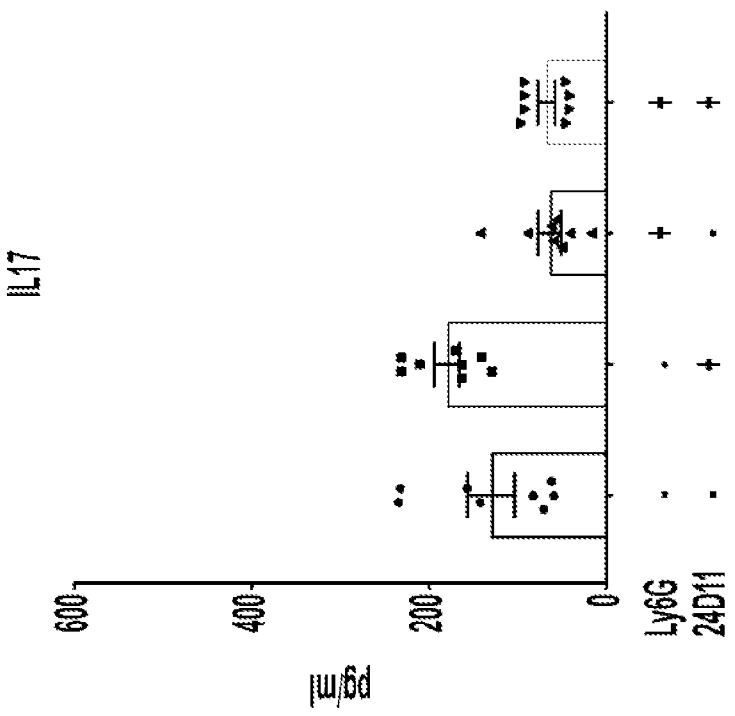
Figure 9E:
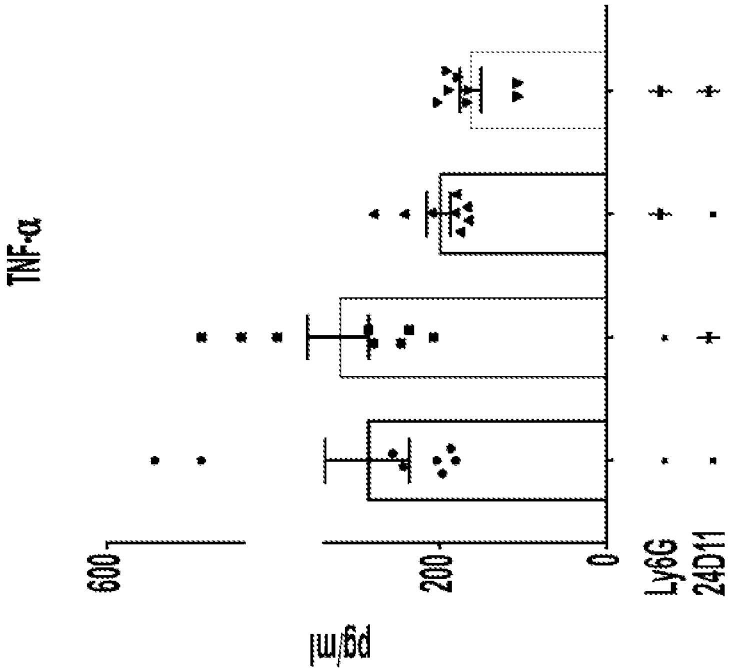

To better understand the immune cells involved in mediating anti-infective efforts of monoclonal antibody 24D11, innate immune cells were studied and compared in both immunocompetent and neutropenic mice (FIG. 9C). First, >80% depletion of neutrophils (black box) in Ly6G treated mice were observed and confirmed (FIG. 9C). CD45+ cells were further subtyped. Immunophenotyping of the innate cells showed no difference in the population of M1 macrophages but a significant change in M2 macrophage population was observed (FIG. 9C). Interestingly, neutropenic mice exhibited higher numbers of M2 macrophages in lung tissue, which was decreased by monoclonal treatment 24D11 treatment of neutropenic mice to similar values observed in the immunocompetent mice. Furthermore, in the lungs of neutropenic and wild type mice, mAb treatment increased the presence of inflammatory monocytes (FIG. 9C). Non-classical resident monocytes were increased by 47% in neutropenic mice with respect to the immunocompetent mice but not affected by mAb treatment (FIG. 9C). No change was observed in $CD45^+CD3^+$ T cells populations across experimental groups. Additionally, the cytokines level of IL-17 and TNF-$\alpha$ were investigated and a decrease between immunocompetent versus neutropenic mice was observed, but no difference was reported within both groups when treated with PBS or with monoclonal antibody 24D11 (FIGS. 9D and 9E). In summary, protective efficacy of mAb 24D11 was still observed in neutropenic mice infected with SBU116 and associated with lower recruitment of M2 macrophages to infected lung tissue.

Figure 11B:
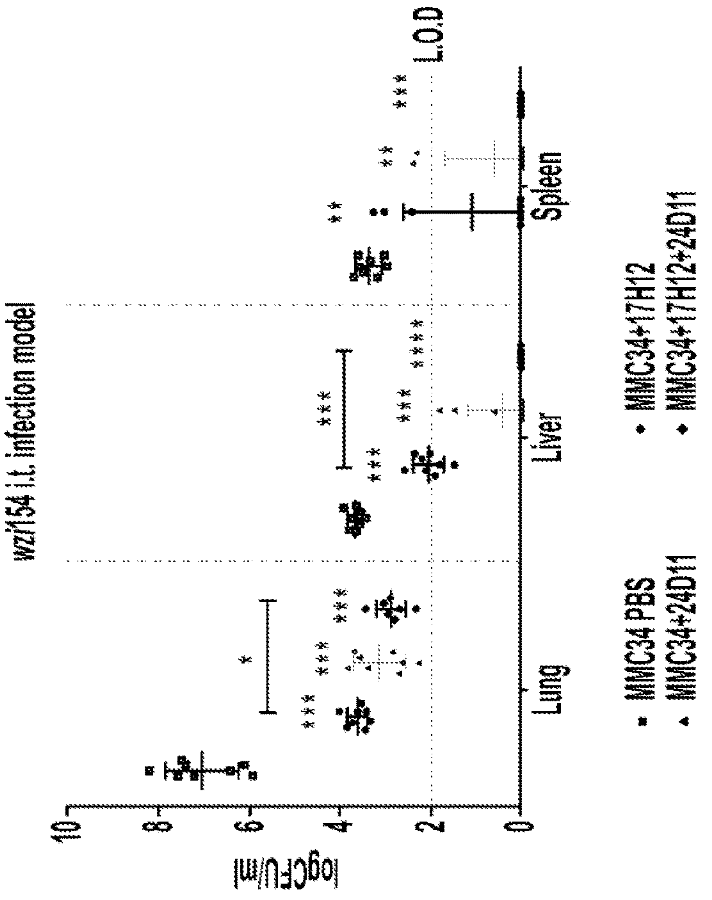
FIGS. 11A-B show that combining monoclonal antibody 24D11 and monoclonal antibody 17H12 does not further enhance protective efficacy against wzi154 CR-Kp.
Figure 11A:
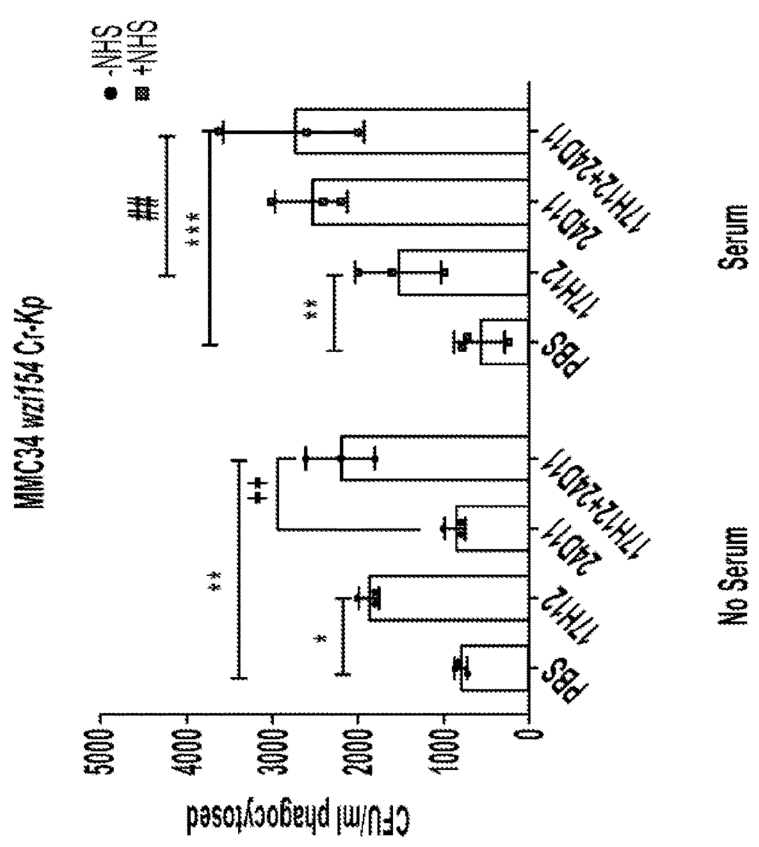

24D11 monotherapy has the same efficacy when compared to 17H12 and 24D11 combination therapy against wzi154 CR-Kp infection. Additionally, as binding competition between monoclonal antibody 24D11 and monoclonal antibody 17H12 was observed above, it was determined whether if combined, how this interaction would affect opsonophagocytosis and in vivo efficacy. It was tested whether the combination of the two monoclonal antibodies promotes effectiveness in clearing wzi54 CR-Kp intratracheal infection. First, it was assessed whether there was enhancement of phagocytic uptake by macrophages when monoclonal antibody 24D11 and monoclonal antibody 17H12 are combined. It was found that the combination therapy in absence of serum increased opsonophagocytis relative to PBS, but not relative to the monoclonal antibody17H12 treatment alone (FIG. 11A, left panel). It was also found that although both monoclonal antibody 17H12 and monoclonal antibody 24D11 promoted opsonophagocytosis in the presence of serum, the combination of the two mAbs did not further enhance phagocytosis (FIG. 11A, right panel).

Figure 12:
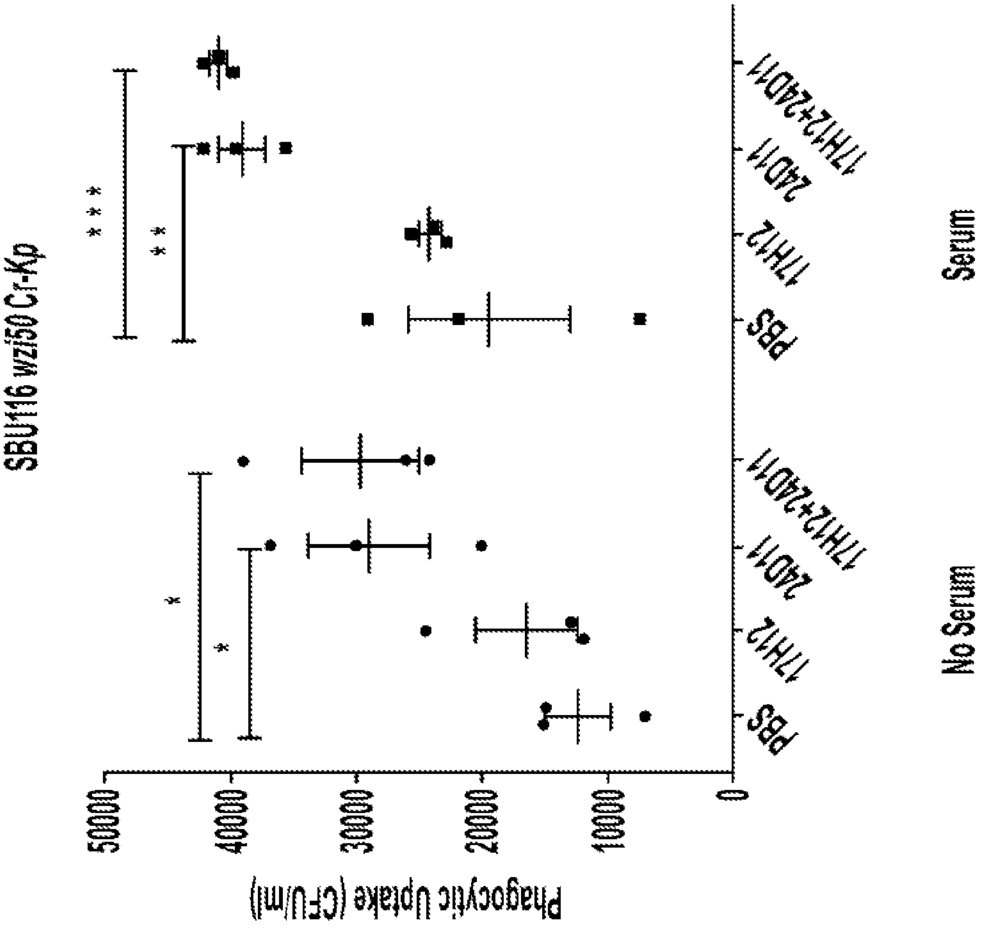
FIG. 12 shows that combining monoclonal antibody 24D11 and monoclonal antibody 17H12 does not further enhance protective efficacy against wzi50 CR-Kp. Phagocytosis of wzi50 SBU116 by J774.A1 murine macrophage-like cells after incubation with 40 μg/ml of either monoclonal antibody 24D11, monoclonal antibody 17H12 or combination of both antibodies with and without normal human serum. Bars depict means and SDs of three independent experiments, with wells performed in triplicate. Differences between PBS and other treatment groups (*) with or without serum, differences between monoclonal antibody 24D11 and combination group with or without serum (+) and differences between monoclonal antibody 17H12 and combination group with or without serum (#) were assessed for significance by repeated-measures two-way ANOVA with results of Tukey's post hoc test for multiple comparisons displayed in the graph. p-values are replaced with ns if ≥0.05, * if <0.05,  if <0.01, and * if <0.001.

In the intratracheal lung infection model, it was observed that MMC34-infected mice when treated intraperitoneally with monoclonal antibody 17H12 and monoclonal antibody 24D11 (10 mg/kg/antibody) combined therapy had a significant drop in the organ burden load and dissemination by >3-$\log_{10}$ fold (FIG. 11B) that was slightly higher than the 2.5-$\log_{10}$ achieved. It was also found that monoclonal antibody 17H12 alone had limited effect on reducing bacterial spread to liver and spleen (FIG. 11B) whereas 24D11 monotherapy prevented dissemination to other organs, which was not further enhanced by combination of monoclonal antibody 24D11 with monoclonal antibody 17H12 (FIG. 11B). The opsonophagocytosis study was repeated with SBU116 CR-Kp strain, and the bacteria preopsonized with monoclonal antibody 24D11 whether alone or in combination was phagocytosed by macrophages under both conditions (FIG. 12). No difference in phagocytosed CFUs was observed between 24D11 monotherapy and combination therapy groups (FIG. 12). These data indicate that the protective efficacy of monotherapy with 24D11 is not further enhanced by combining with 17H12 therapy.

The antigenic variability of capsular polysaccharide of *Klebsiella pneumoniae* remains the primary obstacle in developing immune therapies against it. Based on previous studies, the antigenic diversity of CR-Kp ST258 capsular polysaccharide appears restricted, to a few wzi types (wzi154. wzi29, wzi50, wzil68) which are expressed by the majority of CR-Kp strains. Such restriction is an opportunity to develop immunotherapies useful against these most drug-resistant strains of *Klebsiella pneumoniae*, for which there is little recourse should infection occur. While wzi154 capsular type ST258 strains have been targeted through vaccines and monoclonals, there has been no success in targeting wzi29, which is also expressed by the CR Kp strain that caused the nosocomial outbreak at NIH. This difficulty is possibly a result of destruction of its capsular polysaccharide during the purification process. In addition, protein-conjugation process could disrupt antigenic epitopes. This most likely also explains why high titers were not achieved in mice after vaccinating them with BaPA conjugated wzi50 CPS It has been observed that wzi cross-reactivity by serum antibodies from human patients who convalesced from infection by wzi50 ST258, including reactivity against wzi29. Thus despite differences existing between the sugar composition of wzi29 and wzi50, cross reactive epitopes may exist that could be leveraged to provide broad protection against ST258 strains with wzi types other than wzi154.

The data described herein show that the anti-wzi50 mIgG2b antibody 24D11 had significant in vitro and in vivo activity against both cognate and non-cognate ST258 strains. Bactericidal activity in whole blood was improved by monoclonal antibody 24D11 for wzi50, wzi29, and wzi154 strains, providing evidence of broad cross-coverage activity despite being raised against a single capsular polysaccharide. Similarly, it was observed that monoclonal antibody 24D11 also improved the opsonophagocytosis of several wz150, wzi154, and wzi29 strains. This opsonophagocytosis promotion seemed to be dependent on serum for some strains, while other strains showed activity independent of serum. Strain variability in sensitivity to serum and dependence on complement action has also been observed in CR-Kp strains carrying the same wzi allele. As a result, some strains may be easily opsonized by serum irrespective of antibody (such as MMC38), whereas others may require additional antibody-mediated complement deposition for effective phagocytosis (SBU116). Additionally, serum may exhibit bactericidal activity prior to opsonophagocytosis, affecting final phagocytosis counts. Nevertheless, monoclonal antibody 24D11 was shown to promote opsonophagocytosis in a CPS-dependent matter and appears specific to ST258 wzi-types.

The results described herein also demonstrated that the activity of monoclonal antibody 24D11 against wzi50, wzi154, and wzi29 in vivo, with reductions in lung bacterial burden of certain CR-Kp strains when monoclonal antibody 24D11 was used to pre-opsonize bacteria. Systemically administration of monoclonal antibody 24D11 was further efficacious, reducing bacterial burden in the organs evaluated for the tested strains when given prophylactically, and even reducing lung burden against the tested strains when given therapeutically after infection. The data demonstrates that the cross-CPS protection conveyed by monoclonal antibody 24D11 can function systemically to help clear CR-Kp after infection establishment. To date, few studies examining antibody activity against multi-drug resistant Kp in vivo have examined activity of a post-infection therapeutic antibody dose. Additionally, this data demonstrates that monoclonal antibody 24D11 does not solely act through simple steric inhibition or inactivation.

The finding that monoclonal antibody 24D11 also exhibits protection in neutropenic mice can be advantageous, since patients with hematologic malignancies requiring transplants and neutrophil ablation can quickly succumb to CR-Kp infection. The cytology data demonstrate monoclonal antibody 24D1 1's ability to promote inflammatory monocyte recruitment in both undepleted and neutropenic mice, which contribute to CR-Kp clearance.

This recruitment combined with successful reduction of bacterial burden in the lungs of neutropenic mice treated with monoclonal antibody 24D11 further emphasize a role for these cells. Additionally, the effect of monoclonal antibody 24D11 on the population on anti-inflammatory M2 macrophages appear to change based on the presence of absence of neutrophils, with monoclonal antibody 24D11 promoting M2 recruitment in the presence of neutrophils but reducing them in the neutropenic state. Certain CR-Kp stains have been shown to influence NF-κβ and STAT-6 signaling to promote anti-inflammatory M2 polarization to promote colorectal tumorigenesis, and recruit monocytic myeloid-derived suppressor cells that allow prolonged survival within the infected lung, demonstrating an anti-inflammatory role of CR-Kp in promoting its survival. However anti-inflammatory cytokines such as IL-10, produced by these same myeloid-derived suppressor cells, may also be important for host survival against CR-Kp. Prior to the discovery of monoclonal antibody 24D11, it was thought that any anti-capsular monoclonal antibody therapy strategy against CG258 CR-Kp would have required a cocktail of two or more, since data on monoclonal antibody 17H12 demonstrated a divide between immune recognition of wzi154 CPS epitopes and wzi29 CPS epitopes. Therefore, it was surprising to observe monoclonal antibody 24D11 s strong activity against wzi29-, and wzi50-carrying CRKP strains, as well wzi154-carrying strains. Furthermore, the in vitro and in vivo data demonstrated that in most cases treatment with monoclonal antibody 24D11 was non-inferior to combination treatment with the wzi154-CPS-specific antibody 17H12. This may be due to the shared epitope of monoclonal antibody 24D11 and monoclonal antibody 24D11, as demonstrated by the competition assays. Nevertheless, monoclonal antibody 24D11 must bind at a slightly different, perhaps more conserved site on CPS than monoclonal antibody 17H12, allowing it to provide large cross-protection, and even possibly obviating need for a monoclonal cocktail.

Passive immunotherapy can be a useful tool against multi-drug resistant organisms, especially in individuals who lack a strong immune response. The difficulty of these therapies involves ensuring the antibody is useful against the target, as organisms such as *Klebsiella* have extensive capsular variability, and empiric therapy with monoclonal antibodies is not cost-conducive. Additionally, recent evidence with SARS-CoV-2 show that monoclonal treatments work best in the pre-symptomatic period of an overwhelming infection. Studies have also shown that many infections caused by CR-Kp and other multidrug resistant organisms appear to occur most frequently in pre-colonized individuals, and usually with strains congruent with their colonizing flora. An anti-CG258 antibody could thus possibly be used in patients who are identified carriers of the infection through perianal, fecal, and nasal screening and molecular testing for MLST and wzi allele carriage, though continued development of more rapid diagnosing tools would be beneficial. Additionally based on the efficacy of monoclonal antibody 24D11, and the predominance of wzi154, wzi29, and wzi50 strains within CG258 in the United States, this monoclonal antibody 24D11 would theoretically be active against 70-100% of ST258 strains, roughly half of the CR-Kp isolates in the United States by recent reports.

More importantly, the identification of a capsular type that triggers cross-reactivity against wzi29 and wzi154 indicates presence of possible conserved epitopes between various wzi-types and presents the opportunity to establish a vaccination strategy against the broader ST258. Bioconjugate strategies against Kl *Klebsiella* capsule suggest the possibility of generating immunogenic capsular polysaccharide without labor-intensive purification that may also damage the native sugar architecture. That being said, vaccine strategies against *Klebsiella* should be pursued with caution as use may introduce selective pressure on the ST258 capsule. The evolution of the 258 clonal group is marked with numerous recombination of the CPS region, and multiple IS elements within the loci. Such elements could facilitate recombination lead to diversification of the capsule away from these capsular types, which occurred after the initial success by pneumococcal vaccines. Immunotherapies with CPS specific mAbs would not have that effect and given that many patients with CR-Kp infections also have many comorbidities such as cancer mAb therapy of selected patients may be more successful than a vaccination-based approach.

In summary, the data described herein shows that anti-wzi50 mAb 24D11 provides broad protection against three prevalent wzi types of carbapenem-resistant *Klebsiella pneumoniae* with preserved efficacy in neutropenic mice, and may be useful as a CPS-based vaccine.

Materials and methods. Surgeries was performed under ketamine-and-xylazine anesthesia.

Capsular polysaccharide (CPS) purification and conjugation. Capsular polysaccharide from carbapenem-resistant *K. pneumoniae* strain MMC38 (wzi50) was purified. Briefly MMC38 strain was cultured overnight at 37° C. in LB, pelleted, washed, and resuspended in distilled water. CPS was extracted in the aqueous phase of phenol-water extraction and precipitated using 5 volumes of methanol plus 1% (v/v) of a saturated solution of sodium acetate in methanol and incubated for 2 hours at −20° C. The pellet was dissolved in distilled water and dialyzed against water in 10K MWCO SnakeSkin Dialysis Tubing (Thermofisher) prior to lyophilization. The lyophilized polysaccharide was dissolved digested with nucleases (50 mg/ml of DNase I and RNase A) and proteinase K was added (50 mg/ml). Polysaccharides were precipitated as stated herein and dissolved in water. LPS was removed by ultracentrifugation (105000× g, 16 h, 4° C.) and samples were freeze-dried and dissolved in endotoxin-free water. Final CPS purification was performed using high-pressure liquid chromatography (AKTA) with a GE Healthcare HiPrep™ 16/60 Sephacryl S200HR size exclusion column. Fractions positive for CPS were determined by sulfuric acid/phenol detection, and then pooled, lyophilized, and resuspended in endotoxin-free water. Final concentration was determined by sulfuric acid/phenol detection using glucose as a standard. Absence of LPS (<20 EU/ml endotoxin limit for polysaccharide vaccines) in purified CPS was confirmed by Pierce™ LAL Chromogenic Endotoxin Quantitation Kit (Thermo Scientific) with a lower detection limit of 0.01 EU/ml [0.01 ng endotoxin per mL]. Conjugation to the Protective Antigen of *Bacillus anthracis* (wzi50-BaPA) using the CDAP method was performed as previously described.

Vaccinations and Titer Calculations. BALB/c mice (Taconic) were administered either 10 μg of BaPA-conjugated wzi50 CPS, unconjugated wzi50 CPS or no polysaccharide in 100 μL of a 1:1 mixture of PBS with Complete Freund's adjuvant by intraperitoneal injection. Booster injections were given by intraperitoneal injection every 2 weeks using a 1:1 mixture of Incomplete Freund's adjuvant until sufficient titers (1:10,000) or the necessary time point was reached. Serum titers of mice were measured from clotted serum extracted by facial bleed using ELISA with plates coated with unconjugated wzi50 CPS, conjugated wzi50 CPS, and also against methanol-fixed whole CR-Kp bacteria as per the protocol. Serum titer was defined as the lowest serum dilution at O.D. of vaccinated mice serum 2.5 times the O.D. of naïve mouse serum.

Monoclonal Antibody generation. Fusion and cloning were performed using PEG-mediated fusion of splenocytes to myeloma lines Ag.8 or NSO$^{bcl2}$, followed by selection in hypoxanthine-aminopterin-thymidine (HAT) medium. Two weeks after a final booster with unconjugated wzi50 CPS, the mice from the unconjugated vaccine group were euthanized and splenocytes were immediately isolated and fused. Fused splenocytes-myeloma cells were diluted over 36 plates, and after 1-week supernatants of each well were screened by ELISA for wzi50 CPS-binding antibodies. Positive wells (O.D≥2.5× background) were confirmed, then expanded, split, and tested again. Fused cells from positive wells were then cloned in soft agar (SeaPlaque). Individual clones underwent final confirmatory testing and isotyping by ELISA.

Monoclonal Antibody Purification. Antibodies were produced weekly over six months from respective hybridoma grown in CELLine (Wheaton) flasks fed with High-Glucose DMEM+10% NCTC media and 1× Penicillin-Streptomycin and 1× Non-Essential Amino Acids, supplemented with either 10% or 5% FBS in the inner and outer chambers, respectively. These antibodies were purified using Pierce Protein G Affinity Chromatography as per manufacturer's protocol. Eluted antibody was neutralized in Tris-HCl, pH 8.0, and NaCl to final concentrations of 100 mM and 300 mM, respectively, then concentrated by centrifugal filtration (AMICON 30K), filter-sterilized, snap frozen in liquid nitrogen, and stored at −80° C. until use. Concentration was determined by Bradford assay and absorbance at 280 nM (Extinction coefficient=1.4).

Binding Affinity Analysis. The $EC_{50}$ of the mAbs was calculated using ELISA as. Briefly, polystyrene plates (Corning 3690) were coated overnight with 0.5 mg/mL of wzi50 CPS in PBS, then blocked with 1% PBS-BSA. Antibody was detected using an AP-conjugated Goat anti-Mouse IgG2b secondary antibody (Southern Biotech, 1091-04, 1:1000). Control antibodies were run in parallel as negative controls. Binding curves were calculated in GraphPad Prism 6 using a four-parameter variable slope log agonist response curve.

Competitive ELISA. A competitive ELISA assay was modified. Briefly, 96-well plates were coated overnight at 4° C. with 0.5 μg/well of detergent-free purified CPS34 and CPS38. Next day, plates were blocked with 2% PBS-BSA for one-hour. After blocking, an antibody cocktail was added to the coated wells where the primary anti-capsular monoclonal antibodies were at a constant concentration of 40 μg/ml and the competing anti-capsular monoclonal antibody was added at an increasing concentration of 0 μg/ml-80 μg/ml. The decrease of binding to the CPS of the first antibody at constant concentration was detected by AP-labeled secondary antibodies (1:1000) against the first antibody. The competitive binding curve was plotted using GraphPad Prism 6.

In vitro Whole Blood Resistance Assay. In vitro whole blood resistance assay was modified. Blood samples collected from healthy donors were kept at room temperature and processed within 4 h of collection. Blood was diluted 1:1 with sterile prewarmed (37° C.) RPMI 1640 (Life Technologies, Grand Island, NY), and a final volume of 200 μl was added to each well of 96-well tissue culture-treated round-bottom plates (Becton Dickinson). Bacterial suspensions of MMC34, MMC36 & SBU116 was prepared from the log-growth phase ($O.D._{600nm}$ 0.3-0.5) at a concentration of $1\times10^6$ CFU per ml and back plated at 0 min to confirm the concentration. Bacterial suspensions were added to blood samples at 10 μl per well to yield the desired inoculum concentrations of $1\times10^8$ CFU per ml. Blood samples were simultaneously treated with either 200 μg of anti-capsular monoclonal antibodies, or isotype controls, and cultured at 37° C. standing in a humidified incubator at 5% $CO_2$ for the respective duration of the experiment. At 1 h, and 2 h in culture, 100 μL was sampled from each tube, 1:10 diluted, and plated onto LB agar for CFU/ml quantitation. For the experiments, conditions were performed in triplicate wells, and experiments were repeated three times.

Macrophage phagocytosis. Macrophage cell line J774A.1 (ATCC) was used for macrophage phagocytosis assays with anti-capsular antibodies. Briefly, $1\times10^5$/ml J774A.1 cells were incubated overnight in wells of cell culture-treated 96-well plates. The following day, $1\times10^6$/ml bacteria (MMC34, MMC36, MMC38, SBU219, SBU207, SBU116, wzi154 CPS-expressing 33576 and a capsular 33576 Δwzy mutant, and ST307 strain) were opsonized for 60 min in DMEM containing 40 μg/ml of anti-$wzi_{50}$ capsular monoclonal antibodies. Opsonized bacteria at the multiplicity of infection [MOI]=1 was added to each well of the washed macrophage plates. For complement dependent phagocytosis assay, macrophages were treated with 10% normal human serum (NHS) in DMEM, 1 h prior to the addition of the opsonized bacteria. After 30 min of incubation at 37° C. in 5% $CO_2$, cells were washed thrice with serum-free DMEM alone and then exposed to 100 μg/ml of polymyxin B in serum-free DMEM for 30 min to kill off bacteria that were not phagocytosed and were present outside the cells. Cells were washed again for five times, and wells were immediately lysed twice with water and dilution plated on LB plates. The number of CFUs were calculated from LB plates was divided by the number of estimated cells plated to give the CFUs phagocytosed. For the experiments, conditions were performed in triplicate wells, and experiments were repeated three times.

Intratracheal Infection of Mice. C57BL/6 mice (Taconic), aged 6-14 weeks were used, and pulmonary infection was performed. Mice were anesthetized with 90-100 mg/kg of ketamine and 5-10 mg/kg of xylazine. Tracheas of the mice were surgically exposed, and 50 μl of PBS containing $6\times10^8$ CFU of MMC34, MMC36, and SBU 116 was instilled into trachea using a bent 27G needle. Mice were administered 0.1 mg/kg buprenorphine for analgesia immediately post-surgery and monitored for recovery.

For pre-opsonized mice, bacterial strains were opsonized with 5 mg/ml of anti-wzi50 capsular mAbs. After 1-hour opsonization, 50 μL of the inoculum was instilled into the surgically exposed trachea of a mouse under ketamine/xylazine using a bent 27G needle (Inocula were backplated at the conclusion of the surgeries to test for bacterial viability). For prophylactically treated group, mice were pretreated intraperitoneally with either 100 μl of PBS or 10 mg/kg of mAb 24D11 4 hours prior to infecting mice intratracheally with 50 μl of PBS containing $6\times10^8$ CFU of bacterial inoculum. For therapeutic group, mice were infected 50 μl of PBS containing $6\times10^8$ CFU of bacterial inoculum and 4 hours post-surgery they received 10 mg/kg of mAb 24D11 or mAb 17H12 through intraperitoneal injection. For both experimental groups after 24 hours post-surgery, mice were euthanized, and organs (lungs, liver, spleen) were collected through necropsy. Organs were processed and serially diluted in 10-fold dilutions in ice-cold PBS and were plated on LB-Agar to enumerate bacteria (CFU/ml/organ) in homogenized tissue and bacterial dissemination analysis.

Intratracheal Infection of Neutropenic Mice. To elucidate the efficacy of mAb 24D11 in neutropenic mice, mice were pretreated with 225 μg of Rat anti-mouse Ly6G (1A8) or a control Rat anti-mouse IgG2a (2A3) (BioXcell) by intraperitoneal injection 48 hours and 4 hours prior to the intratracheal surgery. After 4 hours, neutropenic mice received anti-wzi50 capsular mAbs intra-peritoneally and was observed for 24 hours. After 24 hours mice were euthanized, and lung tissues were dissected into two portions. The first half of the lungs were processed similar to the aforementioned methods and collected in PBS containing 1× Pierce Proteinase Inhibitor. To count CFUs, lung homogenates were serially diluted 10-fold and plated on LB-Agar plates to enumerate the CFUs. Supernatants of lung homogenates used for IL-17 and TNF-α, cytokine analysis were stored at −80° C. were tested using BioLegend® ELISA Max™ Deluxe set (Cat #436204 & 430904) according to manufacturer's protocol. Liver and spleens were collected and processed in ice-cold PBS and serially diluted to analyze CFUs on LB agar plates.

The remaining portion of lung tissues were processed in 1.25 ml of 1×FACS buffer (1×PBS+2% Fetal Bovine Serum) containing Collagenase IV (Final Concentration 150 U/ml) and DNAse 1(10 U/ml) for flow cytometry analysis to confirm neutrophil depletion. Lung tissues were digested for 1.5 hours and then homogenized lungs were passed through a 70 μm cell strainer. Cell suspensions were centrifuged for 5 min at 300×g at 4° C. and cell pellets were resuspended in 5 ml of Red Blood Cells Lysing Buffer (Cat #R7757, Sigma) on ice for 30 seconds. After RBC-lysis, cell suspensions were washed twice in 5 ml of 1×FACS buffer for 5 min at 300×g at 4° C. and cell pellets were finally resuspended in 3 ml of FACS buffer, filter passed in flow cytometry tubes (BD Cat #352008) and counted. $1\times10^6$ cells were stained with 1:200 dilution of fluorophore-labelled antibodies (50 μl antibody added to 50 μl of unlabeled cells). Cells were gated as Live/Dead cells first followed by $CD45^+$ gating, then immune cells were gated as follows: Neutrophils ($CD45^+CD11b^+Lv6G^+$), M1 macrophages ($CD45^+CD11b^+CD11c^+F4/80^+$), M2 macrophage ($CD45^+CD11b^+F4/80^+$), inflammatory monocytes ($CD45^+CD11b^+Ly6C^+Ly6G^+$), resident monocytes ($CD45^+CD11b^+Ly6C^-Ly6G^-$) and T cells ($CD45^+CD3^+$). The flow cytometry data were processed in BD FACSDiva™ and Flowing Software (Turku Bioscience, Finland). Briefly, the flow cytometry gating strategy to phenotype immune cells present in the lungs is as follows. Immune cells isolated from the lungs of wildtype and neutropenic mice treated with or without monoclonal antibody 24D11 were gated in an SSC-A and FSC-A dot plot to eliminate dead cells and aggregated cells. Single cells were gated in an FSC-H vs. FSC-A dot plot to eliminate doublets. Single cells were then gated on the Live/Dead Alexa 700 axis to eliminate dead cells: CD45+ live leukocytes were gated. CD45+CD11b+ and CD45+CD11c+ leukocytes were gated. CD45+CD3+ gating was chosen to analyze total T cells. CD11b+F4/80+ gate was chosen for M2 Macrophages and $CD11b^+CD11c^+F4/80^+$ for M1 macrophages, inflammatory monocytes were gated on $Ly6C^{hi}$CD11b+ gate and resident monocytes were chosen on $Ly6C^{low}$ $CD11b^{low/intermediate}$ gating. Ly6G+ gating on CD11b+ leukocytes were chosen to analyze neutrophils. FSC-A: Forward scatter area. FSC-H: Forward scatter height. SSC-A: Side scatter area.

Statistical analysis. Statistical tests were performed with GraphPad Prism 6 for Windows. For multigroup comparisons of parametric data (e.g., phagocytosis, serum-resistance assay, and animal experiments), ANOVA with post-hoc analysis using Tukey's, Sidak's, or Dunnett's comparison test was used. For two-group comparisons of parametric data, paired t-tests corrected for multiple comparisons using the Holm-Sidak method were performed.

Example 2: Glycosyl Linkage Analysis of Isolated CPS from *K. pneumoniae* Patient Strain MMC38

Described herein are the linkages detected in three aliquots of the CPS38 (5 mg, 15 mg/mL, 0.5 mg/mL).

Linkage Analysis. Permethylation was performed according to the following protocol. Two hundred mg of the sample was freeze dried and then dissolved in 400 mL of dimethyl sulfoxide (DMSO) overnight. Sodium hydroxide (NaOH) base was prepared in a glass screw-cap tube with 100 mL of 50% NaOH and 200 mL of dry methanol. Two mL of DMSO was added, and the mixture was vortexed and centrifuged briefly. The DMSO was removed and discarded. This was repeated four times. Finally, 2 mL of DMSO was added again and the solution vortexed. Three hundred mL of the NaOH base was added. The sample containing base was stirred for 15 min. One hundred and fifty mL of iodomethane was added and stirred for 25 minutes. These two steps were repeated one more time to ensure adequate mixing. Once mixing was completed, 2 mL of dichloromethane (DCM) and 2 mL $H_2O$ were added.

The tube was vortexed and centrifuged briefly, then the upper (aqueous) layer was removed.

This step was repeated four more times. After the final wash, the DCM layer was removed into a separate tube and dried with $N_2$ gas.

The permethylated samples were hydrolyzed in 2 M TFA for 2 h at 121° C., and then dried down with isopropanol under a stream of nitrogen. The samples were reduced with NaBD4 in 100 mM $NH_4OH$ (10 mg/mL) overnight. The following day, the reaction was neutralized using glacial acetic acid, and then dried with methanol. The samples were 0-acetylated using 250 mL of acetic anhydride and 230 mL of TFA at 50° C. for 10 min., then dried under a stream of nitrogen. Finally, the samples were reconstituted in DCM and washed with water before injection.

The resulting partially methylated alditol acetates (PMAAs) were analyzed on an Agilent 7890A GC interfaced to a 5975C MSD; separation was performed on a Supelco 2331 fused silica capillary column (30 m×0.25 mm ID) with a temperature gradient detailed in Table 4. The method is a derivation of the linkage method detailed by Heiss et al (Heiss. C., et al. The Structure of Cryptococcus Neoformans Galactoxylomannan contains beta-D-glucuronic acid. (2009) Carbohydr. Res. 344: 915-920).

TABLE 4

Temperature program for the GC/MS used for linkage analysis

| | Rate (° C./min) | Value (° C.) | Hold Time (min) | Run Time (min) |
|---|---|---|---|---|
| Initial | | 60 | 1 | 1 Time (min |
| Ramp 1 | 27.5 | 170 | 0 | 5 |
| Ramp 2 | 4 | 235 | 2 | 23.5 |
| Ramp 3 | 3 | 240 | 12 | 36.9 |

Figure 13:
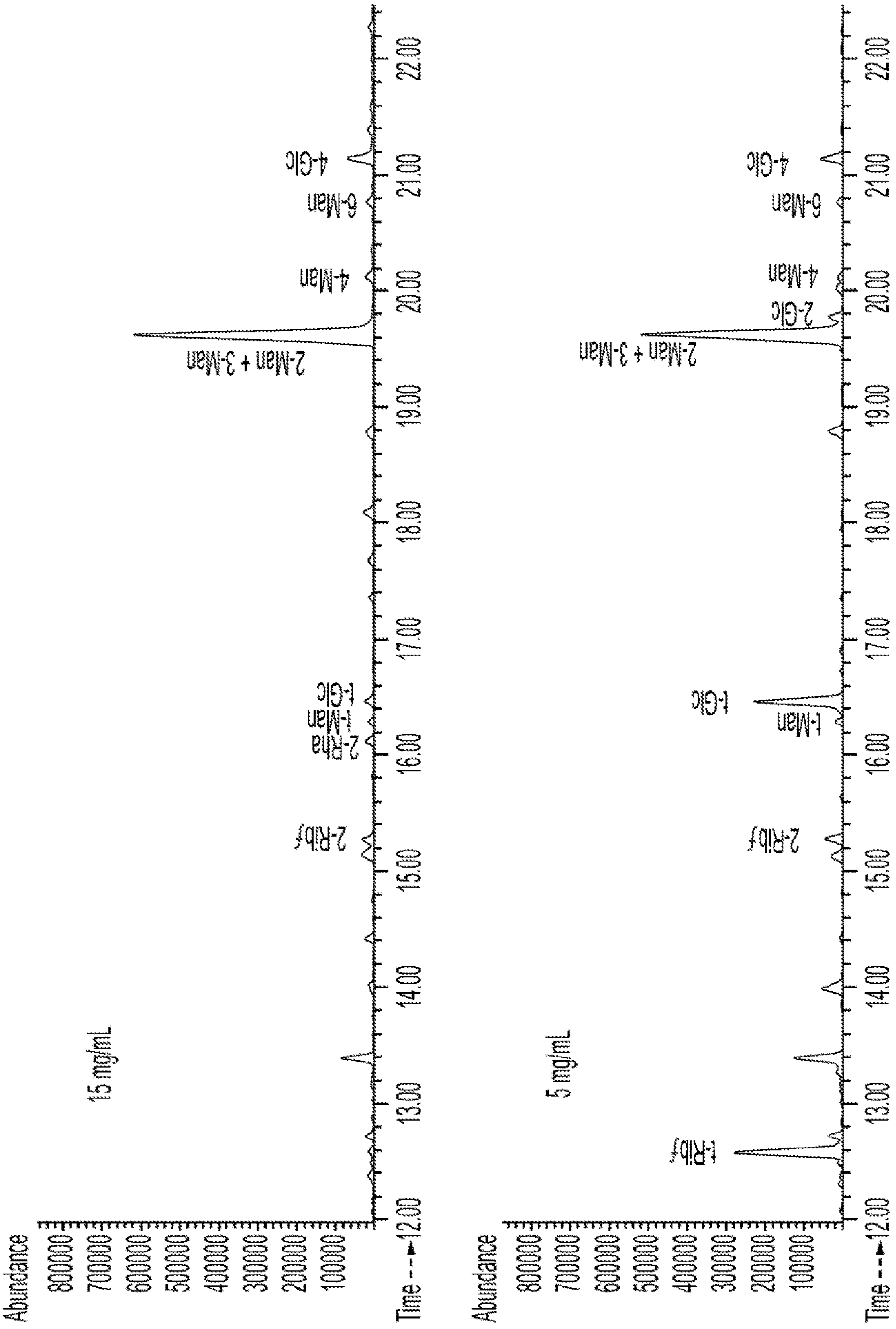
FIG. 13 shows GC chromatogram for the glycosyl linkages of the PMAAs detected in CPS38 aliquots 15 mg/mL, 5 mg, and 0.5 mg/mL.
Figure 13:
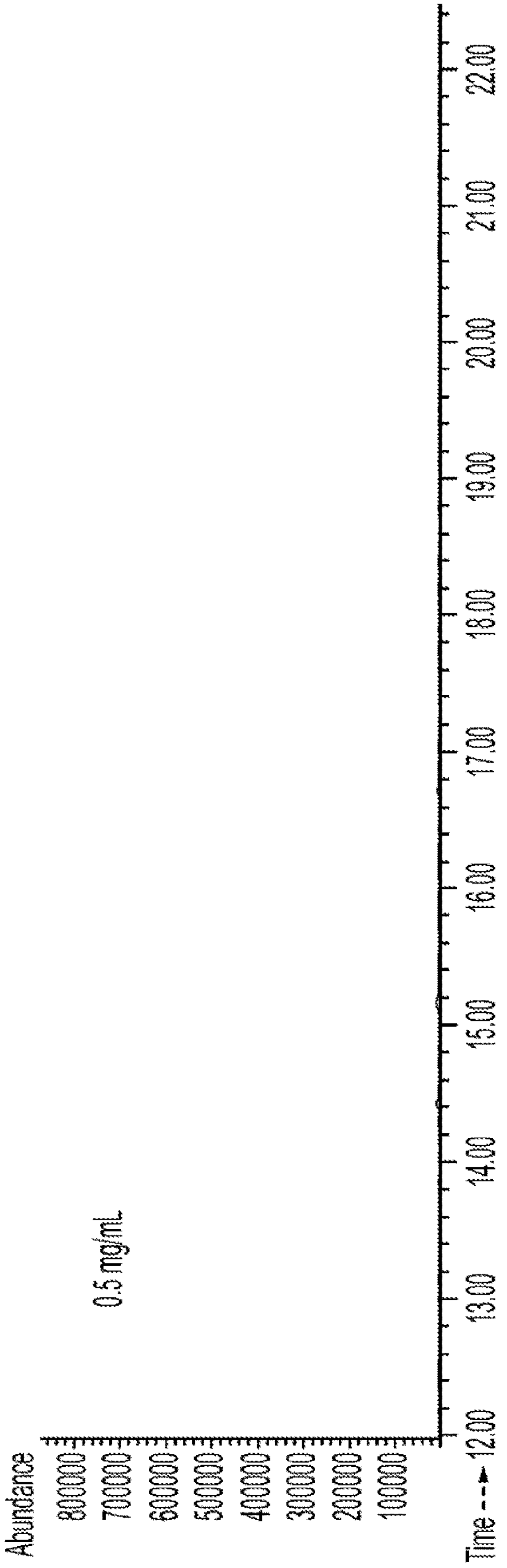

Results. The chromatograms for linkage analysis are shown in FIG. 13, and the relative percentages of linkages are listed in Table 5. Sugar linkages were detected in the pyranose conformation, except those from ribose, which are present in the furanose form.

The predominant linkages of the 15 mg/mL CPS-38 aliquot were 2-linked Manp (57.7%) and 3-linked Manp (34.7%). Low quantities of 2-linked Ribf, 2-linked Rhap, t-Glcp, 4-linked Manp, and 6-linked Manp. In addition, t-Manp was also detected.

Similarly, the most abundant linkage residues detected in the 5 mg aliquot were 2-linked Manp (30.7%) and 3-linked Manp (19.4%). However, high quantities of t-Ribf (23.2%), and t-Glcp (17.9%) were also detected. In addition, the 5 mg aliquot contains moderate amounts of 2-linked Ribf, 2-linked Glcp, and 4-linked Glcp. Less than 1% of each of the other linkages were detected.

No linkages were detected in the 0.5 mg/mL aliquot. This finding could indicate low carbohydrate content for this aliquot.

TABLE 5

Relative percentages of linkages detected in CPS38 sample aliquots

| Residue | 15 mg/mL | 5 mg | 0.5 mg/mL |
|---|---|---|---|
| Terminal Ribofuranosyl (t-Ribf) | n.d. | 23.2 | n.d. |
| 2-linked Ribofuranosyl (2-Ribf) | 1.3 | 2.9 | n.d. |
| 2-linked Rhamnopyranosyl (2-Rhap) | 1.0 | n.d. | n.d. |
| Terminal Mannopyranosyl (t-Manp) | 0.4 | 0.6 | n.d. |
| Terminal Glucopyranosyl (t-Glcp) | 0.6 | 17.9 | n.d. |
| 2-linked Mannopyranosyl (2-Manp) | 57.7 | 30.7 | n.d. |
| 3-linked Mannopyranosyl (3-Manp) | 34.7 | 19.4 | n.d. |
| 2-linked Glucopyranosyl (2-Glcp) | n.d. | 1.9 | n.d. |
| 4-linked Mannopyranosyl (4-Manp) | 0.8 | 0.2 | n.d. |
| 6-linked Mannopyranosyl (6-Manp) | 0.5 | 0.5 | n.d. |
| 4-linked Glucopyranosyl (4-Glcp) | 3.0 | 2.7 | n.d. |

Legend: n.d.—not detected

Eample 3: CR-Kp Strains

Figure 14A:
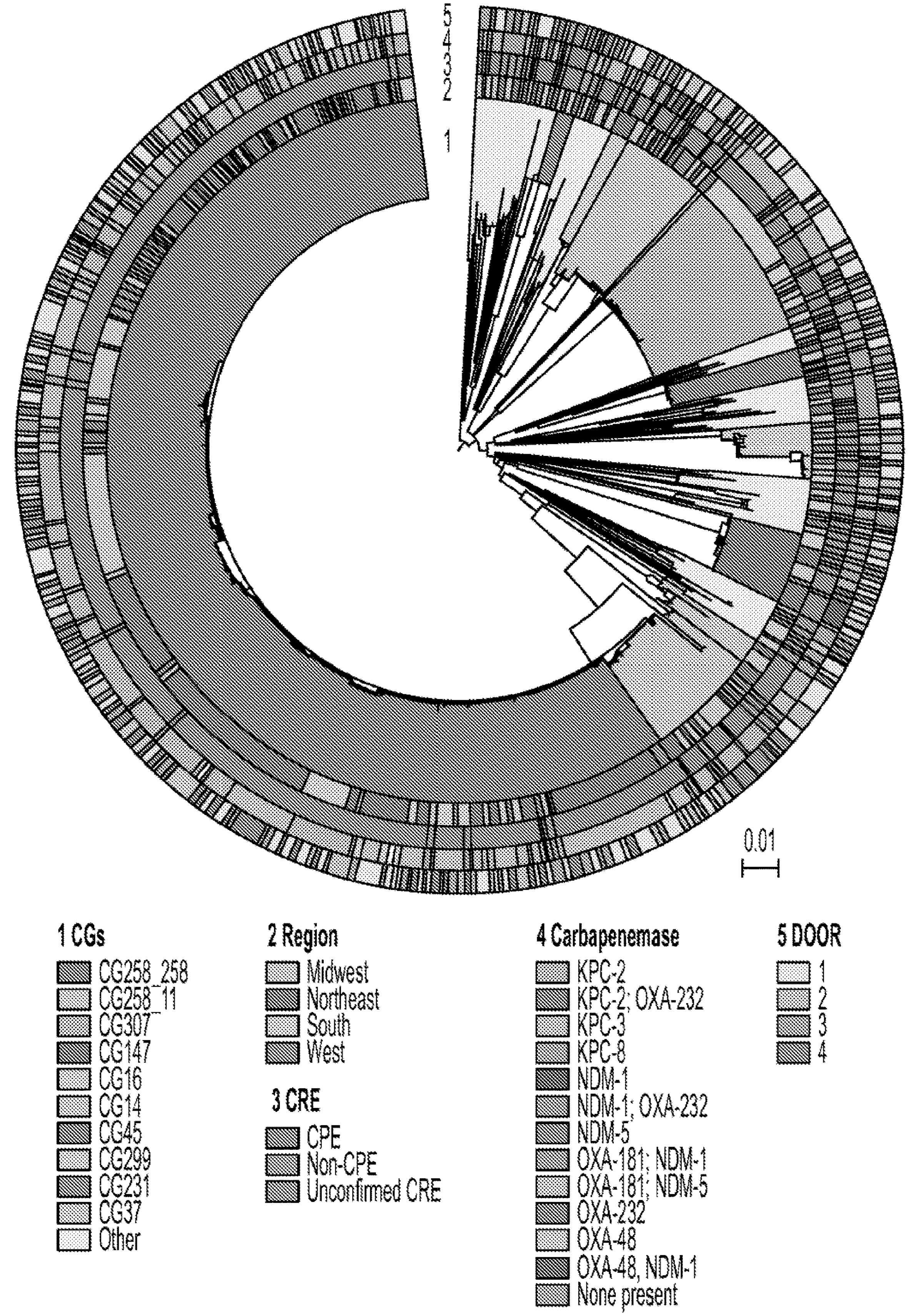
FIGS. 14A-B show the genetic and phenotypic characterization of CR-Kp strains infecting patients.
Figure 14B:
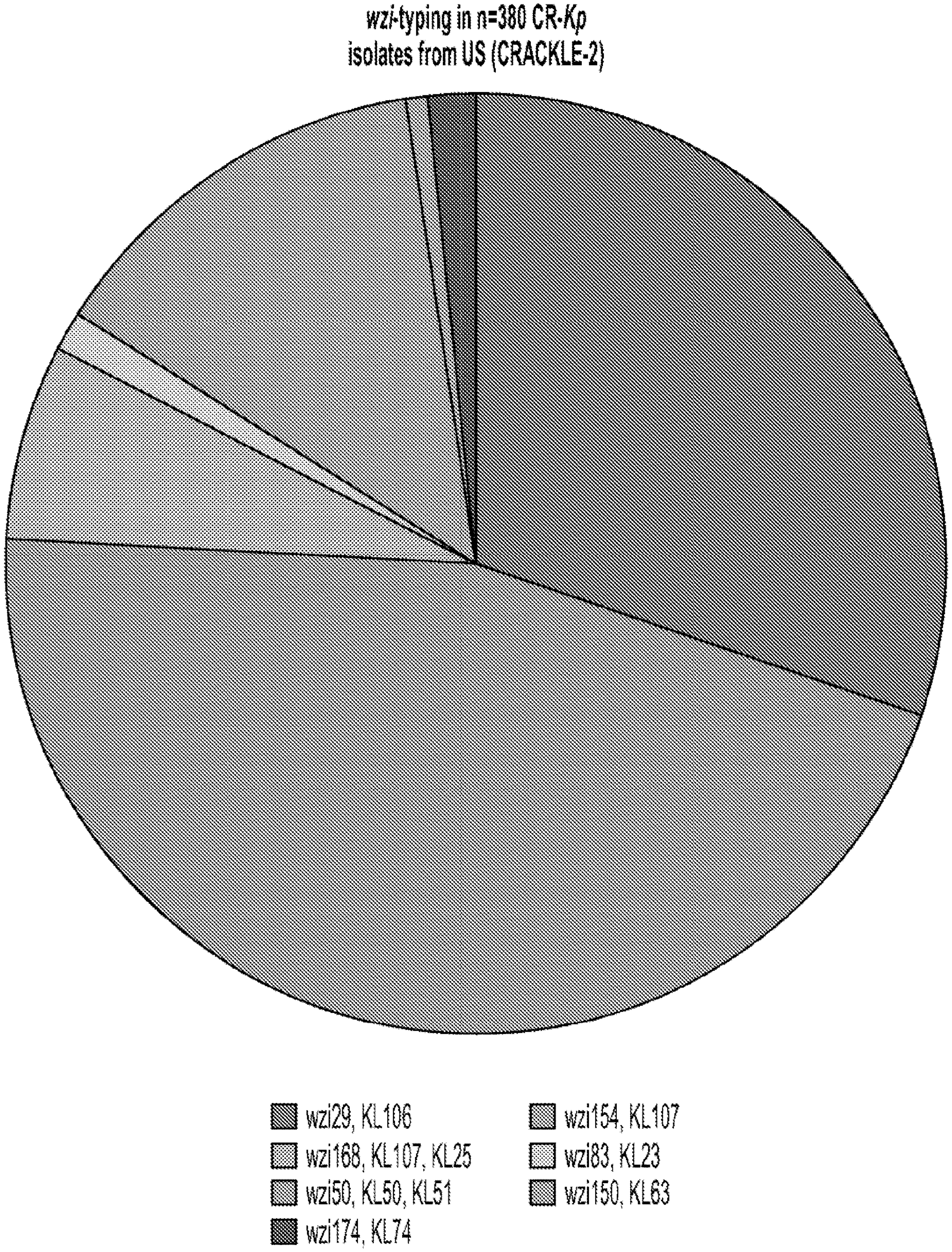

CR-Kp strains in the U.S. are predominantly ST258 strains, but ST307 strains are also emerging. In a CRACKLE-2 study performed by D. van Duin et al. (Molecular and clinical epidemiology of carbapenem-resistant Enterobacterales in the USA (CRACKLE-2): a prospective cohort study. The Lancet infectious diseases 20, 731-741 (2020)). CR-Kp strains were collected with patient data over several years. In this study, the most common clonal group (CG) of CR-Kp was CG258 (>75-80%). Of the 382 CG258 CR-Kp strains 364 (95%) were carbapenemase-producing, harboring primarily bla$^{KPC\text{-}2}$ (200, 55%) and bla$^{KPC\text{-}3}$ (161, 44%). Among carbapenemase-producing CG258 CR-Kp isolates, ST258 encompassed 92% of the isolates (334/364) (FIG. 14A). After CG258, the next most frequent clonal group was CG307 (44/593, 7%) (FIG. 14A). These strains were common in hospitals in Houston, TX. Similar to CG258, 37 (84%) of 44 CG307 isolates were carbapenemase-producing, with bla$^{KPC\text{-}2}$ detected in 35 (95%) of these 37 isolates. This information confirms earlier reports that dissemination of CR-Kp in the U.S. has been largely attributed to the clonal expansion of CG258, first identified in the U.S. in 2008. In the U.S., the ST258 dominates the CG258. The spread of CG258 has been associated with the carriage of genes encoding the KPC enzyme predominantly on F-type pKpQIL plasmids. Initial phylogenetic analysis of the SNPs in the core genome of 84 CR-Kp isolates revealed that ST258 constitutes predominantly of two major distinct genetic clades (clade 1 and clade 2). Genetic differentiation results from a ~215-kb region of divergence that includes genes involved in CPS biosynthesis. The region of divergence is a hotspot for DNA recombination events. A more recent analysis of the CPS genomic locus expanded these studies and also included ST11 strains, which is an ancestor of ST258, but these CR-Kp strains are not dominant in the western world. Ninety-six CR-Kp strains were analyzed and about half of the ST258 strains were shown to express the wzi154 CPS type and predominantly carry bla-$^{KPC\text{-}3}$. Infections with these bla-$^{KPC\text{-}3}$ CR-Kp strains (clade 2/wzi154 KL107) were associated with worse outcomes in bacteremia patients. Notably, a clade 2 CR-Kp strain was also responsible for the 2009 NIH outbreak. The wzi29 CPS type (KL106) is the most common wzi-type in clade 1. Wz50 (mostly KL51) expressing strains can be clade 1 or clade 2. Sequence analysis of other capsule-associated proteins (wzx, wzy, and wba) can further improve the assignment of KL types. Described herein are wzi-typing data on 380 CR-Kp strains (U.S.) derived from the CRACKLE-2 study. These data confirmed the prevalence of certain wzi types, namely 47.9% express wzi154 CPS, also referred to as capsule type KL107; 31% wzi29 (KL106); 6.6% wzi50; 6.0% wzi168) (FIG. 14B).

The characterization of 24D11 demonstrates that 24D11 exhibits cross-protective efficacy against wzi50, wzi29, and wzi154 ST258 strains (see, Example 1). Described herein are data showing: (1) Wzi typing data on 380 U.S. derived CR-Kp strains confirms wzi154, wzi29, and wzi50 are the most frequent strains (FIG. 14B); (2) Testing of 24D11 binding to 40 additional CR-Kp strains was performed. The results show agglutination of CR-Kp strains correlates with protection independent of degree of agglutination (FIG. 17); (3) Survival in whole blood cell (WBC) assay also correlates with protective efficacy; (4) Non agglutating strains exhibit no binding by Whole Cell Elisa, and no in vitro or in vivo protective efficacy with 24D11 (FIG. 17); (5) Repeat testing of 24D11 in intranasal model with wzi50, wzi29, and wzi154 ST258 strains confirms protective efficacy (FIG. 17B); and (6) Avibactam-Ceftazidime treatment in combination with 24D11 enhances clearance of CR-Kp (FIG. 19).

Figure 15A:
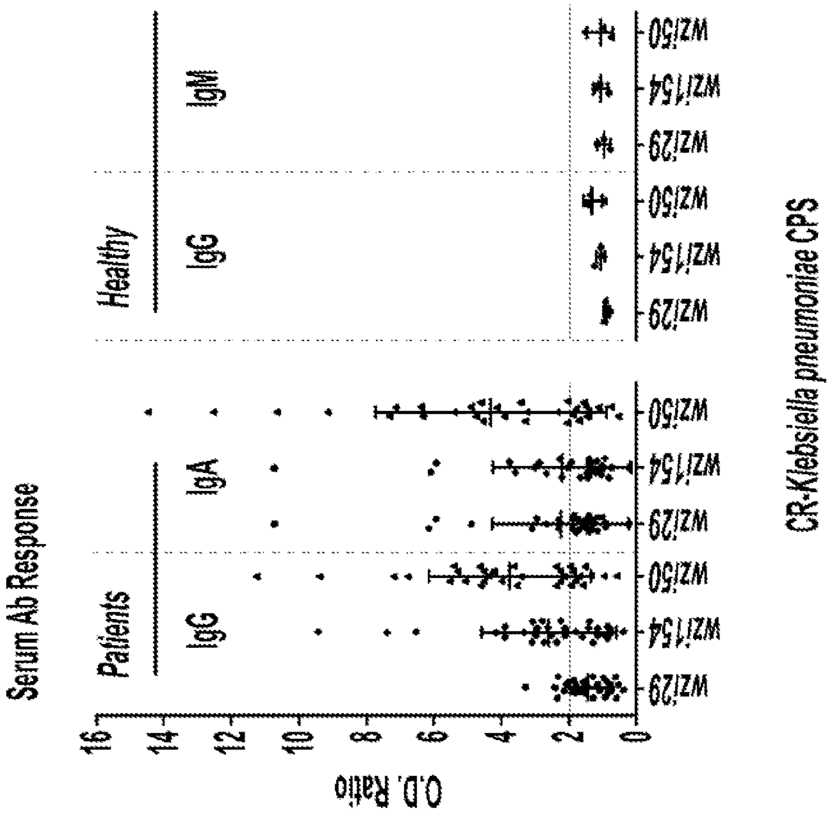
FIGS. 15A-B shows the humoral responses of pateints who have been previously infected with a CR-Kp strain against wzi29, wzi154, and wzi50, compared with the humoral response of healthy human controls. A wzi29-CPS-specific humoral response cannot be detected when purified CPS is used.
Figure 15B:
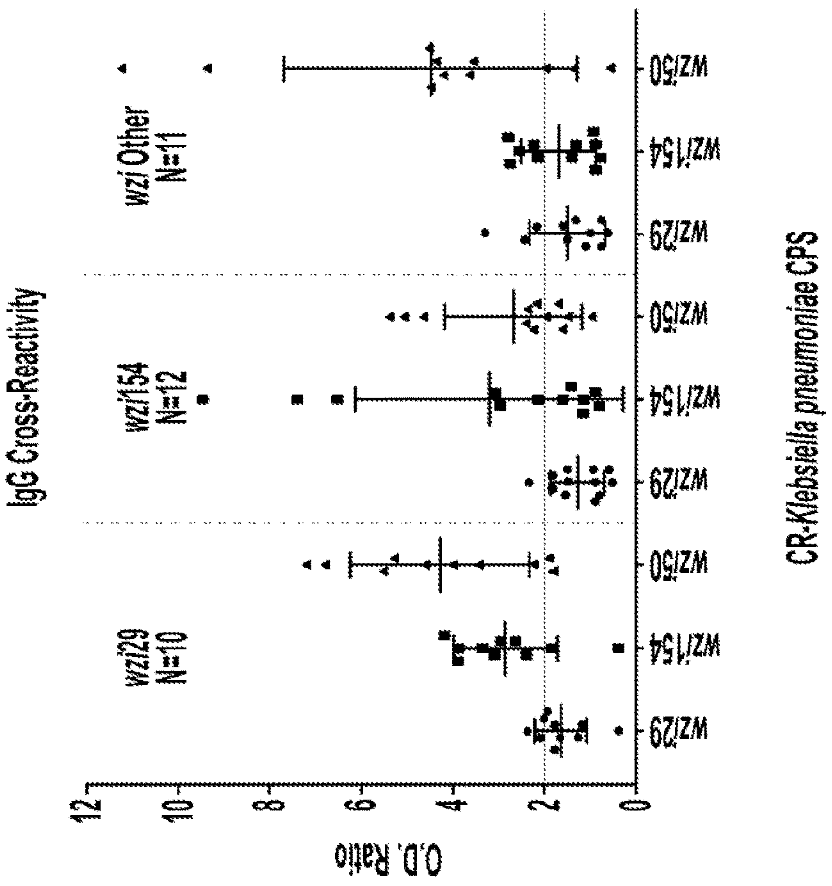

Monoclonal antibodies that bind wzi29-CPS (e.g. KL106), the major CPS type of clade 1 ST258 strains, could not be cloned. Thus, it was investigated whether infected patients mount a wzi29 CPS-specific monoclonal antibody response. Through participation in CRACKLE-2, the humoral anti-CPS response was studied in CR-Kp infected patients, from whom were also wzi-typed for the respective CR-Kp strain. The serological analysis yielded the following results. First, that infected patients indeed mount a wzi29-CPS-specific humoral response leading to the conclusion that the CPS purification process destroyed the CPS epitope of the wzi29 CPS. Second, it was found that serum antibodies of most CR-Kp infected patients bind wzi50 CPS (FIG. 15A) irrespective of the wzi type of the respective CR-Kp strain of the patient. This was also evident for patients infected with a CR-Kp strain that expressed wzi29-type CPS (FIG. 15B). It has also been shown that IgG-enriched sera (#116) from CR-Kp (wzi50)-infected patients conveyed serum resistance to MMC36, a wzi29 expressing CR-Kp strain. Most importantly, that enriched polyclonal serum (#116) also exhibited cross-protective efficacy against wzi154, wzi50, and wzi29 expressing CR-Kp strains (MMC34, SBU116, MMC36) in pulmonary infection models, where it lowered the bacterial lung burden (CFU). Depletion of wzi154- and wzi50-specific antibodies partially reversed the protective efficacy of the polyclonal serum. Depletion of wzi29-antibodies could not be performed, because purification of wzi29 CPS results in loss of important epitopes. CR-Kp strains that express wzi50 capsule type belong to CG258 and can be either clade 1 or 2.

Figure 16A:
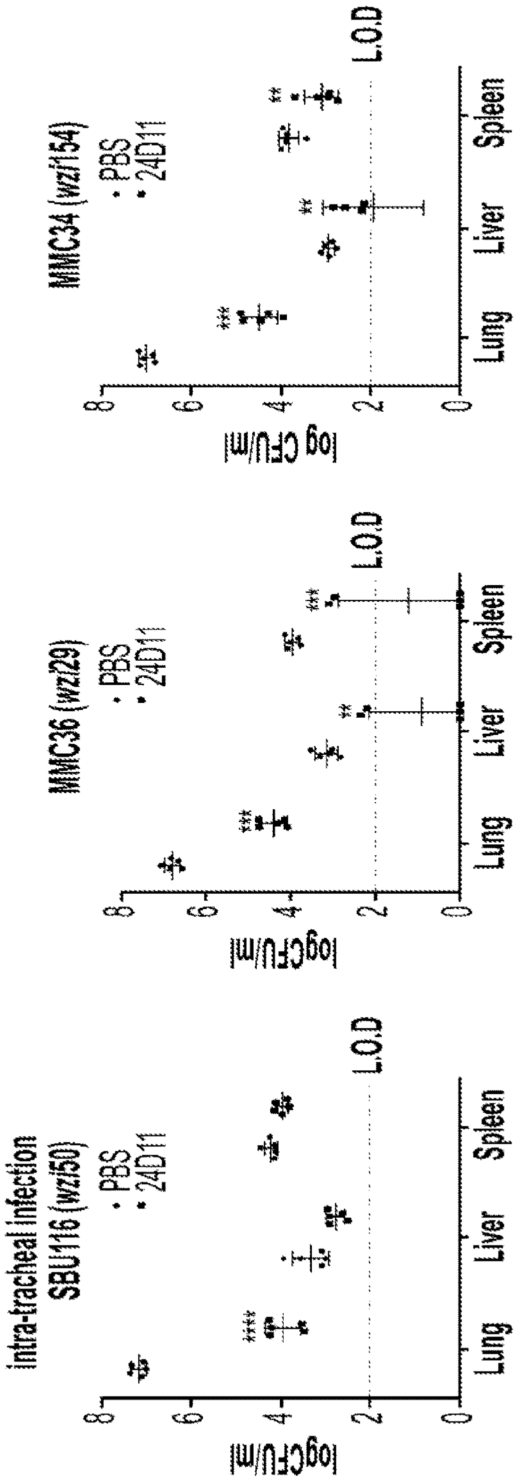
FIGS. 16A-B show CFU in mice 24 h after infection with 108 CFU/ml of SBU116 (wzi50), MMC36 (wzi29), and MMC34 (wzi154) strains and then treatment with PBS, isotype control antibody or 24D11 (10 mg/kg) 4 h after infection. Differences were compared and assessed for significance by multiple t-tests. Asterisk indicates if p-values were below 0.05 (*), 0.01 (), 0.001 (*), or 0.0001 (****).
Figure 16B:
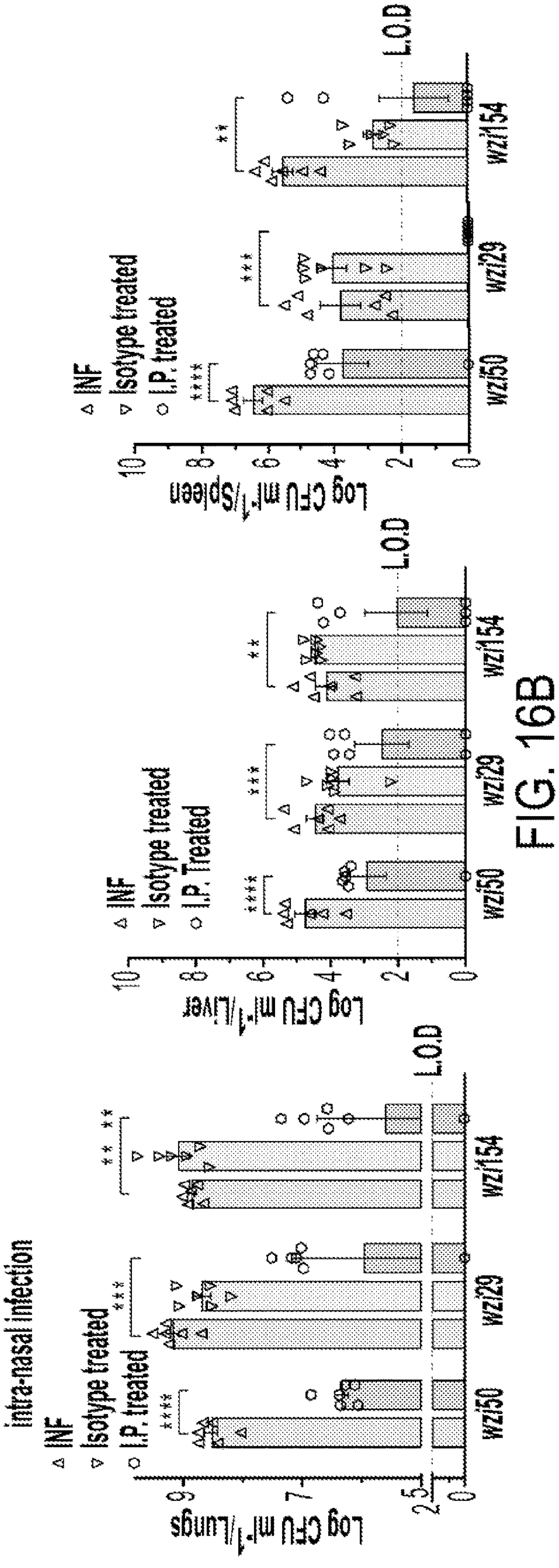

Characterization of monoclonal antibody 24D11's cross-protective efficacy shows it also protects in the intranasal model. The data described herein led to the testing that vaccination with wzi50 type CPS would elicit cross-protective antibodies. Murine hybridoma 24D11, which secretes monoclonal 24D11 (IgG2b), was cloned. 24D11 binds wzi50 and wzi154 with an affinity of 4.72 nM and 5.8 nM, respectively, which was also confirmed by SPR. Cross-reactivity and protective efficacy of monoclonal antibody 24D11 were studied using CR-Kp strains that express three prevalent CPS types (wzi29, wzi154, and wzi50), employing both in vitro and in vivo infection models. It was observed that in whole-blood cell (WBC) assays, monoclonal 24D11 induced significant killing of SBU116 (wzi50), MMC34 (wzi154), and MMC36 (wzi29) CR-Kp strains, whereas the wzi154-specific antibody 17H12 did not induce killing of MMC34 (wzi29). Importantly, 24D11 promotes phagocytosis of wzi29 expressing clade 1 ST258 CR-Kp strains. Using a murine intratracheal infection model, the results demonstrated that monoclonal antibody 24D11 reduces lung burden and dissemination of the three different CR-Kp strains (wzi29, wzi50. wzi154) given pre- and post-infection (FIG. 16A). The finding that treatment with monoclonal antibody 24D11 4 h after infection still resulted in significant protective efficacy (2-3 log decrease) supports clinical use of this monoclonal antibody. For MMC36 (wzi29) infected mice, i.p. treatment with monoclonal antibody 24D11 post-i.t. surgery also prevented dissemination to the limit of detection in the spleen and liver (FIG. 16A) in 3 out of 5 MMC36 infected mice.

Intra nasal infection of mice. Intra-nasal infection was performed with three Kp strains and treated with 24D11 4 h post-infection. Protective efficacy was confirmed (FIG. 17B).

Example 1 above shows that monoclonal antibody 24D11 was effective in neutropenic mice (FIG. 9). Patients with low neutrophil count (neutropenia) are prone to CR-Kp infection and have poor prognosis. To understand whether 24D11 can protect against ST258 CR-Kp infection in mice that mimics the neutropenic patient, the neutrophil counts were reduced in mice with Ly6G treatment and then they were infected with the bacteria before treating those mice with monoclonal antibody 24D11. It was observed that in neutropenic mice, monoclonal antibody 24D11 reduced bacterial load in the lung and reduced the spread of the bacteria in spleen. This finding is significant because many CR-Kp infected-patients have multiple co-morbidities such as cancer, and therefore, have limited host immune response. Lastly, a cocktail of monoclonal antibodies that combined wzi154-specific monoclonal antibody 17H12 with monoclonal antibody 24D11 showed significantly enhanced protection against wzi154 (MMC34) CR-Kp infected mice when compared to monotherapy with 17H12 but no difference was observed when compared to monotherapy with monoclonal antibody 24D11 (FIG. 11B). This finding is also important because it shows that monotherapy with 24D11 antibody will be sufficient. The variable region of the 24D11 monoclonal antibody was sequenced. The data described herein can be used as a vaccine and cross-protects against clade 1 and 2 of ST258 CR-Kp.

Binding data on CR-Kp strains. A collection of 38 CR-Kp strains derived from the SBU collection were tested (FIG. 17) and the data provide that monoclonal antibody 24D11 agglutinates 36 strains. Strains from a collection of extended-spectrum D-lactamases producing (ESBL+) Kp strains were also included. Many of those strains exhibit a wzi173 CPS. Some also were noted to have a wzi29 and wzi154 CPS type. Agglutination was measured in 96 well plates by incubating $10^6$ CFUs for 3 h with serial dilutions of monoclonal antibody 24D11 starting from 50 μg/ml and assessing agglutination by microscopy. ++++ reflects agglutination with 24D11 at 0.1-0.025 μg/ml, +++ at 0.8-0.2 μg/ml, ++ at 6.25-1.5 μg/ml, +50-12.5 μg/ml, respectively. For a negative control, an irrelevant isotype matched antibody (6D3,IgG2b), the a capsular strain 33576Δwzy, and SBU116 (ST307), were used. It has previously been shown that agglutination predicts protective efficacy, whereas macrophage and *Galleria mellonella* killing assays can be variable. Indeed, it was demonstrated with CR-Kp strains MMC34, MMC36, and SBU116 that WBC killing assays correlate with in vivo protection better than macrophage (J774.2) opsonophagocytosis assays (FIG. 7, and FIG. 5).

Protective efficacy was tested in five additional strains in the murine infection model. Non- and low-agglutinating strains were chosen. It was found that non-agglutinating strains do not bind 24D11 by whole cell ELISA (they do not demonstrate decreased survival in the WBC assay, and infection with these strains is not protected by 24D11 treatment. In contrast 24D11 exhibits in vitro and in vivo protective efficacy against low agglutinators Kp13 and Kp29. (The LD50 of CR-Kp strains is variable and was not titered for these experiments, which explains high CFU and suboptimal protection <2 log decrease in Kp14 and Kp29). Thus, the results described herein show that wzi-type, confirmed by agglutination or staining with fluorescently-labeled antibody, predicts protective efficacy. Protective effect is not correlated by degree of agglutination.

Figure 18:
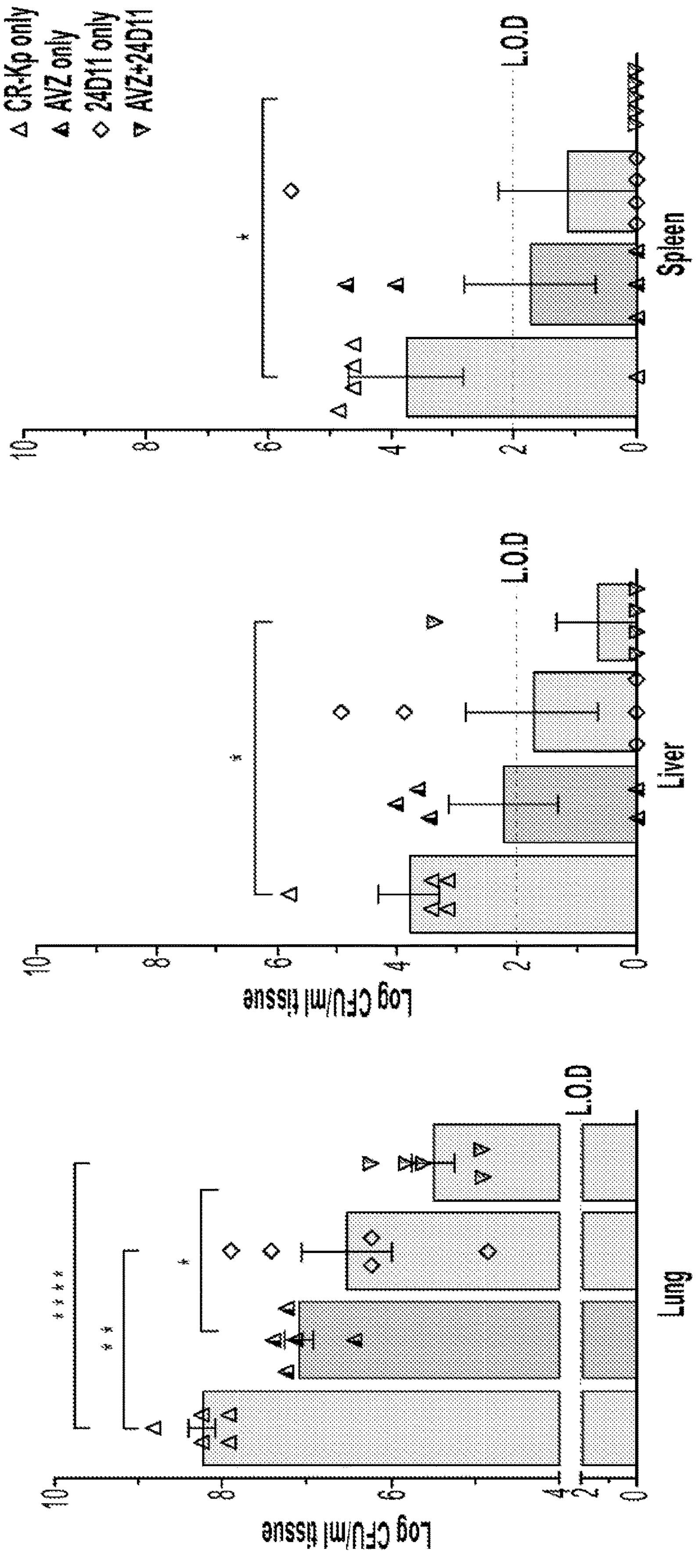
FIG. 18 shows C57/B6 mice (n=5) infected with MMC38/wzi50 and treated with 24D11 monoclonal antibody, Ceftazidime-Avibactam, or both in combination. Data indicates combination treatment enhances protective efficacy in the lung, liver and spleen.

Co-treatment with Ceftazidime-Avibactam. Murine experiments with 24D11 monoclonal antibody treated in combination with Ceftazidime-Avibactam (24 mg/6 mg/kg every 8 h) intra-peritoneally was performed. These data show that combination therapy enhances clearance from lung tissue (FIG. 18).

Monoclonal antibody 24D11 intranasal administration. It was assessed whether monoclonal antibody 24D11 can be administered intranasally and retain protective efficacy. Mice (C57BL/6) under Ketamine/Xylazine anesthesia were intranasally (I.N.) infected with $1\times10^8$ cells of ST258 clone *K. pneumoniae* (wzi50, wzi29 or wzi154 CPS type) and divided into groups (n:5): (i) Infected not treated; (ii) Infected I.P. and treated with mAb24D11 [10 mg/kg]; (iii) Infected I.N. and treated with mAb24D11 [10 mg/kg]; (iv) Infected I.N. and treated with isotype mAb [10 mg/kg]. In each group, the animals were administered mAb24D11 either intranasally or intraperitoneally. Animals were treated 4 hrs post infection and euthanized after 24 hours of infection. Lungs, liver and spleen were aseptically removed and processed to enumerate CFU ml−1/gram. Bacterial burden was assessed in lungs, liver and spleen, performed with *K. pneumoniae* (wzi50, wzi29 or wzi154). These data demonstrate that mAb 24D11 administered intraperitoneally versus intranasally results in comparable protective efficacy in mice infected with the three different wzi types. Thus, the results confirm that intranasal delivery of mAb 24D11 retains its protective efficacy which is similar to the results shown for i.p. administration.

What is claimed is:

1. An isolated antibody comprising a light chain variable region and a heavy chain variable region, wherein the light chain variable region comprises a complementarity determining region light chain 1 (CDRL1) amino acid sequence of SEQ ID NO: 1; a determining region light chain 2 (CDRL2) amino acid sequence of SEQ ID NO: 2; and a determining region light chain 3 (CDRL3) amino acid sequence of SEQ ID NO: 3; and wherein the heavy chain variable region comprises a complementarity determining region heavy chain 1 (CDRH1) amino acid sequence of SEQ ID NO: 5; a complementarity determining region heavy chain 2 (CDRH2) amino acid sequence of SEQ ID NO: 6; and a complementarity determining region heavy chain 3 (CDRH3) amino acid sequence of SEQ ID NO: 7.

2. The isolated antibody of claim 1, comprising a light chain variable region amino acid sequence of SEQ ID NO: 4.

3. The isolated antibody of claim 1, comprising a heavy chain variable region amino acid sequence of SEQ ID NO: 8.

4. The isolated antibody of claim 1, wherein a light chain variable region has an amino acid sequence that is at least 90% identical to amino acid sequence of SEQ ID NO: 4.

5. The isolated antibody of claim 1, wherein a heavy chain variable region has an amino acid sequence that is at least 90% identical to amino acid sequence of SEQ ID NO: 8.

6. The isolated antibody of claim 1, wherein the antibody is recombinantly engineered, chimerized, or humanized.

7. The isolated antibody of claim 1 wherein the antibody is a Fab, an Fab', an $F(ab')_2$, a Fv, a scFv, a diabody or fragments thereof.

8. The isolated antibody of claim 1, wherein the antibody binds to *Klebsiella pneumoniae* sequence type 258 wzi50 with an affinity of greater than or equal to 4.7 nM.

9. The isolated antibody of claim 1, wherein the antibody is a monoclonal antibody.

10. The isolated antibody of claim 1, wherein the antibody is linked to a detectable label.

11. The isolated antibody of claim 1, wherein the antibody is an IgG, an IgM, an IgA antibody or antigen binding fragment thereof.

12. A composition comprising the isolated antibody of claim 1, and at least one pharmaceutically acceptable carrier or diluent.

13. A method of inducing an immune response in a subject, the method comprising administering to the subject a therapeutically effective amount of an isolated antibody of claim 1.

14. The method of claim 13, wherein the subject is infected with *Klebsiella pneumonia* ST258 or *Klebsiella Pneumoniae*, and the immune response is complement-mediated or complement-independent opsonophagocytosis.

15. The method of claim 13, wherein the subject is infected or exposed to *Klebsiella pneumonia* ST258 or *Klebsiella pneumoniae*.

16. The method of claim 15, wherein the *Klebsiella pneumonia* ST258 or *Klebsiella pneumoniae* expresses wzi50, wzi154 or wzi29 capsular polysaccharides.

17. The method of claim 13, wherein the antibody is administered systemically, intravenously, intradermally, intramuscularly, intraperitoneally, subcutaneously, intranasally, or by aerosolization.

18. A method of inhibiting or treating a *Klebsiella pneumonia* ST258 infection or *Klebsiella pneumoniae* infection in a subject in need thereof, the method comprising administering to the subject a therapeutically effective amount of an isolated antibody of claim 1.

19. A method of reducing lung burden or dissemination of *Klebsiella pneumonia* ST258 or *Klebsiella pneumoniae* in a subject in need thereof, the method comprising administering to the subject a therapeutically effective amount of an isolated antibody of claim 1.

* * * * *